US011142762B2

(12) United States Patent
Dreyfuss et al.

(10) Patent No.: US 11,142,762 B2
(45) Date of Patent: Oct. 12, 2021

(54) U1 SNRNP REGULATES GENE EXPRESSION AND MODULATES ONCOGENICITY

(71) Applicant: The Trustees of the University of Pennsylvania, Philadelphia, PA (US)

(72) Inventors: Gideon Dreyfuss, Wynnewood, PA (US); Lili Wan, Westfield, NJ (US); Jung Min Oh, Philadelphia, PA (US); Anna Maria Pinto, Philadelphia, PA (US); Ihab Younis, Philadelphia, PA (US); Michael George Berg, Northbrook, IL (US); Daisuke Kaida, Toyama (JP)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/412,821

(22) PCT Filed: Jul. 5, 2013

(86) PCT No.: PCT/US2013/049451
§ 371 (c)(1),
(2) Date: Jan. 5, 2015

(87) PCT Pub. No.: WO2014/008474
PCT Pub. Date: Jan. 9, 2014

(65) Prior Publication Data
US 2015/0191724 A1 Jul. 9, 2015

Related U.S. Application Data

(60) Provisional application No. 61/668,168, filed on Jul. 5, 2012.

(51) Int. Cl.
| | | |
|---|---|---|
| C12N 15/11 | (2006.01) | |
| C12N 15/113 | (2010.01) | |
| A61K 31/7088 | (2006.01) | |
| A61K 31/7105 | (2006.01) | |
| C12N 15/67 | (2006.01) | |

(52) U.S. Cl.
CPC ........ *C12N 15/113* (2013.01); *A61K 31/7088* (2013.01); *A61K 31/7105* (2013.01); *C12N 15/67* (2013.01); *C12N 2310/11* (2013.01); *C12N 2310/3233* (2013.01)

(58) Field of Classification Search
CPC ..... C12N 15/111; C12N 15/113; C12N 15/11; C12N 15/67; C12N 2320/50
See application file for complete search history.

(56) References Cited

U.S. PATENT DOCUMENTS

| | | | | |
|---|---|---|---|---|
| 2003/0082149 A1* | 5/2003 | Rowe | ................. | C12N 15/113 424/93.21 |
| 2005/0043261 A1* | 2/2005 | Alonso | ................. | C12N 15/63 514/44 A |
| 2010/0099739 A1* | 4/2010 | Gunderson | ........ | A61K 31/7088 514/44 A |
| 2010/0249022 A1* | 9/2010 | Clapham | .............. | C07K 14/705 514/3.8 |
| 2012/0165394 A1 | 6/2012 | Singh et al. | | |
| 2013/0210902 A1* | 8/2013 | Pagani | .................. | C12N 15/111 514/44 R |

FOREIGN PATENT DOCUMENTS

| | | | |
|---|---|---|---|
| WO | 94/20141 A1 | 9/1994 | |
| WO | 2008/121963 A2 | 9/2008 | |
| WO | WO 2011159836 A2 * | 12/2011 | ........... C12N 15/111 |

OTHER PUBLICATIONS

Crispino et al., Complementation by SR proteins of pre-mRNA splicing reactions depleted of U1 snRNP, 1994, Science, vol. 265, pp. 1866-1869.*
Huang et al., RBFOX2 promotes protein 4.1 R exon 16 selection via U1 snRNP recruitment, 2012, Molecular and Cellular Biology, vol. 32, pp. 513-526.*
Jodelka et al., A feedback loop regulates splicing of the spinal muscular atrophy-modifying gene, SMN2, 2010, Human Molecular Genetics, vol. 19, pp. 4906-4917.*
Nick J. Proudfoot, Ending the message: poly(A) signals then and now, 2011, Genes & Development, vol. 25, pp. 1770-1782.*
Polyak et al., Transitions between epithelial and mesenchymal states: acquisition of malignant and stem cell traits, 2009, Nature Reviews Cancer, vol. 9, pp. 265-273.*
Homo sapiens NICE-4 protein (NICE-4), mRNA, NCBI Reference Sequence: NM_014847.1, accessed and retrieved from www.ncbi.nlm.nih.gov on May 15, 2020. (Year: 2003).*
Homo sapiens ubiquitin associated protein 2 like (UBAP2L), transcript variant 1, mRNA, NCBI Reference Sequence: NM_014847.4, accessed and retrieved from www.ncbi.nlm.nih.gov on May 15, 2020. (Year: 2020).*
Albini et al. A Rapid in Vitro Assay for Quantitating the Invasive Potential of Tumor Cells, Jun. 15, 1987, Cancer Res 47(12):3239-45.
Ashe et al.Stem-loop 1 of the U1 snRNP plays a critical role in the suppression of HIV-1 polyadenylation, 2000, RNA 6(2):170-177.
Beaudoing et al. Patterns of Variant Polyadenylation Signal Usage in Human Genes, 2000, Genome Res 10:1001-1010.

(Continued)

*Primary Examiner* — Dana H Shin
(74) *Attorney, Agent, or Firm* — Riverside Law LLP

(57) ABSTRACT

The invention provides a method of regulating U1 activity associated with its splicing role as well as its role in protecting pre-mRNAs from premature termination by cleavage and polyadenylation, thereby modulating expression of a gene or genes. In one embodiment, the invention includes compositions and methods for regulating gene expression and treating diseases associated with dysregulated gene expression.

6 Claims, 26 Drawing Sheets
Specification includes a Sequence Listing.

(56) References Cited

OTHER PUBLICATIONS

Berg et al. U1 snRNP Determines Mrna Length and Regulates Isoform Expression, Jul. 6, 2012, Cell 150(1):53-64.
Brody et al.The In Vivo Kinetics of RNA Polymerase II Elongation during the Co-Transcriptional Splicing, 2011, PLoS Biol 9:e1000573.
Buratowski, Progression through the RNA polymerase II CTD cycle, Nov. 25, 2009, Mol Cell 36:541-546.
Calvo and Manley, Strange bedfellows: polyadenylation factors at the promoter, Aug. 4, 2003, Genes Dev 17:1321-1327.
Das et al., 2007, Sr Proteins in Coupling RNAP II Transcription to Pre-Mrna Splicing Mol Cell 26:867-881.
De Klerk et al.,Poly(A) binding protein nuclear 1 levels affect alternative polyadenylation, Jul. 6, 2012, Nucleic Acids Res 40(18):9089-101.
Di Giammartino et al.Mechanisms and consequences of alternative polyadenylation, Sep. 16, 2011, Mol Cell 43(6):853-66.
Ebert and Sharp, Roles for microRNAs in conferring robustness to biological processes, Apr. 27, 2012, Cell 149(3):515-24.
Edwalds-Gilbert et al., Alternative poly(A) site selection in complex transcription units: means to an end, 1997, Nucleic Acids Res 25:2547-2561.
Elkon et al., E2F mediates enhanced alternative polyadenylation in proliferation 2012, Genome Biol 13(7):R59.
Flavell et al.Genome-wide analysis of MEF2 transcriptional program reveals synaptic target genes and neuronal activity-dependent polyadenylation site selection, Dec. 26, 2008, Neuron 60:1022-1038.
Fortes et al. Inhibiting expression of specific genes in mammalian cells with 5' end-mutated U1 small nuclear RNAs targeted to terminal exons of pre-Mrna , Jul. 8, 2003, Proc Natl Acad Sci USA 100:8264-8269.
Fu et al.Differential genome-wide profiling of tandem 3' UTRs among human breast cancer and normal cells by high-throughput sequencing, 2011, Genome Res 21(5):741-7).
Furic et al. Eif4e phosphorylation promotes tumorigenesis and is associated with prostate cancer progression, 2010, Proc Natl Acad Sci USA 7(32):14134-9.
Futreal et al., A census of Cancer Genes 2004, Nat Rev Cancer 4(3):177-83.
Glover-Cutter et al. RNA polymerase II pauses and associates with pre-Mrna processing factors at both ends of genes, 2008, Nat Struct Mol Biol 15:71-78.
Guo et al., Poly(A) Signals Located near the 5' End of Genes Are Silenced by a General Mechanism That Prevents Premature 3'—End Processing 2011, Mol Cell Biol 31:639-651.
Hu et al.Bioinformatic identification of candidate cis-regulatory elements involved in human mrna polyadenylation , 2005, RNA 11:1485-1493.
Ji and Tian, Reprogramming of 3' Untranslated Regions of mrnas by alternative polyadenylation in Generation of Pluripotent Stem Cells from Different Cell Types, 2009, PLoS One 4:e8419.
Johnson et al. The Iet-7 MicroRNA Represses Cell Proliferation Pathways in Human Cells, 2007, Cancer Res 67(16):7713-22.
Kaida et al.U1 snRNP protects pre-Mrnas from premature cleavage and polyadenylation, 2010, Nature 468:664-668.
Lee et al. MicroRNA15a modulates expression of the cell-cycle regulator Cdc25A and affects hepatic cystogenesis in a rat model of polycystic kidney disease, 2008, J Clin Invest 118(11):3714-24.
Lembo et al Shortening of 3' UTRs Correlates with Poor Prognosis in Breast and Lung Cancer., 2012, PLoS One 7(2):e31129.
Lewis et al. A nuclear cap-binding complex facilitates association of U1 snRNP with the cap-proximal 5' splice site, 1996, Genes Dev 10:1683-1698.
Lin et al. An in-depth map of polyadenylation sites in cancer, 2012, Nucleic Acids Res 40(17):8460-71.
Loebrich and Nedivi, The function of Activity-Regulated Genes in the Nervous System 2009, Physiol Rev 89(4):1079-1103.
Lou et al. An intron enhancer recognized by splicing factors activates polyadenylation, 1996, Genes Dev 10:208-219.

Lutz et al. Interaction between the U1 snRNP-A Protein and the 160-Kd subunit of cleavage-polyadenylation specificity factor increases polyadenylation efficiency in vitro , 1996, Genes Dev 10:325-337.
Majid et al.MicroRNA-205 inhibits Src-mediated oncogenic pathways in renal cancer, 2011, Cancer Res 71(7):2611-21.
Mayr and Bartel, Widespread shortening of 3'UTRs by alternative cleavage and polyadenylation activates oncogenes in cancer cells 2009, Cell 138(4):673-84.
Medrano and Pardee, Prevalent deficiency in tumor cells of cycloheximide-induced cycle arrest 1980, Proc Natl Acad Sci USA 77(7):4123-6.
Mendell and Olson, MicroRNAs in stress signaling and human disease, 2012, Cell 148(6):1172-87.
Paranjape et al. A 3'-untranslated region KRAS variant and triple-negative breast cancer: a case-control and genetic analysis, 2011, Lancet Oncol 12(4):377-86).
Patel et al. Splicing-independent recruitment of spliceosomal small nuclear RNPs to nascent RNA polymerase II transcripts, 2007, J Cell Biol 178:937-949.
Sala et al., Inhibition of Dendritic Spine Morphogenesis and Synaptic Transmission by Activity-Inducibile Protein Homer1a 2003, J Neurosci 23:6327-6337.
Sandberg et al.Proliferating cells express mrsnas with shortened 3' UTRs andf fewer micro RNA target sites, 2008, Science 320:1643-1647.
Shell et al.Elevated Levels of the 64-kDa Cleavage Stimulatory Factor (CstF) in Lipopolysaccharide-stimulated Macrophages Influence Gene Expression and Induce Alternative Poly(A) Site Selection , 2005, J Biol Chem 280:39950-39961.
Spiluttini et al. Splicing-independent recruitment U1 snRNP to a transcription unit in living cells, 2010, J Cell Sci 123:2085-2093.
Tavazoie et al., Endogenous human microRNAs that suppress breast cancer metastasis 2008, Nature 451(7175):147-52.
Tian et al., 2005, A large-scale analysis of Mrna polyadenylation of human mouse genes Nucleic Acids Res 33:201-212.
Tian et al. widespread Mrna polydenylation events in introns indicate dynamic interplay between polydenylation and splicing , 2007, Genome Res 17:156-165.
Vagner et al., Position-dependent inhibition of the cleavage step of pre-Mrna 3'—end processing by U1 snRNP 2000, RNA 6(2):178-188.
Wan et al. MicroRNA negatively regulates Cdc25A and cell cycle progression in colon cancer cells, 2009, Cancer Res 69(20):8157-65.
Webster et al. Regulation of Epidermal Growth Factor Receptor Signaling in Human Cancer Cells by MicroRNA-7, 2009, J Biol Chem 284(9):5731-41.
Wu et al. MiR-339-5p inhibits breast cancer cell migration and invasion in vitro and may be a potential biomarker for breast cancer prognosis, 2010, BMC Cancer 10:542.
Yao et al. Transcriptome-wide analyses of CstF64-RNA interactions in global regulation of Mrna alternative polyadenylation, 2012, Proc Natl Acad Sci U S A 109(46):18773-8.
Zhang et al. Biased alternative polyadenylation in human tissues, 2005, Genome Biol 6(12):R100.
Tranter et al., "Coordinated Post-transcriptional Regulation of Hsp70.3 Gene Expression by MicroRNA and Alternative Polyadenylation", The Journal of Biological Chemistry, vol. 286, No. 34:29828-29837, 2011.
David et al., "Alternative pre-mRNA splicing regulation in cancer: pathways and programs unhinged", Genes Dev, 24:2343-2364, 2010.
Stamm et al., "Regulation of the neuron-specific exon of clathrin light chain B", Molecular Brain Research, 64:108-118, 1999.
Merkhofer et al., "U1 snRNA Rewrites the Script", Cell, 150:9-11, 2012.
Gunderson et al., "U1 snRNP Inhibits Pre-mRNA Polyadenylation through a Direct Interaction between U1 70K and Poly(A) Polymerase", Mol Cell, 1:255-264, 1998.

(56) References Cited

OTHER PUBLICATIONS

Gunderson et al., "The Human U1 A snRNP Protein Regulates Polyadenylation via a Direct Interaction with Poly(A) Polymerase", Cell, 76:531-541, 1994.

* cited by examiner

SEQUENCE LISTING

<160> NUMBER OF SEQ ID NOS: 63

<210> SEQ ID NO 1
<211> LENGTH: 9
<212> TYPE: DNA
<213> ORGANISM: Artificial Sequence
<220> FEATURE:
<223> OTHER INFORMATION: Wild-type 5' splice site recognition sequence
      of U1

<400> SEQUENCE: 1 acttacctg                                                                9

<210> SEQ ID NO 2
<211> LENGTH: 9
<212> TYPE: DNA
<213> ORGANISM: Artificial Sequence
<220> FEATURE:
<223> OTHER INFORMATION: U1-A: mutated 5' splice site recognition
      sequence of U1

<400> SEQUENCE: 2 ctgctgttg                                                                9

<210> SEQ ID NO 3
<211> LENGTH: 9
<212> TYPE: DNA
<213> ORGANISM: Artificial Sequence
<220> FEATURE:
<223> OTHER INFORMATION: U1-B: mutated 5' splice site recognition
      sequence of U1

<400> SEQUENCE: 3 tgaatggac                                                                9

<210> SEQ ID NO 4
<211> LENGTH: 9
<212> TYPE: DNA
<213> ORGANISM: Artificial Sequence
<220> FEATURE:
<223> OTHER INFORMATION: U1-C: mutated 5' splice site recognition
      sequence of U1

<400> SEQUENCE: 4 ctacagatg                                                                9

<210> SEQ ID NO 5
<211> LENGTH: 9
<212> TYPE: DNA
<213> ORGANISM: Artificial Sequence
<220> FEATURE:
<223> OTHER INFORMATION: U1-D: mutated 5' splice site recognition
      sequence of U1

<400> SEQUENCE: 5 cacccctac                                                                9

<210> SEQ ID NO 6
<211> LENGTH: 25
<212> TYPE: DNA
<213> ORGANISM: Artificial Sequence
<220> FEATURE:
<223> OTHER INFORMATION: Chemically synthesized

<400> SEQUENCE: 6
cctcttacct cagttacaat ttata                                             25

<210> SEQ ID NO 7
<211> LENGTH: 25
<212> TYPE: DNA
<213> ORGANISM: Artificial Sequence
<220> FEATURE:
<223> OTHER INFORMATION: Chemically synthesized

<400> SEQUENCE: 7
ggtatctccc ctgccaggta agtat                                          25

<210> SEQ ID NO 8
<211> LENGTH: 25
<212> TYPE: DNA
<213> ORGANISM: Artificial Sequence
<220> FEATURE:
<223> OTHER INFORMATION: Chemically synthesized

<400> SEQUENCE: 8
tgataagaac agatactaca cttga                                          25

<210> SEQ ID NO 9
<211> LENGTH: 25
<212> TYPE: DNA
<213> ORGANISM: Artificial Sequence
<220> FEATURE:
<223> OTHER INFORMATION: Chemically synthesized

<400> SEQUENCE: 9
aaccttctct cctttcatac aacac                                          25

<210> SEQ ID NO 10
<211> LENGTH: 24
<212> TYPE: DNA
<213> ORGANISM: Artificial Sequence
<220> FEATURE:
<223> OTHER INFORMATION: Chemically synthesized

<400> SEQUENCE: 10
tcgttatttt ccttactcat aagt                                           24

<210> SEQ ID NO 11
<211> LENGTH: 25
<212> TYPE: DNA
<213> ORGANISM: Artificial Sequence
<220> FEATURE:
<223> OTHER INFORMATION: Chemically synthesized

<400> SEQUENCE: 11
gttaacctct acgccaggta agtat                                          25

<210> SEQ ID NO 12
<211> LENGTH: 25
<212> TYPE: DNA
<213> ORGANISM: Artificial Sequence
<220> FEATURE:
<223> OTHER INFORMATION: Chemically synthesized

<400> SEQUENCE: 12
gataagaaca gatactacac tttga                                          25

<210> SEQ ID NO 13
<211> LENGTH: 25
<212> TYPE: DNA
<213> ORGANISM: Artificial Sequence
<220> FEATURE:
<223> OTHER INFORMATION: Chemically synthesized

<400> SEQUENCE: 13
aacttgctct ccttccaaac aacac                                25

<210> SEQ ID NO 14
<211> LENGTH: 25
<212> TYPE: DNA
<213> ORGANISM: Artificial Sequence
<220> FEATURE:
<223> OTHER INFORMATION: Chemically synthesized

<400> SEQUENCE: 14
gattggtttt ccttactcat tagtt                                25

<210> SEQ ID NO 15
<211> LENGTH: 25
<212> TYPE: DNA
<213> ORGANISM: Artificial Sequence
<220> FEATURE:
<223> OTHER INFORMATION: Chemically synthesized

<400> SEQUENCE: 15
ggatattttc ttcctaaaag gaatc                                25

<210> SEQ ID NO 16
<211> LENGTH: 25
<212> TYPE: DNA
<213> ORGANISM: Artificial Sequence
<220> FEATURE:
<223> OTHER INFORMATION: Chemically synthesized

<400> SEQUENCE: 16
aataccacag tttattgaag actac                                25

<210> SEQ ID NO 17
<211> LENGTH: 59
<212> TYPE: DNA
<213> ORGANISM: Artificial Sequence
<220> FEATURE:
<223> OTHER INFORMATION: Chemically synthesized

<400> SEQUENCE: 17
cgtatcgcct ccctcgcgcc atcagacgag tgcgtgctcg agcggccgcc cgggcaggt    59

<210> SEQ ID NO 18
<211> LENGTH: 58
<212> TYPE: DNA
<213> ORGANISM: Artificial Sequence
<220> FEATURE:
<223> OTHER INFORMATION: Chemically synthesized

<400> SEQUENCE: 18
ctatgcgcct tgccagcccg ctcagacgag tgcgtggcag cgtggtcgcg gccgaggt     58

<210> SEQ ID NO 19
<211> LENGTH: 59
<212> TYPE: DNA
<213> ORGANISM: Artificial Sequence
<220> FEATURE:
<223> OTHER INFORMATION: Chemically synthesized

<400> SEQUENCE: 19
cgtatcgcct ccctcgcgcc atcagacgct cgacagctcg agcggccgcc cgggcaggt    59

<210> SEQ ID NO 20

```
<211> LENGTH: 58
<212> TYPE: DNA
<213> ORGANISM: Artificial Sequence
<220> FEATURE:
<223> OTHER INFORMATION: Chemically synthesized

<400> SEQUENCE: 20
ctatgcgcct tgccagcccg ctcagacgct cgacaggcag cgtggtcgcg gccgaggt      58

<210> SEQ ID NO 21
<211> LENGTH: 20
<212> TYPE: DNA
<213> ORGANISM: Artificial Sequence
<220> FEATURE:
<223> OTHER INFORMATION: Chemically synthesized

<400> SEQUENCE: 21
cagtctgcca ttgtgacgtg                                                20

<210> SEQ ID NO 22
<211> LENGTH: 20
<212> TYPE: DNA
<213> ORGANISM: Artificial Sequence
<220> FEATURE:
<223> OTHER INFORMATION: Chemically synthesized

<400> SEQUENCE: 22
ccaatgggag agccctaaac                                                20

<210> SEQ ID NO 23
<211> LENGTH: 19
<212> TYPE: DNA
<213> ORGANISM: Artificial Sequence
<220> FEATURE:
<223> OTHER INFORMATION: Chemically synthesized

<400> SEQUENCE: 23
ctgcaatggg agttgggag                                                 19

<210> SEQ ID NO 24
<211> LENGTH: 21
<212> TYPE: DNA
<213> ORGANISM: Artificial Sequence
<220> FEATURE:
<223> OTHER INFORMATION: Chemically synthesized

<400> SEQUENCE: 24
gatgcgtttg attctgccca c                                              21

<210> SEQ ID NO 25
<211> LENGTH: 25
<212> TYPE: DNA
<213> ORGANISM: Artificial Sequence
<220> FEATURE:
<223> OTHER INFORMATION: Chemically synthesized

<400> SEQUENCE: 25
gaggagctct ccaaactgat cagcg                                          25

<210> SEQ ID NO 26
<211> LENGTH: 20
<212> TYPE: DNA
<213> ORGANISM: Artificial Sequence
<220> FEATURE:
<223> OTHER INFORMATION: Chemically synthesized

<400> SEQUENCE: 26
```
ctgatcagcg gctttgacca                                              20

<210> SEQ ID NO 27
<211> LENGTH: 27
<212> TYPE: DNA
<213> ORGANISM: Artificial Sequence
<220> FEATURE:
<223> OTHER INFORMATION: Chemically synthesized

<400> SEQUENCE: 27
cgagtatgag tcgactctag actgccg                                      27

<210> SEQ ID NO 28
<211> LENGTH: 21
<212> TYPE: DNA
<213> ORGANISM: Artificial Sequence
<220> FEATURE:
<223> OTHER INFORMATION: Chemically synthesized

<400> SEQUENCE: 28
ctctagactg ccgcgacgtg g                                            21

<210> SEQ ID NO 29
<211> LENGTH: 40
<212> TYPE: DNA
<213> ORGANISM: Artificial Sequence
<220> FEATURE:
<223> OTHER INFORMATION: Chemically synthesized

<400> SEQUENCE: 29
ctgatctaga ggtaccggat cctttttttt tttttttttt                        40

<210> SEQ ID NO 30
<211> LENGTH: 22
<212> TYPE: DNA
<213> ORGANISM: Artificial Sequence
<220> FEATURE:
<223> OTHER INFORMATION: Chemically synthesized

<400> SEQUENCE: 30
ctgatctaga ggtaccggat cc                                           22

<210> SEQ ID NO 31
<211> LENGTH: 25
<212> TYPE: DNA
<213> ORGANISM: Artificial Sequence
<220> FEATURE:
<223> OTHER INFORMATION: Chemically synthesized

<400> SEQUENCE: 31
gctaactcag gggctgcata ggcac                                        25

<210> SEQ ID NO 32
<211> LENGTH: 25
<212> TYPE: DNA
<213> ORGANISM: Artificial Sequence
<220> FEATURE:
<223> OTHER INFORMATION: Chemically synthesized

<400> SEQUENCE: 32
cgtccttctc gccctccttc tcctc                                        25

<210> SEQ ID NO 33
<211> LENGTH: 23
<212> TYPE: DNA

<213> ORGANISM: Artificial Sequence
<220> FEATURE:
<223> OTHER INFORMATION: Chemically synthesized

<400> SEQUENCE: 33
gggtggcttt cttaatttgc atc                                       23

<210> SEQ ID NO 34
<211> LENGTH: 22
<212> TYPE: DNA
<213> ORGANISM: Artificial Sequence
<220> FEATURE:
<223> OTHER INFORMATION: Chemically synthesized

<400> SEQUENCE: 34
gatgatttcc attgctgcca cg                                        22

<210> SEQ ID NO 35
<211> LENGTH: 25
<212> TYPE: DNA
<213> ORGANISM: Artificial Sequence
<220> FEATURE:
<223> OTHER INFORMATION: Chemically synthesized

<400> SEQUENCE: 35
gtcttgaaac cacagcagtg cccag                                     25

<210> SEQ ID NO 36
<211> LENGTH: 25
<212> TYPE: DNA
<213> ORGANISM: Artificial Sequence
<220> FEATURE:
<223> OTHER INFORMATION: Chemically synthesized

<400> SEQUENCE: 36
ctcagcactg acggccttgt tgagt                                     25

<210> SEQ ID NO 37
<211> LENGTH: 24
<212> TYPE: DNA
<213> ORGANISM: Artificial Sequence
<220> FEATURE:
<223> OTHER INFORMATION: Chemically synthesized

<400> SEQUENCE: 37
cagacgatga gagaacaccc gatg                                      24

<210> SEQ ID NO 38
<211> LENGTH: 23
<212> TYPE: DNA
<213> ORGANISM: Artificial Sequence
<220> FEATURE:
<223> OTHER INFORMATION: Chemically synthesized

<400> SEQUENCE: 38
tggcacctct gtgggcctgt ggc                                       23

<210> SEQ ID NO 39
<211> LENGTH: 27
<212> TYPE: DNA
<213> ORGANISM: Artificial Sequence
<220> FEATURE:
<223> OTHER INFORMATION: Chemically synthesized

<400> SEQUENCE: 39
ctgttgcttc cactgcttca cattggc                                   27

<210> SEQ ID NO 40
<211> LENGTH: 22
<212> TYPE: DNA
<213> ORGANISM: Artificial Sequence
<220> FEATURE:
<223> OTHER INFORMATION: Chemically synthesized

<400> SEQUENCE: 40
aaggataagc agtgtgaaca ag                                          22

<210> SEQ ID NO 41
<211> LENGTH: 20
<212> TYPE: DNA
<213> ORGANISM: Artificial Sequence
<220> FEATURE:
<223> OTHER INFORMATION: Chemically synthesized

<400> SEQUENCE: 41
tctagatctc ccatcacggc                                             20

<210> SEQ ID NO 42
<211> LENGTH: 20
<212> TYPE: DNA
<213> ORGANISM: Artificial Sequence
<220> FEATURE:
<223> OTHER INFORMATION: Chemically synthesized

<400> SEQUENCE: 42
cagcagtgcc gaaagacata                                             20

<210> SEQ ID NO 43
<211> LENGTH: 26
<212> TYPE: DNA
<213> ORGANISM: Artificial Sequence
<220> FEATURE:
<223> OTHER INFORMATION: Chemically synthesized

<400> SEQUENCE: 43
cgcctatcag tctgtccctg gactcc                                      26

<210> SEQ ID NO 44
<211> LENGTH: 25
<212> TYPE: DNA
<213> ORGANISM: Artificial Sequence
<220> FEATURE:
<223> OTHER INFORMATION: Chemically synthesized

<400> SEQUENCE: 44
ccttcctttg gtaaggaggc tgccc                                       25

<210> SEQ ID NO 45
<211> LENGTH: 22
<212> TYPE: DNA
<213> ORGANISM: Artificial Sequence
<220> FEATURE:
<223> OTHER INFORMATION: Chemically synthesized

<400> SEQUENCE: 45
ccggaattgc tgagtaagct gg                                          22

<210> SEQ ID NO 46
<211> LENGTH: 23
<212> TYPE: DNA
<213> ORGANISM: Artificial Sequence
<220> FEATURE:

<223> OTHER INFORMATION: Chemically synthesized

<400> SEQUENCE: 46
ggaaggcata tactggcaaa tgc                                           23

<210> SEQ ID NO 47
<211> LENGTH: 24
<212> TYPE: DNA
<213> ORGANISM: Artificial Sequence
<220> FEATURE:
<223> OTHER INFORMATION: Chemically synthesized

<400> SEQUENCE: 47
cctttagctc ctcgaattta acag                                          24

<210> SEQ ID NO 48
<211> LENGTH: 24
<212> TYPE: DNA
<213> ORGANISM: Artificial Sequence
<220> FEATURE:
<223> OTHER INFORMATION: Chemically synthesized

<400> SEQUENCE: 48
ccttgatgaa cttcctcaga ggac                                          24

<210> SEQ ID NO 49
<211> LENGTH: 21
<212> TYPE: DNA
<213> ORGANISM: Artificial Sequence
<220> FEATURE:
<223> OTHER INFORMATION: Chemically synthesized

<400> SEQUENCE: 49
ggttggtgat ggtggtactg g                                             21

<210> SEQ ID NO 50
<211> LENGTH: 23
<212> TYPE: DNA
<213> ORGANISM: Artificial Sequence
<220> FEATURE:
<223> OTHER INFORMATION: Chemically synthesized

<400> SEQUENCE: 50
gatttcgcct tcactttcct gtc                                           23

<210> SEQ ID NO 51
<211> LENGTH: 29
<212> TYPE: DNA
<213> ORGANISM: Artificial Sequence
<220> FEATURE:
<223> OTHER INFORMATION: Chemically synthesized

<400> SEQUENCE: 51
gtgtggatgt agtacacatg gatgaaaac                                     29

<210> SEQ ID NO 52
<211> LENGTH: 28
<212> TYPE: DNA
<213> ORGANISM: Artificial Sequence
<220> FEATURE:
<223> OTHER INFORMATION: Chemically synthesized

<400> SEQUENCE: 52
ttattgtaca ccaggacctt ctccacag                                      28

-continued

<210> SEQ ID NO 53
<211> LENGTH: 28
<212> TYPE: DNA
<213> ORGANISM: Artificial Sequence
<220> FEATURE:
<223> OTHER INFORMATION: Chemically synthesized

<400> SEQUENCE: 53
caactatggc tgtggagaag gtcctggt                                          28

<210> SEQ ID NO 54
<211> LENGTH: 31
<212> TYPE: DNA
<213> ORGANISM: Artificial Sequence
<220> FEATURE:
<223> OTHER INFORMATION: Chemically synthesized

<400> SEQUENCE: 54
tctgacctgg agacgaaact gtagagtatc t                                      31

<210> SEQ ID NO 55
<211> LENGTH: 22
<212> TYPE: DNA
<213> ORGANISM: Artificial Sequence
<220> FEATURE:
<223> OTHER INFORMATION: Chemically synthesized

<400> SEQUENCE: 55
caacagacat tgctgaagaa ac                                                22

<210> SEQ ID NO 56
<211> LENGTH: 18
<212> TYPE: DNA
<213> ORGANISM: Artificial Sequence
<220> FEATURE:
<223> OTHER INFORMATION: Chemically synthesized

<400> SEQUENCE: 56
attttggatg actgcggc                                                     18

<210> SEQ ID NO 57
<211> LENGTH: 21
<212> TYPE: DNA
<213> ORGANISM: Artificial Sequence
<220> FEATURE:
<223> OTHER INFORMATION: Chemically synthesized

<400> SEQUENCE: 57
ctttaggagc tgctgtcgat a                                                 21

<210> SEQ ID NO 58
<211> LENGTH: 21
<212> TYPE: DNA
<213> ORGANISM: Artificial Sequence
<220> FEATURE:
<223> OTHER INFORMATION: Chemically synthesized

<400> SEQUENCE: 58
gctcctacct cttccaagca g                                                 21

<210> SEQ ID NO 59
<211> LENGTH: 19
<212> TYPE: DNA
<213> ORGANISM: Artificial Sequence
<220> FEATURE:
<223> OTHER INFORMATION: Chemically synthesized

```
<400> SEQUENCE: 59
acaaaacaca gcccccagc                                                19

<210> SEQ ID NO 60
<211> LENGTH: 24
<212> TYPE: DNA
<213> ORGANISM: Artificial Sequence
<220> FEATURE:
<223> OTHER INFORMATION: Chemically synthesized

<400> SEQUENCE: 60
tggtgtgaat gtcagtgtga atgc                                          24

<210> SEQ ID NO 61
<211> LENGTH: 22
<212> TYPE: DNA
<213> ORGANISM: Artificial Sequence
<220> FEATURE:
<223> OTHER INFORMATION: Chemically synthesized

<400> SEQUENCE: 61
gcaagttgaa ggaagcagca gg                                            22

<210> SEQ ID NO 62
<211> LENGTH: 21
<212> TYPE: DNA
<213> ORGANISM: Artificial Sequence
<220> FEATURE:
<223> OTHER INFORMATION: Chemically synthesized

<400> SEQUENCE: 62
tgatcacgaa ggtggttttc c                                             21

<210> SEQ ID NO 63
<211> LENGTH: 19
<212> TYPE: DNA
<213> ORGANISM: Artificial Sequence
<220> FEATURE:
<223> OTHER INFORMATION: Chemically synthesized

<400> SEQUENCE: 63
gcacatccgg agtgcaatg                                                19
```

U1 SNRNP REGULATES GENE EXPRESSION AND MODULATES ONCOGENICITY

CROSS-REFERENCE TO RELATED APPLICATION

This application claims priority to U.S. Provisional Application Ser. No. 61/668,168, filed Jul. 5, 2012, the content of which is incorporated by reference herein in its entirety.

BACKGROUND OF THE INVENTION

Messenger RNAs in eukaryotic cells are produced from precursor transcripts (pre-mRNAs) by post-transcriptional processing. In metazoans, two processing reactions are particularly extensive and contribute most significantly to mRNA transcriptome diversity—splicing of introns and alternate cleavage and polyadenylation (Di Giammartino et al., 2011, Mol Cell 43:853-866; Hartmann and Valcarcel, 2009, Curr Opin Cell Biol 21:377-386; Wang et al., 2008, Nature 456:470-476). Splicing is performed by a spliceosome that assembles on each intron and is comprised predominantly of small nuclear RNPs (snRNPs), U1, U2, U4, U5 and U6 snRNPs, in equal stoichiometry (Nilsen, 2003, Bioessays 25(12):1147-1149; Wahl et al., 2009, Cell 136:701-718). U1 snRNP (U1) plays an essential role in defining the 5' splice site (ss) by RNA:RNA base pairing via U1 snRNA's 5' nine nucleotide (nt) sequence. Using antisense morpholino oligonucleotide complementary to U1 snRNA's 5' end (U1 AMO) that interferes with U1 snRNP's function in human cells, accumulation of introns in many transcripts was observed, as expected for splicing inhibition (Kaida et al., 2010, Nature 468, 664-668). However, in addition, the majority of pre-mRNAs terminated prematurely from cryptic PASs in introns, typically within a short distance from the transcription start site (TSS). These findings indicated that nascent transcripts are vulnerable to premature cleavage and polyadenylation (PCPA) and that U1 has a critical function in protecting pre-mRNA from this potentially destructive process. It was further showed that PCPA suppression is a separate, splicing-independent and U1-specific function, as it did not occur when splicing was inhibited with U2 snRNA AMO or the splicing inhibitor, spliceostatin A (SSA) (Kaida et al., 2007, Nat Chem Biol 3:576-583).

These observations were made by transcriptome profiling using partial genome tiling arrays, which provided limited information. The present invention addresses these issues of limited information and meets the need in the art for comprehensively assessing the role of U1 snRNP.

SUMMARY OF THE INVENTION

The invention provides a method of modulating expression of a gene in a cell. In one embodiment, the method comprises contacting a cell with an agent that regulates one or more of U1 snRNP (U1) activity or U1 level, wherein one or more of U1 activity or U1 level is associated with protecting nascent transcript, thereby modulating expression of a gene in a cell.

In one embodiment, the U1 activity is selected from the group consisting of U1 activity associated with protecting a transcript from premature termination by cleavage and polyadenylation (PCPA) at cryptic polyadenylation signals (PASs), U1 suppression of PCPA through nascent transcript, U1 activity associated with protecting intronless genes from premature cleavage and polyadenylation, U1 activity associated with increasing gene length, U1 activity associated with transcription beyond the canonical 3' end to generate new mRNA sequences, U1 activity associated with transcriptome in general, and any combination thereof.

In one embodiment, the U1 suppression of PCPA through nascent transcript is selected from the group consisting of introns, exons, 5' untranslated region, 3' untranslated region, transcriptome, and any combination thereof.

In one embodiment, a decrease in one or more of U1 activity and U1 level results in mRNAs with shorter 3' untranslated regions.

In one embodiment, a decrease in one or more of U1 activity and U1 level results in alternatively spliced isoforms resulting from usage of more proximal alternative polyadenylation (APA) sites.

In one embodiment, a decrease in one or more of U1 activity and U1 level results in transcript shortening thereby removing a regulatory element from the transcript.

In one embodiment, the regulatory element is selected from the group consisting of an RNA binding domain, a protein binding domain, a microRNA-binding site, an hnRNP protein-binding site, and any combination thereof.

In one embodiment, the shortened transcript results in increased expression of the gene.

In one embodiment, an increase in one or more of U1 activity and U1 level results in transcript lengthening thereby preventing the removal of a regulatory element from the transcript.

In one embodiment, the regulatory element is selected from the group consisting of an RNA binding domain, a protein binding domain, a microRNA-binding site, an hnRNP protein-binding site, and any combination thereof.

In one embodiment, the lengthened transcript results in decreased expression of the gene.

In one embodiment, the agent that regulates one or more of U1 activity and U1 level activity is selected from the group consisting of a U1 agonist, a U1 antagonist, and any combination thereof.

The invention provides a method of modulating telescripting in a cell wherein telescripting allows for nascent transcripts to extend thereby determining one or more of mRNA length and isoform expression, the method comprising regulating one or more of U1 snRNP (U1) activity or U1 level in the cell, wherein one or more of U1 activity or U1 level is associated with protecting nascent transcript.

The invention provides a method of modulating telescripting in a cell wherein telescripting allows for nascent transcripts to extend thereby determining one or more of mRNA length and isoform expression, the method comprising regulating relative amounts of nascent transcripts with one or more of U1 activity or U1 level in the cell.

The invention provides a method of modulating cellular phenotype of a cell, the method comprising contacting a cell with an agent that regulates one or more of U1 snRNP (U1) activity or U1 level, wherein one or more of U1 activity or U1 level is associated with protecting nascent transcript, thereby modulating cellular phenotype of the cell.

In one embodiment, the cellular phenotype is selected from the group consisting of cell proliferation, activation, differentiation, oncogenicity, and any combination thereof, activation of immune cells, activation of neurons, growth of stem cells, oncogenicity, and any combination thereof.

In one embodiment, the cellular phenotype is selected from the group consisting activation of immune cells, activation of neurons, growth of stem cells, oncogenicity of a cancer cell, and any combination thereof.

In one embodiment, increasing one or more of U1 activity and U1 level attenuates oncogenicity of the cell.

In one embodiment, increasing one or more of U1 activity and U1 level inhibits mRNA shortening in activated neurons.

The invention provides a method of treating a disease or disorder in a subject. In one embodiment, the method comprises administering an agent that regulates one or more of U1 snRNP (U1) activity or U1 level, wherein one or more of U1 activity or U1 level is associated with protecting nascent transcript, thereby treating the disease or disorder in the subject.

In one embodiment, the disease or disorder is selected from the group consisting of cancer, autoimmune disease, inflammation, infection, neurological, and any combination thereof.

In one embodiment, the agent is a U1 agonist, further wherein the U1 agonist results in transcript lengthening thereby preventing the removal of a regulatory element from the transcript.

In one embodiment, the regulatory element is selected from the group consisting of an RNA binding domain, a protein binding domain, a microRNA-binding site, an hnRNP protein-binding site, and any combination thereof.

In one embodiment, the lengthened transcript results in decreased expression of the gene. In one embodiment, the gene is a proto-oncogene.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A through FIG. 1C, depicts the results of experiments demonstrating that HIDE-seq identifies genome-wide transcriptome changes. (FIG. 1A) Unsubtracted and subtracted libraries prepared in both directions (Control-U1; U1-Control) are shown (left gel) along with possible products of suppression PCR. Differentially expressed sequences as well as common sequences are shown. Nested PCR (right gel) was performed with primers containing barcodes (hashed lines) and 454 adaptors A and B. (FIG. 1B) Randomly sampled reads with greater than 90% coverage and 90% identity were plotted against affected genes for HeLa, NIH/3T3 and S2 from individual or combined subtractions. (FIG. 1C) HIDE-seq reads are above [U1-Control (UP)] and below [Control-U1 (DOWN)] gene structures in black (block=exon, thin block=UTR, horizontal line=intron). Spliced reads are connected by dashed lines whereas immediately adjacent reads separated by RsaI, HaeIII, and AluI sites are not. Log 2 fold changes from GTA of U1 AMO or SSA-treated HeLa cells normalized to controls (bottom panels). Arrows point to inferred PCPA sites.

FIG. 2A through FIG. 2D, depicts the results of experiments illustrating that transcriptome profiles show a conserved function of U1 snRNP in PCPA suppression. (FIG. 2A) Localization of the HIDE-seq profiles are shown (location indicated by solid arrows) with respect to the genome for S2, NIH/3T3, and HeLa. Distance (nt) is relative to the upstream 5' splice site with the PAS hexamer likely used (FIG. 2B) Illustrations of patterns observed (depicted above each column) after U1 AMO with the percentage of each category reported for Drosophila (15), mouse (15) and human at three doses (15, 1.0, 0.25) compared to the total number of affected genes in parenthesis. Introns=solid boxes; exons=empty boxes. (FIG. 2C) Individual examples of patterns described in FIG. 2B are shown with brackets indicating results from more than one concentration. Solid arrows indicate reads ending in poly(A) tails; open arrows are inferred PCPA; triangles are documented PASs. See also FIGS. 12-13. (FIG. 2D) Using reads with poly(A) tails terminating in introns (FIGS. 9-12; Table 2), the distribution of distances of PCPA relative to the TSS are plotted for Drosophila and mouse (top), and human at high and low U1 AMO (bottom).

FIG. 3A and FIG. 3B, depicts the results of experiments demonstrating that moderate U1 reduction-induced PCPA regulates expression of short isoforms. (FIG. 3A) HIDE-seq profile for GABPB1 at high and low U1 AMO are above diagrams of long and short isoforms. RT-qPCR of short and long isoforms was performed on cDNA from cells transfected with a range of U1 AMO concentrations using a common forward and different reverse primers as indicated (arrows). Dotted boxes indicate region of transcript probed. Ratios of short to long are reported above histograms. (FIG. 3B) UBAP2L was probed by RT-PCR for short (due to 3' exon switching) and long isoforms (gels) and by RT-qPCR on cDNA from cells treated with various AMOs. Triangle=3' splice site and PAS AMOs, solid arrows=poly(A) reads; open arrows=inferred PCPA.

FIG. 4A through FIG. 4E, depicts the results of experiments illustrating that U1 bound outside the 5' splice site is required to suppress PASs>1 kb away. (FIG. 4A) Distribution of the $\log_{10}$ distance at which PCPA occurred was measured in each organism from the start of the poly(A) tail back to the upstream 5' splice site or downstream to the 3' splice site. See also FIGS. 9-11 and Table 2. (FIG. 4B) Arrows indicate multiple PCPA sites per gene. (FIG. 4C) HeLa cells were transfected with WT NR3C1 mini-gene (lane 1) or one containing a 5' splice site mutation (lanes 2-12) and increasing amounts of mutant U1 that base-pairs to one of four locations along the pre-mRNA. PCPA in the intron was detected by 3'RACE with RT-PCR of exon 2 serving as the loading control. Percent suppression (PCPA to exon 2 ratio) was normalized to lane 2. (FIG. 4D) Control or U1 AMO were transfected along with WT NR3C1 mini-gene (lanes 1 & 2) or NR3C1 in which the PAS1 [385 nt] sequence in the intron was duplicated (PAS2) and placed 1295 nt downstream of the 5' splice site. Mini-genes in which the 5' splice site (lanes 3 & 4), PAS1 (lanes 5 & 6) or both (lanes 7 & 8) were mutated are indicated. 3'RACE was performed as in (FIG. 4C). (FIG. 4E) Control, U1 or an AMO to the 5' splice site of the endogenous BASP1 gene were transfected as indicated. PCPA at the PAS 3.5 kb downstream of exon 1 was measured by 3' RACE. RT-PCR on intronic sequences upstream (IR1) and downstream (IR2) of the PAS is shown.

FIG. 5A and FIG. 5B, depicts the results of experiments illustrating that moderate U1 reduction recapitulates isoform switching upon neuronal activation. Rat PC12 (FIG. 5A) and mouse MN-1 (FIG. 5B) neurons were stimulated with forskolin or forskolin/KCl for 3 hrs or separately transfected with control AMO or increasing amounts of U1 AMO. RT-PCR detecting short and long forms of Homer-1/Vesl-1 and Dab-1 are shown with histograms depicting the ratio of S/L. Grey dotted boxes indicate the region of transcript probed, arrows show primer locations, and G6PDH is a loading control.

FIG. 6A and FIG. 6B, depicts the results of experiments demonstrating that U1 ratio to pre-mRNA determines immediate-early polyadenylation switch.

(FIG. 6A) PC12 were activated with forskolin/KCl or mock treated (DMSO) for the indicated times and labeled with $^3$H-uridine for 30 min prior to collection. Ratios of nascent transcripts to total RNA were determined by scintillation and normalized to amounts of unlabeled total RNA. DMSO controls represent the average of 6 time points per experiment and activated values represent the average of two independent experiments (3 hr time point measured once). U1 snRNA was measured by RT-qPCR at the same time points. (FIG. 6B) PC12 cells were transfected overnight (24 hrs) to over-express U1 (or empty vector) and activated with forskolin/KCl. Homer-1 isoforms were probed by RT-PCR 3 hrs after activation, as in FIG. 5A. Histograms depict the ratio of S/L forms from biological repeat experiments with percent U1 over-expression reported below.

FIG. 8, comprising (FIG. 8A) Venn diagram of overlap in intron accumulation between HIDE-seq data and tiling arrays for human chr 5, 7 and 16 (see methods discussed elsewhere herein). (FIG. 8B) RT-PCR validation of predicted intron retention for POLR1C on HeLa cells treated with AMOs to the indicated major (U1 and U2) and minor (U12 and U6atac) snRNPs. (FIG. 8C) (left) HIDE-seq prediction of exon skipping in RAN was validated by RT-PCR on cDNA obtained from HeLa cells treated with control, U1, U2, U12, and U6atac AMOs. Primers were located in exons 3 and 5 (box=exon, line=intron; lane 1=size marker; the expected products are illustrated on the right and their sizes are listed next to the ladder). (upper right) PAM is another example of exon skipping in U1 AMO-treated cells detected by HIDE-seq. The position and length of the skipped exon is indicated. (lower right) APOA1BP shows that both 5' and 3' splice site positions are altered in U1 AMO-treated cells. Lengths of the differential sequences (underlined) are compared to the total length of reads in the opposite subtraction (arrow). (FIG. 8D) Intron retention (arrows) for CG5168 and Gint3 predicted by HIDE-seq for U1 AMO in Drosophila was validated by RT-PCR on cDNA from S2 cells treated with Control, U1, U2, U12 and U6atac AMOs. (FIG. 8E) Examples of PCPA identified by HIDE-seq were validated by 3' RACE on the same AMO-treated samples in (FIG. 8B) with forward primers in exon 3 of Chic and exon 1 of Ten-m genes. PCPA is premature cleavage and polyadenylation in an intron, PA2/PA1 are polyadenylation sites in the 3' UTR, and * indicates a non-specific PCR product. The expected sizes of products from PCPA are listed above intronic reads.

FIG. 9 depicts the attributes of PCPA in human (HeLa). Poly(A) tails were detected in intron-containing reads arc listed for 71 definitive PCPA reads in human. Gene names and the genomic coordinates of PCPA are listed to the left. Putative PAS hexamers were identified in the sequences. Gene lengths (Gene L), distances of PCPA from the transcription start site (TSS), from the nearest TSS (aTSS), the intron number (Int #) in which PCPA occurs and its length (Int L), the distance between PCPA and the 5' splice site (5'ss), or the 3' splice site (3'ss) are all listed. Calculations of the median, mean and standard deviation for each are shown in Table 2. The distance of an EST relative to PCPA, the identifier of alternate isoforms reported in UCSC, Aceview, or EST databases, and the tissue(s) in which they were found are also listed.

FIG. 10 depicts the attributes of PCPA in mouse (3T3). Genomic Poly(A) tails were detected in added intron-containing reads for 70 definitive PCPA reads in mouse. Putative PAS hexamers were identified in the sequences. Gene lengths (Gene L), distances of PCPA from the transcription start site (TSS), from the nearest TSS (aTSS), the intron number (Int #) in which PCPA occurs and its length (Int L), the distance between PCPA and the 5' splice site, or the 3' splice site are all listed. Calculations of the median, mean and standard deviation for each are shown in Table 2.

FIG. 11 depicts the attributes of PCPA in Drosophila (S2). Poly(A) tails were detected in intron-containing reads for 59 definitive PCPA reads in Drosophila. Putative PAS hexamers were identified in the sequences. Gene lengths (Gene L), distances of PCPA from the transcription start site (TSS), from the nearest TSS (aTSS), the intron number (Int #) in which PCPA occurs and its length (Int L), the distance between PCPA and the 5' splice site or the 3' splice site are all listed. Calculations of the median, mean and standard deviation for each are shown in Table 2.

FIG. 12 depicts the alignment of PCPA in human (HeLa: 1.0 and 0.25 nmol U1 AMO). Poly(A) tails were detected in intron-containing reads for 50 definitive PCPA reads in human at the combined low doses. Putative PAS hexamers were identified in the sequences. Gene lengths (Gene L), distances of PCPA from the transcription start site (TSS), the intron number (Int #) in which PCPA occurs, the class of PCPA, alternate shorter isoforms that coincide with PCPA from databases and the tissues in which they were reported are all listed. Abbreviations for tissues are as follows: Adeno Cx: adenocarcinoma; AnaOligo: anaplastic oligodendroglioma; BM: bone marrow; BR: breast; B: brain; Cx: carcinoma; CE: cerebellum; CO: colon; E: eye; ESC: embryonic stem cells; H: heart; HYP: hypothalamus; K: kidney; L: lung; LCC: large cell carcinoma; NB: neuroblastoma; 0: ovary; P: pancreas; PGCT: pooled germ cell tumors; PL: placenta; PR: prostate; RB: retinoblastoma; S: stomach; T: testis; U: uterus; V: liver. Calculations of the median, mean and standard deviation for each are shown in Table 2.

FIG. 13A and FIG. 13B, depicts the results of experiments demonstrating that 3'UTR shortening is found in U1 AMO treated cells. (FIG. 13A) HIDE-seq profiles of 3'UTR's are shown for genes in HeLa cells treated with three doses of U1 AMO that exhibited shortening. (FIG. 13B) Additional examples as in (FIG. 13A) that also showed tandem 3'UTR shortening in activated T cells.

FIG. 16A through FIG. 16E, depicts the results of experiments demonstrating that U1 overexpression decreases oncogenicity of HeLa cells in vitro. (FIG. 16A) HeLa cells were transfected with the control (empty vector) or U1 snRNA expression plasmids. Cell proliferation was measured by the MTT Assay every 24 hours. (FIG. 16B, FIG. 16C) Cell migration and invasion activity were measured after 24 hours. (FIG. 16D, FIG. 16E) Migrating and invading cells were stained 24 hours after incubation and visualized by phase-contrast (10× magnification) microscopy.

FIG. 17A through FIG. 17E, depicts the results of experiments demonstrating that moderate U1 decrease enhances oncogenicity of HeLa cells in vitro. (FIG. 17A) HeLa cells were transfected with the indicated amounts of U1 AMO or control AMO. Cell proliferation was measured by the Cell Titer-Glo Luminescent Cell Viability Assay every 24 hours. (FIG. 17B, FIG. 17C) Cell migration and invasion activity were measured 24 hours after transfection. $1.5 \times 10^5$ and $2.5 \times 10^5$ cells were cultured for the migration and invasion assays, respectively. (FIG. 17D, FIG. 17E) Migrating and invading cells were stained 24 hours after incubation and visualized by phase-contrast (10× magnification) microscopy.

FIG. 19A and FIG. 19B, depicts the results of experiments demonstrating that U1 snRNP protects intronless genes from premature cleavage and polyadenylation, and its level modulates mRNA length of intronless genes bi-directionally. RNA-seq maps of representative examples showing the entire intronless genes with dotted boxes indicating switch towards longer transcripts by U1 overexpression (FIG. 19A) and shorter transcripts by U1 AMO (FIG. 19B).

FIG. 23A through FIG. 23C, depicts a summary and analysis of UTRend identification of genes with 3'UTR length change. (FIG. 23A) Venn diagrams depict the number of genes affected by shortening versus lengthening in U1 AMO (top) and U1 over-expression (bottom) samples. (FIG. 23B) U1 levels affect mRNA length change in highly transcribed genes with longer 3'UTRs. The length of 3'UTRs in affected vs. background (all expressed HeLa genes or a randomly selected dataset of equal number of genes) is shown for shortened (top) and lengthened (bottom) genes. A significantly longer UTR (Wilcoxon rank sum test, p-value $<2.2 \times 10-16$, respectively) is observed for the affected genes compared to the total or a randomly selected dataset. (FIG. 23C) Expression levels (RPKM values) were evaluated as in FIG. 23B. A significantly higher expression (Wilcoxon rank sum test, p-value $<2.2 \times 10-16$) is observed for the affected genes compared to the total or a randomly selected dataset.

FIG. 24A through FIG. 24C, depicts the results of experiments demonstrating that moderate decreases in U2 does not promote oncogenic phenotype in HeLa. (FIG. 24A) migration (FIG. 24B) invasion assays and (FIG. 24C) phase-contrast imaging 24 hrs following transfection with control and U2 AMO (0.05-1 nmole) were performed as described in FIG. 17.

DETAILED DESCRIPTION OF THE INVENTION

Figure 1:
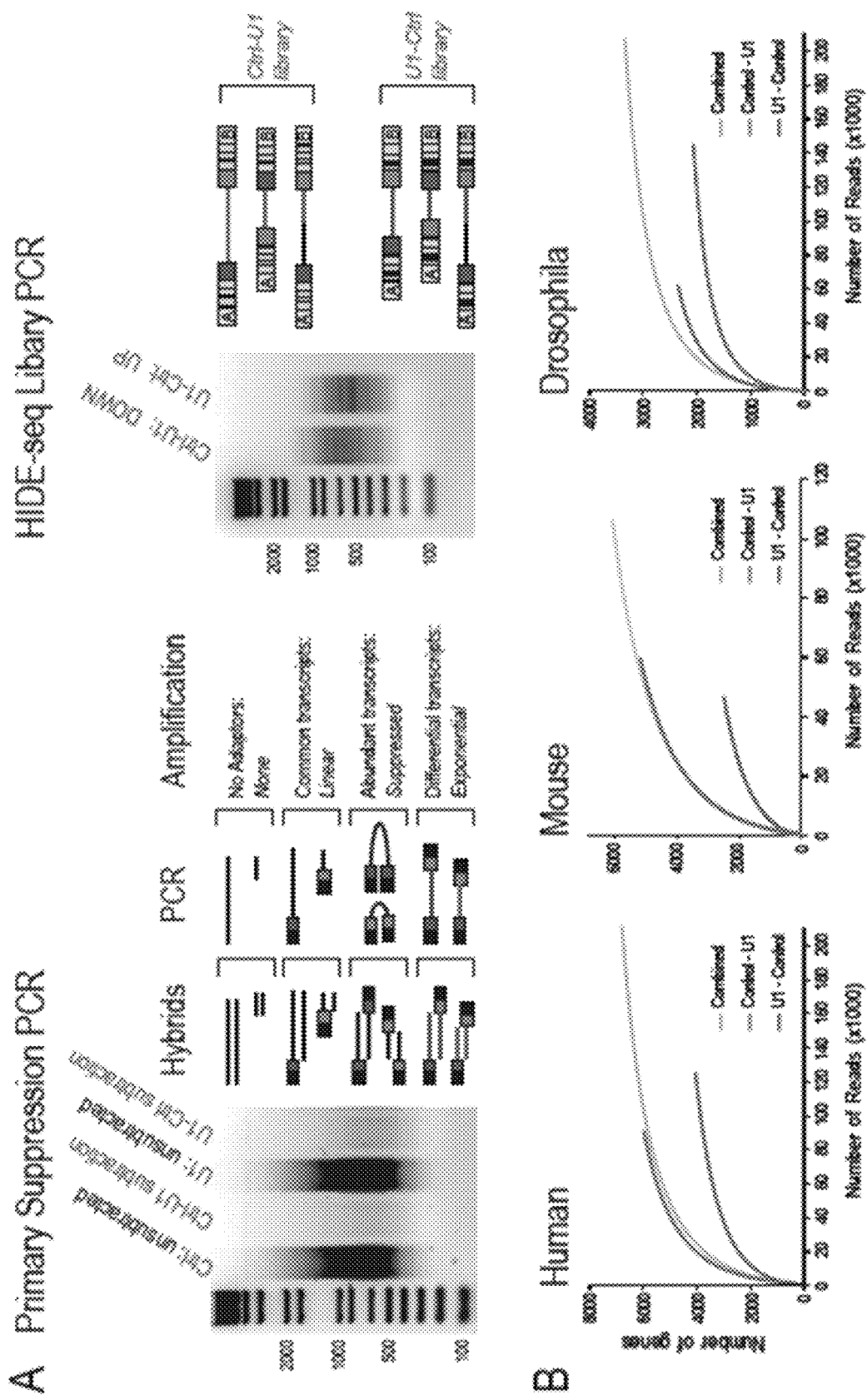
FIG. 1, comprising

The invention is based, in part, on the discovery that U1 snRNP (U1) is involved in a global gene expression regulation mechanism. For example, the results presented herein demonstrate the successful mapping of U1 premature cleavage and polyadenylation sites (PCPA) in divergent organisms. In addition, the present invention relates to the discovery that U1, in addition to its splicing role, protects pre-mRNAs from drastic premature termination by cleavage and polyadenylation at cryptic polyadenylation signals (PASs). This process is referred herein as telescripting, which ensures transcriptome integrity and regulates mRNA length. In some instances, telescripting contributes to nascent transcripts extending over large distances. Accordingly, telescripting provides a novel global gene expression regulation mechanism.

U1 can also regulate gene expression in both genes comprising introns or intronless genes. In one embodiment, U1 protects intronless genes from premature cleavage and polyadenylation. In another embodiment, U1 modulates mRNA length of intronless genes bi-directionally. In yet another embodiment, U1 increases gene length. In one embodiment, U1 allows for transcription beyond the canonical 3' end to generate new mRNA sequences.

The invention is also partly based on the discovery that U1 over-expression lengthened numerous 3'UTRs in cancer cells and thereby demonstrating that telescripting as a target for moderating tumorigenesis. This is because 3'UTR shortening often removes microRNA (miRNA) binding sites enriched in this part of mRNAs, resulting in loss of miRNA regulation. This typically alleviates the miRNA-mediated translation repression often resulting in strong increase in the amount of protein produced from the shortened mRNA, including proto-oncogenes.

Accordingly, the invention provides for compositions and methods of regulating all aspects of gene expression. In one embodiment, the invention provides for compositions and methods for regulating U1 as a means for regulating gene expression. In one embodiment, a decrease in U1 decreases 3'UTR. In one embodiment, a decrease in U1 promotes gene expression. In one embodiment, a decrease in U1 promotes gene expression due to elimination of regulatory targets in the 3' UTR. An example of a regulatory target includes microRNA (miRNA) binding sites and other mRNA regulatory elements.

In another embodiment, an increase in U1 increases 3'UTR. In another embodiment, an increase in U1 inhibits gene expression. In one embodiment, an increase in U1 inhibits gene expression due to prevention of the elimination of regulatory targets in the 3' UTR. An example of a regulatory target includes microRNA (miRNA) binding sites and other mRNA regulatory elements.

In one embodiment, an increase in U1 attenuates cell migration and invasiveness of a cancer cell, while its decrease dose-dependently enhances cell migration and invasiveness. This is because in some instances, many of the 3'UTR length changes recapitulates cancer-causing miRNA target deregulation in oncogenes.

In one embodiment, PCPA suppression can be modulated by decreasing available U1 over a large range without splicing being compromised. Therefore PCPA suppression provides a new and global gene expression regulation mechanism through modulating U1 levels.

Accordingly, the invention provides a method of modulating U1 for therapeutic applications including but are not limited to 1) decreasing levels of U1 to stimulate an immune response (e.g., vaccine adjuvant) or neuronal repair; 2) increasing levels of U1 (e.g., via small molecule activators or U1 overexpression) to decrease transcription rates of genes associated with cancer thereby treating cancer.

In one embodiment, the invention provides a method of decreasing U1 levels with, for example, an antisense nucleic acid to enhance oncogenic cell characteristics, including cell migration and invasiveness in vitro. Without wishing to be bound by any particular theory, it is believed that decrease levels of U1 promotes mRNA shortening, removing micro RNA binding sites in the 3' untranslated region thereby resulting in loss of miRNA regulation, which in turn de-represses protein expression from the shortened mRNAs, which thereby produces more protein, including oncogenic, anti-apoptotic proteins, and the like. In another embodiment, the antagonists of U1 can decrease and/or inhibit U1 with respect to splicing and protecting pre-mRNAs from drastic premature termination by cleavage and polyadenylation at cryptic polyadenylation signals.

In another embodiment, the invention provides a method of increasing U1 levels or activity in order to attenuate oncogenicity. Accordingly, the invention also provides agonists of U1 that increase the level and/or activity of U1 with respect to splicing and protecting pre-mRNAs from drastic premature termination by cleavage and polyadenylation at cryptic polyadenylation signals. In the context of cancer, a U1 agonist can increase levels of U1 in order to prevent mRNA shortening, and thereby prevent the removal of regulatory targets in the 3' UTR (e.g., micro RNA binding sites). A result of 3'UTR lengthening using an U1 agonist allows for regulation of the gene by way of the regulatory targets in the 3' UTR. In one embodiment, lengthening of the 3'UTR results in repressing protein expression from the lengthen mRNAs, which thereby produces less protein, including oncogenic, anti-apoptotic proteins, and the like.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject. Agents can comprise, for example, drugs, metabolites, intermediates, cofactors, transition state analogs, ions, metals, toxins and natural and synthetic polymers (e.g., proteins, peptides, nucleic acids, polysaccharides, glycoproteins, hormones, receptors and cell surfaces such as cell walls and cell membranes. Agents may also comprise alcohols, alkyl halides, amines, amides, esters, aldehydes, ethers and other classes of organic agents.

As used herein a "U1 agonist" refers to any agent that mimics, activates, stimulates, potentiates or increases the biological activity of U1. A U1 agonist may be U1 or a fragment thereof; an agent that mimics U1 (such as a small molecule); an agent that increases or enhances the expression of U1; an agent that enhances the binding of U1 to nucleic acid or its binding partner; and the like.

As used herein a "U1 antagonist" refers to any agent that attenuates, inhibits, opposes, counteracts, or decreases the biological activity of U1. A U1 antagonist may be an agent that inhibits or neutralizes U1 activity (including, without limitation, small molecules and anti-U1 antibodies); an agent that inhibits or decreases the expression of U1 (including, without limitation, an antisense molecule, an RNAi molecule, and the like); an agent that prevents the binding of U1 to nucleic acid or a binding partner of U1.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

"Antisense" refers particularly to the nucleic acid sequence of the non-coding strand of a double stranded DNA molecule encoding a polypeptide, or to a sequence which is substantially homologous to the non-coding strand. As defined herein, an antisense sequence is complementary to the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

The term "expression" as used herein is defined as the transcription and/or translation of a particular nucleotide sequence driven by its promoter.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

The term "inhibit," as used herein, means to suppress or block an activity or function by at least about ten percent relative to a control value. Preferably, the activity is suppressed or blocked by 50% compared to a control value, more preferably by 75%, and even more preferably by 95%.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

As used herein, the term "modulate" is meant to refer to any change in biological state, i.e. increasing, decreasing, and the like. For example, the term "modulate" refers to the ability to regulate positively or negatively the expression or activity of U1, including but not limited to transcription of U1 mRNA, stability of U1 mRNA, translation of U1 mRNA, stability of U1 polypeptide, U1 post-translational modifications, or any combination thereof. Further, the term modulate can be used to refer to an increase, decrease, masking, altering, overriding or restoring of activity, including but not limited to, U1 activity associated with its splicing role and role with protecting pre-mRNAs from drastic premature termination by cleavage and polyadenylation (PCPA) at cryptic polyadenylation signals (PASs) in introns, U1 activity associated with protecting intronless genes from premature cleavage and polyadenylation, U1 activity associated with increasing gene length, U1 activity associated with transcription beyond the canonical 3'end to generate new mRNA sequences, and U1 activity associated with transcriptome in general.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

"Constitutive" expression is a state in which a gene product is produced in a living cell under most or all physiological conditions of the cell.

"Inducible" expression is a state in which a gene product is produced in a living cell in response to the presence of a signal in the cell.

A "recombinant polypeptide" is one, which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

As used herein, to "treat" means reducing the frequency with which symptoms of the disease are experienced by a patient, or altering the natural history and/or progression of the disease in a patient.

A "therapeutic" treatment is a treatment administered to a subject who exhibits signs of pathology for the purpose of diminishing or eliminating those signs.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention provides compositions and methods for regulating gene expression. In one embodiment, the compositions and methods of the invention are directed to a process referred herein as telescripting. In one embodiment, telescripting ensures transcriptome integrity and regulates mRNA length. In some instances, telescripting contributes to nascent transcripts extending over large distances. Accordingly, telescripting provides a novel global gene expression regulation mechanism.

In one embodiment, the invention provides compositions and methods for regulating U1 activity associated with its splicing role as well as its role in protecting pre-mRNAs from drastic premature termination by cleavage and polyadenylation (PCPA) at cryptic polyadenylation signals (PASs) in introns.

In another embodiment, the invention provides compositions and methods for regulating U1, wherein U1 regulates gene expression in both genes comprising introns or intronless genes. In one embodiment, U1 protects intronless genes from premature cleavage and polyadenylation. In another embodiment, U1 modulates mRNA length of intronless genes bi-directionally. In yet another embodiment, U1 increases gene length. In one embodiment, U1 allows for transcription beyond the canonical 3'end to generate new mRNA sequences.

In one embodiment, the invention provides for compositions and methods of regulating all aspects of gene expression. In one embodiment, the invention provides for compositions and methods for regulating U1 as a means for regulating gene expression. In one embodiment, an increase in U1 lengthens numerous 3'UTRs. In one embodiment, lengthening 3'UTRs prevents the removal of regulatory binding sites (e.g., miRNA binding sites) enriched in this part of mRNAs. In some instances, lengthening of 3'UTRs result in increased miRNA regulation thereby decreasing expression. Therefore, in some instances, an increase in U1 inhibits gene expression.

In one embodiment, a decrease in U1 shortens numerous 3'UTRs. In one embodiment, shortening of 3'UTRs removes regulatory binding sites (e.g., miRNA binding sites) enriched in this part of mRNAs. In some instances, shortening of 3'UTRs result in decreased miRNA regulation thereby increasing expression. Therefore, in some instances, a decrease in U1 increases gene expression.

In one embodiment, the invention provides a method of reducing expression of a gene in a cell comprising increasing U1 in the cell. In another embodiment, the invention provides a method of reducing protein production in a cell comprising increasing U1 in the cell. In another embodiment, the invention provides a method of reducing output in a cell of an mRNA produced by a gene in the cell comprising increasing U1 in the cell.

In one embodiment, the invention provides a method of increasing expression of a gene in a cell comprising decreasing U1 in the cell. In another embodiment, the invention provides a method of increasing protein production in a cell comprising decreasing U1 in the cell. In another embodiment, the invention provides a method of increasing output in a cell of an mRNA produced by a gene in the cell comprising increasing U1 in the cell.

In one embodiment, decreasing U1 levels and/or activity results in enhancing oncogenic cell characteristics in a cell including but is not limited to cell migration and invasiveness. In another embodiment, increasing or overexpressing U1 attenuates oncogenicity. Without wishing to be bound by any particular theory, it is believed that a decrease in U1 levels and/or activity promotes mRNA shortening, which removes miRNA binding sites in the 3' untranslated region of a pre-mRNA molecule, thereby de-repressing protein expression from the shortened mRNAs and therefore producing more protein, including oncogenic, anti-apoptotic proteins, and the like.

Accordingly, the invention provides compositions and methods for targeting and regulating U1 and its functional equivalents in a cell to regulate protein expression. In one embodiment, regulating U1 and its functional equivalents in a cell allows for the regulation of a cellular characteristic. In some instances, the cellular characteristic that is being regulated through the regulation of U1 is the oncogenic characteristic of the cell. For example, increasing or activating U1 in a cell results in attenuating oncogenicity of a cell. Alternatively, decreasing or inhibiting U1 in a cell results in an increase in oncogenicity of a cell.

The invention should not be limited to only regulating oncogenicity of a cell. Rather, the invention allows for regulating any phenotype of a cell wherein the phenotype is associated with expression of a particular protein or splicing variant. That is, regulating U1 allows for the regulation of the expression of a desired protein or splicing variant. For example, when it is desirable to increase the expression of a particular protein, U1 can be inhibited so that the pre-mRNA associated with the desired protein is shorten to the extent that micro RNA binding sites in the 3' untranslated region is removed, thereby de-repressing expression from the shortened mRNAs which in turn produces more protein. Alternatively, when it is desirable to decrease the expression of a particular protein, U1 can be activated or increased so that the pre-mRNA associated with the desired protein is not shorten so that micro RNA binding sites in the 3' untranslated region are present, thereby repressing expression from the mRNAs which in turn produces less protein.

Compositions

The present invention comprises any agent that mimics, activates, stimulates, potentiates or increases the biological activity of U1 snRNP (U1) that can be used as a U1 agonist. The invention also comprises any agent that inhibits, opposes, counteracts, or decreases the biological activity of U1 that can be used as a U1 antagonist.

U1 agonists of the invention include but are not limited to purified or recombinant nucleic acids that encode U1 proteins or fragments thereof; purified or recombinant U1 polypeptides or fragments thereof; or other agents that mimic, activate, stimulate, potentiate or increase the biological activity of U1. Examples of U1 agonist include, without limitation, agents that increase U1 mRNA or protein expression; agents that increase interaction between U1 and nucleic acid, and other agents that are identified by any of the screening methods described herein or in the future.

In one embodiment, the invention comprises a composition for attenuating oncogenicity. For example, a U1 agonist of the invention can be used to increase or overexpress U1 wherein U1 is able to prevent the shortening of the pre-mRNA and/or promote lengthening of the pre-mRNA. In some instances, a U1 agonist of the invention can be used to increase or overexpress U1 wherein U1 is able to protect pre-mRNAs from drastic premature termination by cleavage and polyadenylation at cryptic polyadenylation signals and thereby preventing the removal of micro RNA binding sites in the 3' untranslated region, which can result in repressing protein expression of an oncogenic protein. In another embodiment, the U1 agonist can regulate both intron and intronless genes.

In one embodiment, the invention comprises a composition for inhibiting U1 (e.g., U1 antagonists). For example, a U1 antagonist of the invention can be used to inactivate or decrease expression of U1 wherein the inactivation or decreased expression of U1 shortens the length of the pre-mRNA. In some instances, shortening of the pre-mRNA removes regulatory binding sites (e.g., miRNA) in the pre-mRNA, which can result in increased expression. In one embodiment, shortening of the pre-mRNA removes regulatory binding sites (e.g., miRNA) in the pre-mRNA, which can result in de-repressing protein expression of an oncogenic protein. In another embodiment, the U1 antagonist can regulate both intron and intronless genes.

U1 antagonists of the invention include but are not limited to agents that inactivate, inhibit, sequester or decrease the biological activity of U1. Example of U1 antagonist include, without limitation, a small interfering RNA (siRNA), a microRNA, an antisense nucleic acid, a ribozyme, an expression vector encoding a transdominant negative mutant, an intracellular antibody, a peptide and a small molecule.

An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002 Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that certain exemplary sequences disclosed herein as DNA sequences capable of directing the transcription of the siRNA polynucleotides are also intended to describe the corresponding RNA sequences and their complements, given the well-established principles of complementary nucleotide base-pairing.

In another embodiment, the modulating sequence is an antisense nucleic acid molecule. In some instances, the antisense nucleic acid sequence can be expressed by a vector. For example, an antisense expressing vector can be used to transfect a mammalian cell or the mammal itself, thereby causing reduced endogenous expression of a desired regulator (e.g., U1) in the cell. However, the invention should not be construed to be limited to inhibiting expression of a regulator by transfection of cells with antisense molecules. Rather, the invention encompasses other methods known in the art for inhibiting expression or activity of a protein in the cell including, but not limited to, the use of a ribozyme, the expression of a non-functional regulator (i.e. transdominant negative mutant) and use of an intracellular antibody.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In another aspect of the invention, U1 can be inhibited by way of inactivating and/or sequestering U1. As such, inhibiting the effects of U1 can be accomplished by using a transdominant negative mutant. Alternatively an antibody specific for U1 may be used. In one embodiment, the antagonist is a protein and/or compound having the desirable property of interacting with a binding partner of U1 and thereby competing with U1. In another embodiment, the antagonist is a protein and/or compound having the desirable property of interacting with U1 and thereby sequestering U1. As will be understood by one skilled in the art, any antibody that can recognize and bind to an epitope of interest (e.g., an epitope of U1) is useful in the present invention.

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 *Proc. Nat'l. Acad. Sci. USA* 85: 2444-2448 Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Genetic Modification

The invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York).

The desired polynucleotide can be cloned into a number of types of vectors. However, the present invention should not be construed to be limited to any particular vector. Instead, the present invention should be construed to encompass a wide plethora of vectors which are readily available and/or well-known in the art. For example, a desired polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the desired polynucleotide, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Any DNA vector or delivery vehicle can be utilized to transfer the desired polynucleotide to a cell in vitro or in vivo. In the case where a non-viral delivery system is utilized, a preferred delivery vehicle is a liposome. The above-mentioned delivery systems and protocols therefore can be found in Gene Targeting Protocols, 2ed., pp 1-35 (2002) and Gene Transfer and Expression Protocols, Vol. 7, Murray ed., pp 81-89 (1991).

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Methods of Modulating U1 Activity

U1 activity can be modulated using any method disclosed herein or known to the skilled artisan. Examples of methods to enhance U1 activity include but are not limited to, increasing expression of an endogenous U1 gene, increasing expression of U1 mRNA, and enhancing the function, activity, or stability of a U1 protein. A U1 activator may therefore be a compound that increases expression of a U1 gene, increases U1 mRNA half-life, stability and/or expression, or enhances U1 protein function, activity or stability. A U1 activator may be any type of compound, including but not limited to, a polypeptide, a nucleic acid, an aptamer, a peptidometic, and a small molecule, or combinations thereof.

Examples of methods to inhibit U1 activity include but are not limited to, inhibiting expression of an endogenous U1 gene, decreasing expression of U1 mRNA, and inhibiting the function, activity, or stability of a U1 protein. A U1 inhibitor may therefore be a compound that decreases expression of a U1 gene, decreases U1 mRNA half-life, stability and/or expression, or inhibits U1 protein function, activity or stability. A U1 inhibitor may be any type of compound, including but not limited to, a polypeptide, a nucleic acid, an aptamer, a peptidometic, and a small molecule, or combinations thereof.

U1 regulation may be accomplished either directly or indirectly. For example, U1 may be directly inhibited by compounds or compositions that directly interact with U1 protein, such as antibodies. Alternatively, U1 may be inhibited indirectly by compounds or compositions that inhibit U1 downstream effectors, or upstream regulators which up-regulate U1 expression.

Decreasing expression of an endogenous U1 gene includes providing a specific inhibitor of U1 gene expression. Decreasing expression of U1 mRNA or U1 protein includes decreasing the half-life or stability of U1 mRNA or decreasing expression of U1 mRNA. Methods of decreasing expression of U1 include, but are not limited to, methods that use an siRNA, a microRNA, an antisense nucleic acid, a ribozyme, an expression vector encoding a transdominant negative mutant, a peptide, a small molecule, other specific inhibitors of U1 gene, mRNA, and protein expression, and combinations thereof.

The invention includes methods for the treatment of a U1 related disorder. Administration of a U1 inhibitor comprising one or more peptides, a small molecule, an antisense nucleic acid, a soluble receptor, an antibody, or an agent that attenuates, inhibits, opposes, counteracts, or decreases the biological activity of U1 in a method of treatment can be achieved in a number of different ways, using methods known in the art. Similarly, administration of a U1 activator comprising one or more peptides, a small molecule, or an agent that mimics, activates, stimulates, potentiates or increases the biological activity of U1 in a method of treatment can be achieved in a number of different ways, using methods known in the art.

In one embodiment, the invention includes modulating U1 for oncology applications. For example, a decrease in U1 levels leads to mRNA shortening, increase in transcription and cancer (e.g., accelerates proliferation, migration, invasiveness). Accordingly, treatment of cancer can encompass increasing U1 function using for example U1 agonists of the invention to elevate the levels or activity of U1 in order to attenuate shortening of mRNA. This is because the invention is based on the discovery that decreasing U1 levels (e.g., with an antisense morpholono oligonucleotide to U1) enhances oncogenic cell characteristics, including cell migration and invasiveness in vitro. Therefore, the invention provides for compositions and methods to overexpress U1 in order to attenuate oncogenicity.

It will be appreciated that the compounds (e.g., U1 agonist or U1 antagonist) of the invention may be administered to a subject either alone, or in conjunction with another therapeutic agent. In one embodiment, for the treatment of cancer, the compounds of the present invention may be used in combination with existing therapeutic agents used to treat cancer. In some instances, the compounds of the invention may be used in combination these therapeutic agents to enhance the antitumor effect of the therapeutic agent.

In order to evaluate potential therapeutic efficacy of the compounds of the invention in combination with the antitumor therapeutics described elsewhere herein, these combinations may be tested for antitumor activity according to methods known in the art.

In one aspect, the present invention contemplates that the compounds of the invention may be used in combination with a therapeutic agent such as an anti-tumor agent including but not limited to a chemotherapeutic agent, an anti-cell proliferation agent or any combination thereof.

The invention should not be limited to any particular chemotherapeutic agent. Rather, any chemotherapeutic agent can be linked to the antibodies of the invention. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents are so named because of their ability to add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

There are a variety of antitumor antibiotics that generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

Miscellaneous agents include chemotherapeutics such as bleomycin, hydroxyurea, L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas exotoxin*, *Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

In some embodiments, an effective amount of a compound of the invention and a therapeutic agent is a synergistic amount. As used herein, a "synergistic combination" or a "synergistic amount" of a compound of the invention and a therapeutic agent is a combination or amount that is more effective in the therapeutic or prophylactic treatment of a disease than the incremental improvement in treatment outcome that could be predicted or expected from a merely additive combination of (i) the therapeutic or prophylactic benefit of the compound of the invention when administered at that same dosage as a monotherapy and (ii) the therapeutic or prophylactic benefit of the therapeutic agent when administered at the same dosage as a monotherapy.

Pharmaceutical Compositions and Therapies

Compositions of the invention may be administered to a subject in a pharmaceutical composition. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Although the description of pharmaceutical compositions provided herein are principally directed to pharmaceutical compositions which are suitable for ethical administration to humans, it will be understood by the skilled artisan that such compositions are generally suitable for administration to subjects of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats and dogs.

Pharmaceutical compositions that are useful in the methods of the invention may be prepared, packaged or sold in formulations suitable for ophthalmic, oral, parenteral, intranasal, buccal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier and any additional ingredients in a pharmaceutical composition of the invention will vary, depending upon the identity, size and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound and the like. In particular, parenteral administration is contemplated to include, but is not limited to, intraocular, intravitreal, subcutaneous, intraperitoneal, intramuscular, intrasternal injection, intratumoral and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes and implantable sustained-release or biodegradable formulations. Such formulations may further comprise one or more additional ingredients including, but not limited to, suspending, stabilizing or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution and fixed oils such as synthetic mono- or di-glycerides. Other parentally-administrable formulations which are useful include those which comprise the active ingredient in microcrystalline form, in a liposomal preparation or as a component of a biodegradable polymer system. Compositions for sustained release or implantation may comprise pharmaceutically acceptable polymeric or hydrophobic materials such as an emulsion, an ion exchange resin, a sparingly soluble polymer or a sparingly soluble salt.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

The therapeutic and prophylactic methods of the invention thus encompass the use of pharmaceutical compositions comprising a splice altering oligonucleotide of the invention to practice the methods of the invention. The precise dosage administered will vary depending upon any number of factors, including but not limited to, the type of animal and type of disease state being treated, the age of the animal and the route of administration.

The compound may be administered to a subject as frequently as several times daily, or it may be administered less frequently, such as once a day, once a week, once every two weeks, once a month or even less frequently, such as once every several months or even once a year or less. The frequency of the dose will be readily apparent to the skilled artisan and will depend upon any number of factors, such as, but not limited to, the type and severity of the disease being treated, the type and age of the subject, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples. The following working examples therefore, specifically point out the preferred embodiments of the present invention, and are not to be construed as limiting in any way the remainder of the disclosure.

Example 1

U1 snRNP Determines mRNA Length and Regulates Isoform Expression

U1 snRNP (U1), in addition to its splicing role, protects pre-mRNAs from drastic premature termination by cleavage and polyadenylation (PCPA) at cryptic polyadenylation signals (PASs) in introns. Here, to define the parameters involved in PCPA and its suppression, a strategy (HIDE-seq) was devised to select and sequence only differentially expressed transcripts, identifying changes that occur upon U1 decrease to various levels and in different organisms. The sequence information obtained from HIDE-seq provided genome-wide PCPA maps and these, together with direct experiments, revealed that U1's PCPA suppression is not only essential for protecting nascent transcripts, but is also a global gene expression regulation mechanism. Unexpectedly, PCPA position varied widely with the degree of U1 decrease, trending to usage of more proximal PASs with greater reduction. This yielded mRNAs with shorter 3' untranslated regions (3' UTRs) and alternatively spliced isoforms resulting from usage of more proximal alternative polyadenylation (APA) sites, characteristic of activated immune, neuronal, and cancer cells (Flavell et al., 2008, Neuron 60:1022-1038; Mayr and Bartel, 2009, Cell 138: 673-684; Niibori et al., 2007, Neurosci Res 57:399-410; Sandberg et al., 2008, Science 320:1643-1647). It is demonstrated that a U1 decrease can recapitulate such specific mRNA changes that occur during neuronal activation. Indeed, it is shown that the rapid transcriptional up-regulation during neuronal activation is a physiological condition that creates U1 shortage relative to nascent transcripts. Furthermore, U1 over-expression inhibits activated neurons' mRNA signature shortenings. It is suggested that by determining the degree of PCPA suppression, U1 levels play a key role in PAS usage and hence mRNA length. A model is proposed whereby U1 binds to nascent pre-mRNAs co-transcriptionally to explain how U1 shortage results in a corresponding loss of distal PASs suppression from the cleavage and polyadenylation machinery that is associated with the RNA polymerase II (polII) transcription elongation complex (TEC) (Das et al., 2007, Mol Cell 26:867-881; Hirose and Manley, 1998, Nature 395:93-96; McCracken et al., 1997, Nature 385:357-361). Additional experiments are consistent with the explanation that co-transcriptional PCPA counteracted by U1 association with nascent-transcripts, a process termed herein as telescripting, ensuring transcriptome integrity and regulating mRNA length.

The materials and methods employed in these experiments are now described.

Antisense Morpholino Oligonucleotides

U1 AMOs are the same in mouse and human. This sequence and that of *Drosophila* U1 AMO (dU1) are listed elsewhere herein.

Cell Treatments

HeLa, NIH/3T3, and S2 cells were transfected by electroporation using a Genepulser (Bio-Rad) or Nucleofector (Amaxa) with control or antisense morpholino (AMO) to U1 at 0.25, 1.0 and 15 nmole for 8 hrs as described (Kaida et al., 2010, Nature 468:664-668). HeLa transfection with gene-specific AMOs (15 nmole/7.5 µM) to PASs, 5' and 3' splice site was performed in the same manner. All AMO sequences synthesized by Gene Tools are listed elsewhere herein. SSA treatment was 100 ng/ml for 8 hrs. PC12 and MN-1 cells were stimulated with 20 µM forskolin and/or 50 mM KCl for 3 hrs (Impey et al., 1998, Neuron 21:869-883) or transfected with U1 AMO for 8 hrs by Amaxa Nucleofector.

HIDE-Seq Library Preparation

Subtracted cDNA libraries were prepared using Clontech's PCR-Select cDNA Subtraction kit (Diatchenko et al., 1996, Proc Natl Acad Sci USA 93:6025-6030; Gurskaya et al., 1996, Anal Biochem 240:90-97; Lukyanov et al., 1995, Anal Biochem 229:198-202) with several modifications listed below. Poly(A) RNA was reverse transcribed with random hexamers and custom oligo(dT) primers containing blunt end restriction sites to prepare individual cDNA pools. Following second strand synthesis, ds cDNAs were each digested separately with RsaI, HaeIII, or AluI, to produce independent libraries of the same samples. Each sample (control AMO or U1 AMO) served as the tester or the reference (i.e. forward and reverse subtractions). Ligation of adaptors, hybridization, and primary PCR (FIG. 1A, left gel) steps were done as described elsewhere herein. Nested PCR (FIG. 1A, right gel) was performed on each library with primers containing 454 adaptors, barcodes, and linker molecules. Forward and reverse libraries were multiplexed, subjected to emulsion PCR, and bi-directionally sequenced using Titanium 454 chemistry.

Genomic Tiling Arrays, RT-PCR, Real Time and 3' RACE

Arrays were performed in triplicate for human chromosomes 5, 7 and 16 (Kaida et al., 2010, Nature 468:664-668). All primers, RNA preparation methods, conditions, and cell types are listed elsewhere herein. mRNA isoform and U1 snRNA levels determined by qPCR were normalized to G6PDH and 5s rRNA, respectively.

Mini-Gene, Mutant U1 Transfections and U1 Over-Expression

The NR3C1 mini-gene and the 5' splice site and PAS mutations contained therein have been described (Kaida et al., 2010, Nature 468:664-668). To duplicate the PAS, the NR3C1 plasmid EcoRV-StuI fragment was reinserted into the original mini-gene at the EcoRV site. Modification of U1's 5' splice site binding domain and plasmid concentrations are described elsewhere herein. 3'RACE products were digested with HindIII to distinguish PCPA and mRNA bands. PC12 were transfected with U1 snRNA in a pSiren-RetroQ expression vector (Clontech) driven by the native U1 promoter. RT-qPCR using probes specific for a 1 bp difference in transfected U1 was used to determine the extent of over-expression.

Tritiated Uridine Labeling of mRNA

PC12 cells were pulsed with 50 µCi of 5'6'-$^3$H uridine in 500 µl media with 0.04 µg/ml actinomycin D for 30 min before collecting. Total RNA was isolated by Trizol and poly(A) RNA was selected on Oligotex beads (Qiagen). Radioactivity in each fraction was determined by scintillation counts and ratios of mRNA to total RNA were normalized to the concentration of total RNA determined on a Nanodrop spectrophotometer.

High Throughput Sequencing

Titanium 454 sequencing was performed at the University of Pennsylvania DNA Sequencing Facility or at Macrogen (Seoul, Korea) according to manufacturer recommendations.

Data Analysis and Bioinformatic Pipeline Construction

Sequence reads were filtered for correct primers, binned by barcodes and aligned to the human genome (hg18) using GMAP (Wu and Watanabe, 2005 Bioinformatics 21: 1859-75) with default parameters. The best alignment for a read was based on coverage (i.e., the percentage of the read aligned to the genome), and in the event of a tie in coverage score, the alignment with greatest sequence identity was chosen. Reads with multiple alignments to the genome, having the same coverage and identity were discarded, as were reads with less than 90% coverage/90% identity. Comparable alignment results were obtained with BLAT [www.genome.org/cgi/content/abstract/12/4/656]. Alignments were then agglomerated and affected regions of the genome were identified for each subtraction, i.e. either Control-U1 or U1-Control. Regions in both subtraction directions aligning to the same genomic location were considered background and disregarded. The remaining regions uniquely affected in each subtraction were then annotated using the canonical transcript annotations of Refseq hg18. In the rare event of multiple canonical transcript isoforms for a single gene, the longest transcript was chosen as the representative transcript for a gene. Bedfiles are generated for visualization of data on the UCSC genome browser. Use of the data analysis pipeline is available at (www.upenn.edu/dreyfusslab).

Poly(A) Read Identification, Density Plots and Calculations

HIDE-seq reads in the U1-Control subtractions with poly (A) tails not found in the genome sequence were selected as follows: For all reads, barcode (#2) and primers were removed, data was trimmed for quality (score <20) and sequences were aligned to the respective reference genomes. Sequences ending in stretches of 6 or more A's that did not align to the genome, or for which the upstream aligning sequence was not in an annotated 3'UTR, were binned and confirmed by visual inspection. Genomic coordinates and sequences of definitive PCPA found in human (n=71), mouse (n=70) and *Drosophila* (n=60) are in FIG. 9, FIG. 10, and FIG. 11. PAS scores were generated using the polya_svm prediction tool at: polya.umdnj.edu/polyadb/. Gene lengths and distances relative to the TSS, the 5' splice site and 3' splice site were plotted in R. These and the amounts of intronic sequence were calculated using the canonical transcript database (Rhead et al., 2010 Nucleic Acids Res. 38: D613-D619).

Classification of Transcriptome Changes

To assess the relative prevalence of patterns observed (FIG. 2B), an unbiased bioinformatic approach was applied to classify transcriptome changes. Each pre-mRNA transcript is treated as a sequence of alternating exon and intron blocks and the alignment of one or more reads in either subtraction indicates the presence of a unique change. Transcripts were initially placed into four classes using a heuristic approach, based on the pattern of consecutive exon and intron blocks being "up" or "down." Class 1 represents transcripts showing at least one exon or intron being up while none are down. Class 2 has the opposite criteria. Class 3 transcripts show a Z pattern, which consists of a series of one or more exons or introns being "up," followed by one or more exons being down. Class 4 contains all "other" patterns that do not fall under a defined category.

A further sub-classification of these was accomplished with the following optimization strategy, comparing the observed transcript with ideal patterns for each. Class 1 was subdivided into: all exons only "up," all exons "up" with intron retention, 5' exons and/or introns "up" with no change in 3' end, which is referred to as a 7 pattern, single or multiple intron retention with no 5' bias, or "Other." Conceptually, the case of all exons "up" may be viewed as a straight line with normalized amplitude 1. A 7 may be viewed as a step function having amplitude of 1 in exon numbers 1 to k, where k ideally is equal to half the number of exons, and amplitude 0 in exon numbers k+1 to n, where n is the number of exons in the transcript. Therefore, classification was reduced to fitting a sigmoid or step function to the data and estimating k via least squares regression. If k was less than 0.75 n, then the transcript is classified as a 7, otherwise the transcript was classified as all exons "up" with intron retention. If there were too few exon changes to make a decision, then the transcript was classified as "Other." Subdivision of class 2 into "All Exons Down," "L" or "Other" was performed in a similar fashion. Classifications were verified by visual inspection of bedfiles in the USCS genome browser.

RNA Preparation, RT-PCR and 3' RACE

Total RNA was prepared with the RNeasy kit (Qiagen) and poly(A) RNA was isolated from total RNA with Oligotex mRNA kit (Qiagen). Standard RT-PCR was performed with cDNA prepared by Advantage RT-for-PCR (Clontech) from total RNA of transfected cells. Real time, quantitative RT-PCR was performed on an Applied Biosystems Fast 7500 using SYBR green dye chemistry. Fold changes were normalized to levels of actin mRNA. For snRNA quantitation, total RNA was isolated from human (HeLa, 293T, U205, and primary fibroblasts) mouse (primary fibroblasts, muscle and astrocytes; MN1 and C2C12) and *Drosophila* (S2 and Kc167) cell lines using mirVana miRNA isolation kit (Ambion) as recommended by the manufacturer. 10 ng (or 2 ng for U1) of total RNA was used for linear RT amplification reactions using the Advantage RT-for-PCR kit (Clontech), with reverse primers specific to each snRNA. 4% of cDNA product was used as input in real-time qPCR measurements using a 7900HT Fast Realtime PCR system (ABI). Standard curves were generated with serial dilutions of known amounts of purified snRNA PCR product and produced for each experiment to ensure accuracy. For 3' RACE, RNA was reverse transcribed using an [oligo(dT)-XbaIKpnIHindIII] primer, followed by nested PCR using distinct gene-specific or plasmid-specific forward primers and a common reverse primer, XbaIKpnIHindIII, for 20 cycles each.

Mutation of U1 snRNA Genes.

The wild-type 5' splice site recognition sequence of U1 (5'-ACTTACCTG-3'; SEQ ID NO: 1) was mutated to the following sequences for FIG. 5C: U1-A (5'-CTGCTGTTG-3'; SEQ ID NO: 2), U1-B (5'-TGAATGGAC-3'; SEQ ID NO: 3), U1-C (5'-CTACAGATG-3'; SEQ ID NO: 4), and U1-D (5'-CACCCCTAC-3'; SEQ ID NO: 5).

Sequences of Antisense Oligonucleotide Morpholinos and PCR Primers

| Antisense Morpholinos: | Sequence (SEQ ID NO) |
|---|---|
| Control AMO | CCTCTTACCTCAGTTACAATTTATA (SEQ ID NO: 6) |
| U1 AMO | GGTATCTCCCCTGCCAGGTAAGTAT (SEQ ID NO: 7) |
| U2 AMO | TGATAAGAACAGATACTACACTTGA (SEQ ID NO: 8) |
| U6atac AMO | AACCTTCTCTCCTTTCATACAACAC (SEQ ID NO: 9) |
| U12 AMO | TCGTTATTTTCCTTACTCATAAGT (SEQ ID NO: 10) |
| dU1 AMO | GTTAACCTCTACGCCAGGTAAGTAT (SEQ ID NO: 11) |
| dU2 AMO | GATAAGAACAGATACTACACTTTGA (SEQ ID NO: 12) |
| dU6atac AMO | AACTTGCTCTCCTTCCAAACAACAC (SEQ ID NO: 13) |
| dU12 AMO | GATTGGTTTTCCTTACTCATTAGTT (SEQ ID NO: 14) |
| UBAP2L 3'ss AMO | GGATATTTTCTTCCTAAAAGGAATC (SEQ ID NO: 15) |
| UBAP2L PAS AMO | AATACCACAGTTTATTGAAGACTAC (SEQ ID NO: 16) |

HIDE-Seq Primers:

Hybrid primers consist of 454 A or B sequences (italics), barcodes (underlined) and suppression PCR adaptors sequences (bold).

Control-U1 Library:

FWD 5'-
(SEQ ID NO: 17)
*CGTATCGCCTCCCTCGCGCCATCAG*<u>ACGAGTGCGT</u>GCTCGAGCGGCCGCC

CGGGCAGGT-3'

REV 5'-
(SEQ ID NO: 18)
*CTATGCGCCTTGCCAGCCCGCTCAG*<u>ACGAGTGCGT</u>GGCAGCGTGGTCGCG

GCCGAGGT-3'

U1-Control Library:

FWD 5'-
(SEQ ID NO: 19)
*CGTATCGCCTCCCTCGCGCCATCAG*<u>ACGCTCGACA</u>GCTCGAGCGGCCGCC

CGGGCAGGT-3'

REV 5'-
(SEQ ID NO: 20)
*CTATGCGCCTTGCCAGCCCGCTCAG*<u>ACGCTCGACA</u>GGCAGCGTGGTCGCG

GCCGAGGT-3'.

3' RACE Primers:
NR3C1 primers are listed in Kaida et al., 2010.
To detect PCPA in BASP1:

```
BASP1 int1-1:
                             (SEQ ID NO: 21)
CAGTCTGCCATTGTGACGTG BASP1 int1-2:
                             (SEQ ID NO: 22)
CCAATGGGAGAGCCCTAAAC
```

To detect polyadenylation at the 3' UTR:
```
BASP1 3UTR-1:
                             (SEQ ID NO: 23)
CTGCAATGGGAGTTGGGAG

BASP1 3UTR-2:
                             (SEQ ID NO: 24)
GATGCGTTTGATTCTGCCCAC

ChicEx3 FW1:
                             (SEQ ID NO: 25)
GAGGAGCTCTCCAAACTGATCAGCG ChicEx3 FW2:
                             (SEQ ID NO: 26)
CTGATCAGCGGCTTTGACCA Ten-mEx1 FW1:
                             (SEQ ID NO: 27)
CGAGTATGAGTCGACTCTAGACTGCCG Ten-mEx1 FW2:
                             (SEQ ID NO: 28)
CTCTAGACTGCCGCGACGTGG
```

Universal Reverse Primers:
Oligo dT18-XbaKpnBam:

```
                             (SEQ ID NO: 29)
CTGATCTAGAGGTACCGGATCCTTTTTTTTTTTTTTTTTT

XbaKpnBam:
                             (SEQ ID NO: 30)
CTGATCTAGAGGTACCGGATCC
```

RT-PCR Primers:
To detect spliced mRNA:

```
BASP1Ex1F:
                             (SEQ ID NO: 31)
GCTAACTCAGGGGCTGCATAGGCAC

BASP1EX2R:
                             (SEQ ID NO: 32)
CGTCCTTCTCGCCCTCCTTCTCCTC
```

To detect upstream region of PAS in intron (IR1):
```
BASP1USIF:
                             (SEQ ID NO: 33)
GGGTGGCTTTCTTAATTTGCATC BASP1USIR:
                             (SEQ ID NO: 34)
GATGATTTCCATTGCTGCCACG
```

To detect downstream region of PAS in intron (IR2):
```
BASP1DSIF:
                             (SEQ ID NO: 35)
GTCTTGAAACCACAGCAGTGCCCAG BASP1DSIR:
                             (SEQ ID NO: 36)
CTCAGCACTGACGGCCTTGTTGAGT
```

```
Homer1 short/longFW:
                             (SEQ ID NO: 37)
CAGACGATGAGAGAACACCCGATG Homer1 shortRV:
                             (SEQ ID NO: 38)
TGGCACCTCTGTGGGCCTGTGGC Homer1 longRV:
                             (SEQ ID NO: 39)
CTGTTGCTTCCACTGCTTCACATTGGC Dab1 short/longFW:
                             (SEQ ID NO: 40)
AAGGATAAGCAGTGTGAACAAG Dab1 shortRV:
                             (SEQ ID NO: 41)
TCTAGATCTCCCATCACGGC Dab1 longRV:
                             (SEQ ID NO: 42)
CAGCAGTGCCGAAAGACATA G6DPH FW:
                             (SEQ ID NO: 43)
CGCCTATCAGTCTGTCCCTGGACTCC

G6DPH RV:
                             (SEQ ID NO: 44)
CCTTCCTTTGGTAAGGAGGCTGCCC

CG5168 Ex1 FW:
                             (SEQ ID NO: 45)
CCGGAATTGCTGAGTAAGCTGG

CG5168 Ex2 RV:
                             (SEQ ID NO: 46)
GGAAGGCATATACTGGCAAATGC

Gint3 Ex3 FW:
                             (SEQ ID NO: 47)
CCTTTAGCTCCTCGAATTTAACAG Gint3 Ex4 RV:
                             (SEQ ID NO: 48)
CCTTGATGAACTTCCTCAGAGGAC RAN Ex 3 FW:
                             (SEQ ID NO: 49)
GGTTGGTGATGGTGGTACTGG RAN Ex 5 RV:
                             (SEQ ID NO: 50)
GATTTCGCCTTCACTTTCCTGTC POLR1C Ex3 FW:
                             (SEQ ID NO: 51)
GTGTGGATGTAGTACACATGGATGAAAAC POLR1C Ex4 RV:
                             (SEQ ID NO: 52)
TTATTGTACACCAGGACCTTCTCCACAG POLR1C Ex4 FW:
                             (SEQ ID NO: 53)
CAACTATGGCTGTGGAGAAGGTCCTGGT POLR1C Ex5 RV:
                             (SEQ ID NO: 54)
TCTGACCTGGAGACGAAACTGTAGAGTATCT
```

Real Time RT-qPCR Primers:

```
GABPB1 8FW:
                             (SEQ ID NO: 55)
CAACAGACATTGCTGAAGAAAC
```

-continued

GABPB1 8bleedRV:
ATTTTGGATGACTGCGGC
(SEQ ID NO: 56)

GABPB1 9RV:
CTTTAGGAGCTGCTGTCGATA
(SEQ ID NO: 57)

UBAP2L 24FW1:
GCTCCTACCTCTTCCAAGCAG
(SEQ ID NO: 58)

UBAP2L apa25RV:
ACAAAACACAGCCCCCAGC
(SEQ ID NO: 59)

UBAP2L 24FW2:
TGGTGTGAATGTCAGTGTGAATGC
(SEQ ID NO: 60)

UBAP2L 2526RV:
GCAAGTTGAAGGAAGCAGCAGG
(SEQ ID NO: 61)

Human U1 snRNA FW:
TGATCACGAAGGTGGTTTTCC
(SEQ ID NO: 62)

Human U1 snRNA RV:
GCACATCCGGAGTGCAATG
(SEQ ID NO: 63)

The results of the experiments are now described.

HIDE-Seq: A Strategy for High Throughput Sequencing of Only Transcriptome Differences To identify transcriptome changes after U1 snRNP functional depletion, cDNA libraries were prepared from poly (A) RNA of human cells (HeLa) 8 hr after transfection with 15 nmole of U1 AMO (U1 depleted) or control AMO (Kaida et al., 2010, Nature 468:664-668). Each cDNA library was digested separately with three 4 bp restriction endonucleases to produce fragments of uniform length (~250 bp), and different adaptor oligonucleotides were ligated separately to the 5' ends of the experimental cDNA for subsequent amplification. Subtractive hybridization and suppression PCR selectively amplified only the differentially expressed transcripts (Diatchenko et al., 1996, Proc Natl Acad Sci USA 93:6025-6030; Gurskaya et al., 1996, Anal Biochem 240:90-97). Nested primers fused to 454 sequencer linkers and sample-specific barcodes were used to generate amplicons of subtracted libraries prepared in both U1-Control and Control-U1 directions for massive parallel sequencing in the same well, controlling for sample-to-sample variation (FIG. 1A). The reciprocal sequence reads from bidirectional subtraction further enhanced the definition of transcriptome changes.

High throughput amplicon sequencing was performed using only ¼-½ of a 454 sequencing plate (~300,000 reads) for extensive profiling (Table 1). Nearly 70% of HIDE-seq reads, averaging 150-400 nt, were unambiguously mapped (90% identity/90% coverage) to the genome (Table 1). Reads located in intergenic regions and sequences not unique to either of the subtraction directions were excluded from further analysis. Only a minor fraction (0.03%) was from ribosomal RNA as compared to >70% without subtraction, confirming the efficiency of the method and indicating the majority of reads are informative (Table 1). Importantly, as more reads were obtained the number of new affected genes discovered plateaued (FIG. 1B), as did coverage within a gene, suggesting that extensive coverage was achieved and allowing a lack of reads to indicate little or no sequence change at a given location.

Figure 1C:
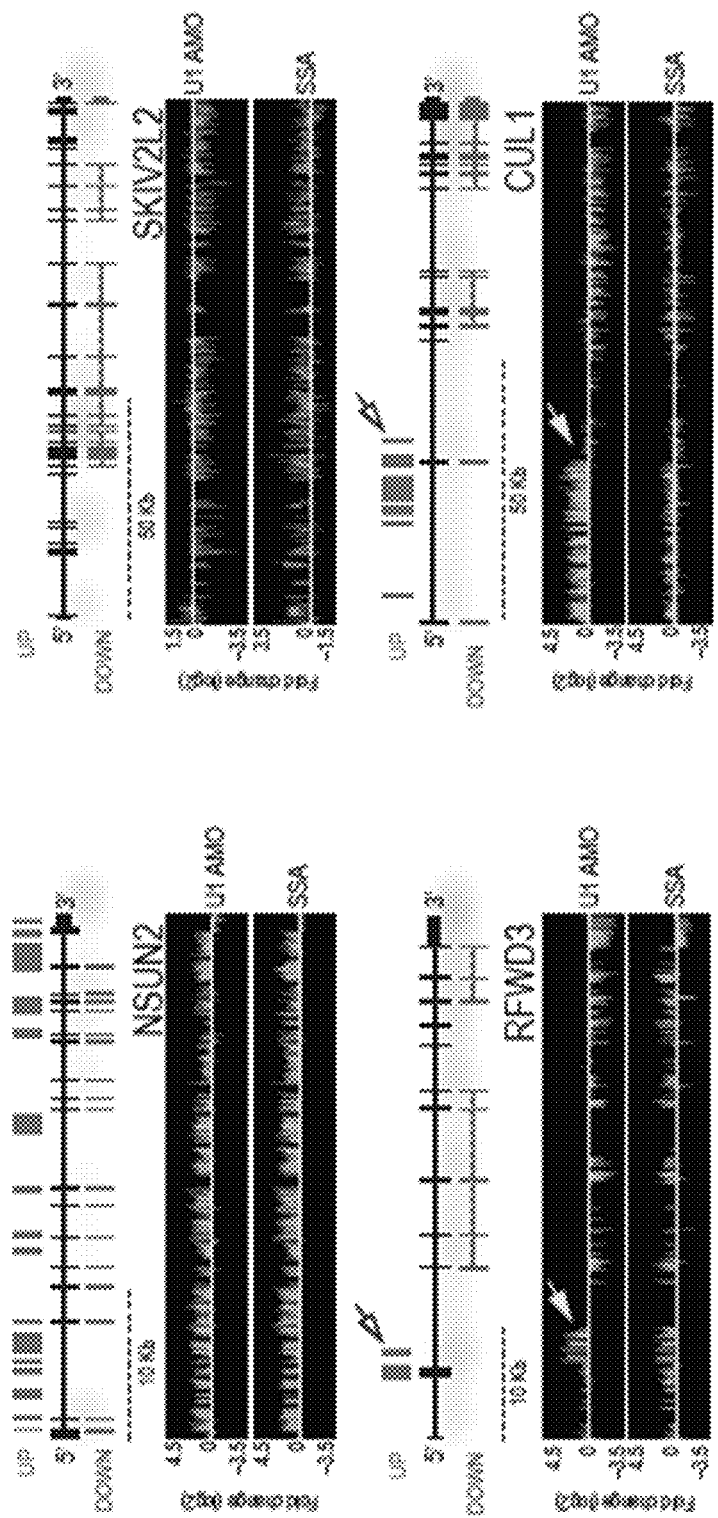
Figures 8A, 8B, 8C, 8D, 8E:
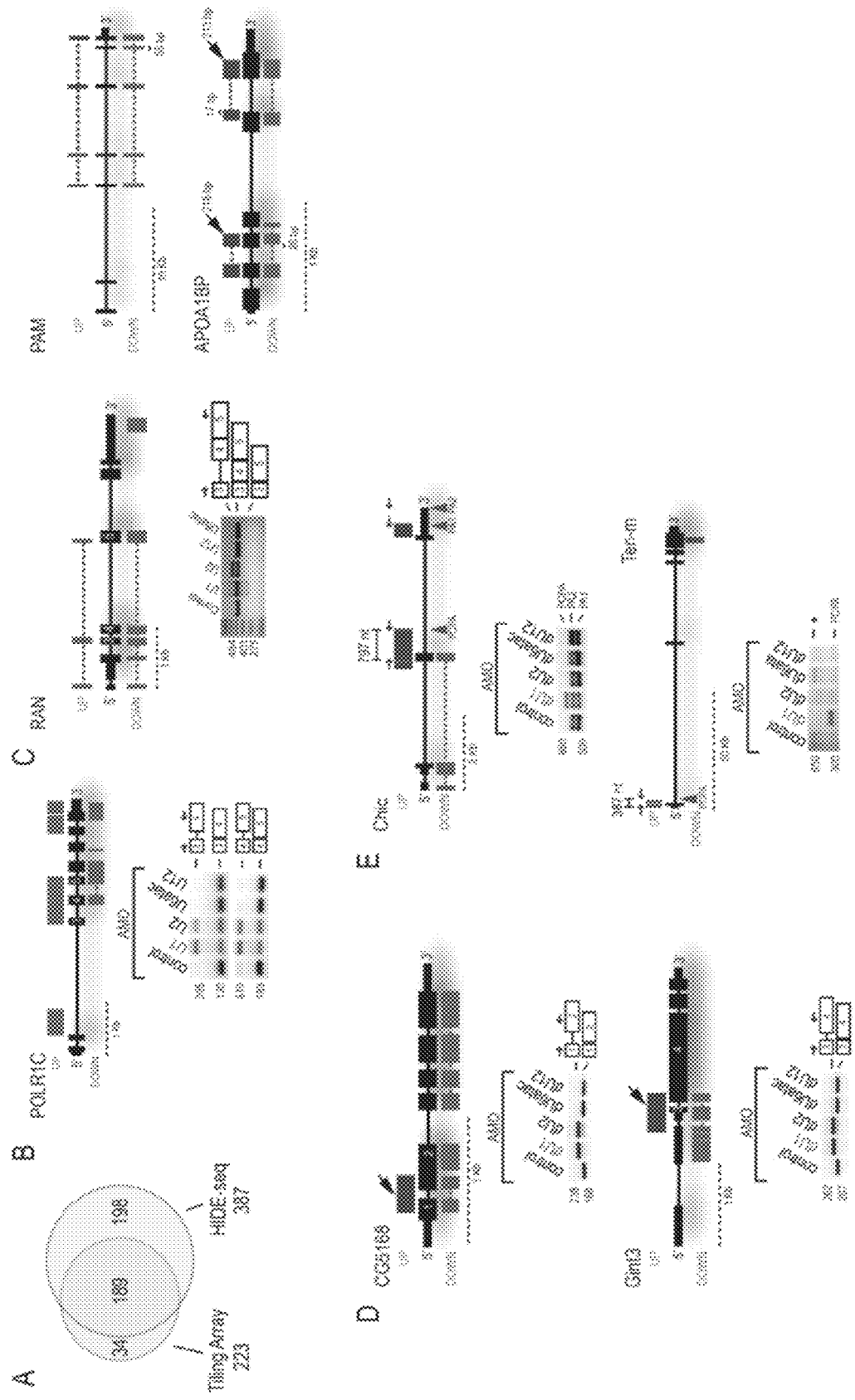
FIG. 8A through FIG. 8E, depicts the results of experiments illustrating HIDE-seq sensitivity and validation of Drosophila U1 AMO.

Data from high density genomic tiling arrays (GTA) of human chromosomes 5, 7, and 16 for HeLa cells treated with U1 AMO under the same conditions used here (15 nmole) provided a comprehensive dataset with which to compare the HIDE-seq methodology (Kaida et al., 2010, Nature 468:664-668). HIDE-seq reads present at a given genomic locus were interpreted as being up or down in U1 AMO-treated cells relative to control, according to whether they came from the U1-Control or the control-U1 subtraction, respectively (FIG. 1C). For GTA SSA was used as a reference for intron accumulation (e.g. NSUN2 and SKIV2L2) and to facilitate discovery of PCPA, represented by 5' intron accumulation that terminates abruptly followed by a decrease in downstream signals (e.g. RFWD3 and CUL1). HIDE-seq readily identified the same transcriptome changes as GTA (FIG. 1C). Sorted for chromosomes 5, 7 and 16, it captured the highly significant (≥2 fold change, ≥100 nt, p-value <0.01) intron accumulations detected by GTA in 85% (189/223) of the genes (FIG. 8A), a very high correspondence considering that RNAs came from separate biological experiments. HIDE-seq discovered 198 additional genes with intron accumulation on these same three chromosomes, 82% of which were confirmed by lower stringency GTA analysis, indicating HIDE-seq is highly reliable and sensitive. Moreover, HIDE-seq identified these and other differences genome wide, capturing subtle sequence changes such as exon skipping (FIG. 8B and FIG. 8C). Although HIDE-seq is not quantitative or necessarily complete, it represents an alternative and complementary approach to full transcriptome sequencing, providing a detailed snapshot of transcriptome differences at a fraction of the cost. Combined with a streamlined informatics pipeline (www.upenn.edu/dreyfusslab), HIDE-seq is a simple and powerful strategy that is widely applicable with different sequencing platforms (e.g., Illumina)

TABLE 1

HIDE-seq produced high quality reads of differentially expressed transcripts

|  | Human (15) | Mouse (15) | Drosophila (15) | Human (1.0) | Human (0.25) |
|---|---|---|---|---|---|
| Total Number of Reads with 454 primers | 394206 | 255808 | 304454 | 97258 | 74889 |
| Total Number of Aligned Reads | 337646 (86%) | 243086 (95%) | 274098 (90%) | 54760 (56%) | 39541 (53%) |
| Uniquely Aligned Reads at 90/90 threshold | 232346 (69%) | 90056 (37%) | 162416 (59%) | 50794 (93%) | 36733 (93%) |
| Number of 90/90 Reads used in Annotation | 150361 (65%) | 68957 (77%) | 113989 (70%) | 38566 (76%) | 27392 (75%) |
| Background, intergenic, short reads | 81985 (35%) | 21099 (23%) | 48427 (30%) | 12228 (24%) | 9341 (25%) |
| Ribosomal RNA reads | 80 (0.03%) | 80 (0.09%) | 39 (0.02%) | nd | nd |

HIDE-seq results following U1 AMO treatment are summarized for human (Hela), mouse (3T3) and *Drosophila* (S2) experiments. Total read numbers and percentages (in parenthesis) are listed. Total reads were those with appropriate 454 primers and barcodes. Aligned reads were those that aligned to the appropriate reference genome assembly [Hs: March 2006 (NCBI36/hg18); Mm: July 2007 (NCBI37/mm9); Dm: April 2006 (BDGP R5/dm3)]. Reads used in the annotation were mapped to one position in the genome with 90% coverage (90% of the read aligned) with 90% identity. Reads not included in the annotation included background (identical) reads present in both subtraction directions, intergenic reads that did not map to known genes, and reads shorter than 50 base pairs. Ribosomal RNA represent the amounts of 16S and 28S rRNA.

PCPA and Its Suppression by U1 are Evolutionarily Conserved

Figures 2A, 2B:
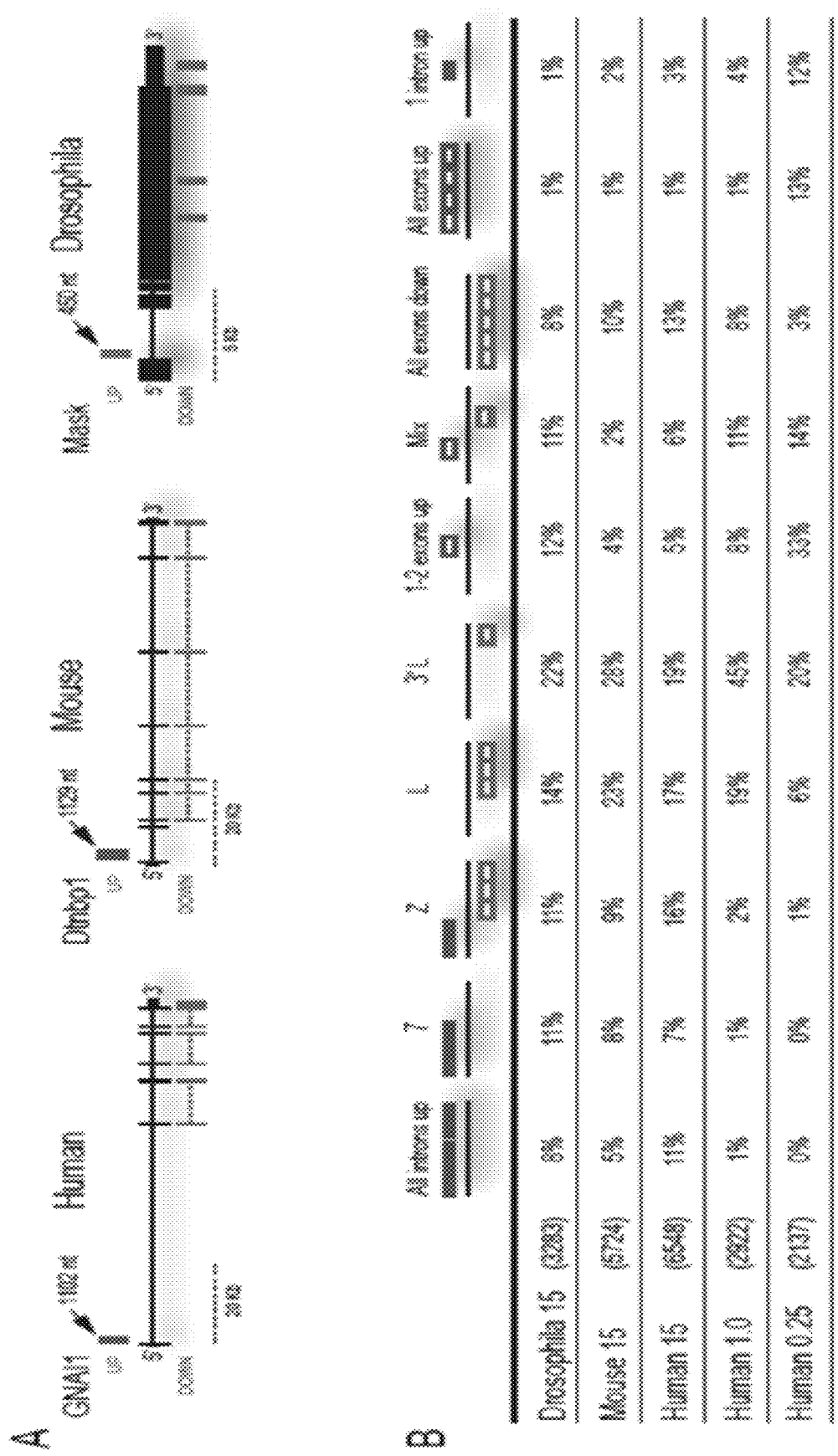
Figure 2:
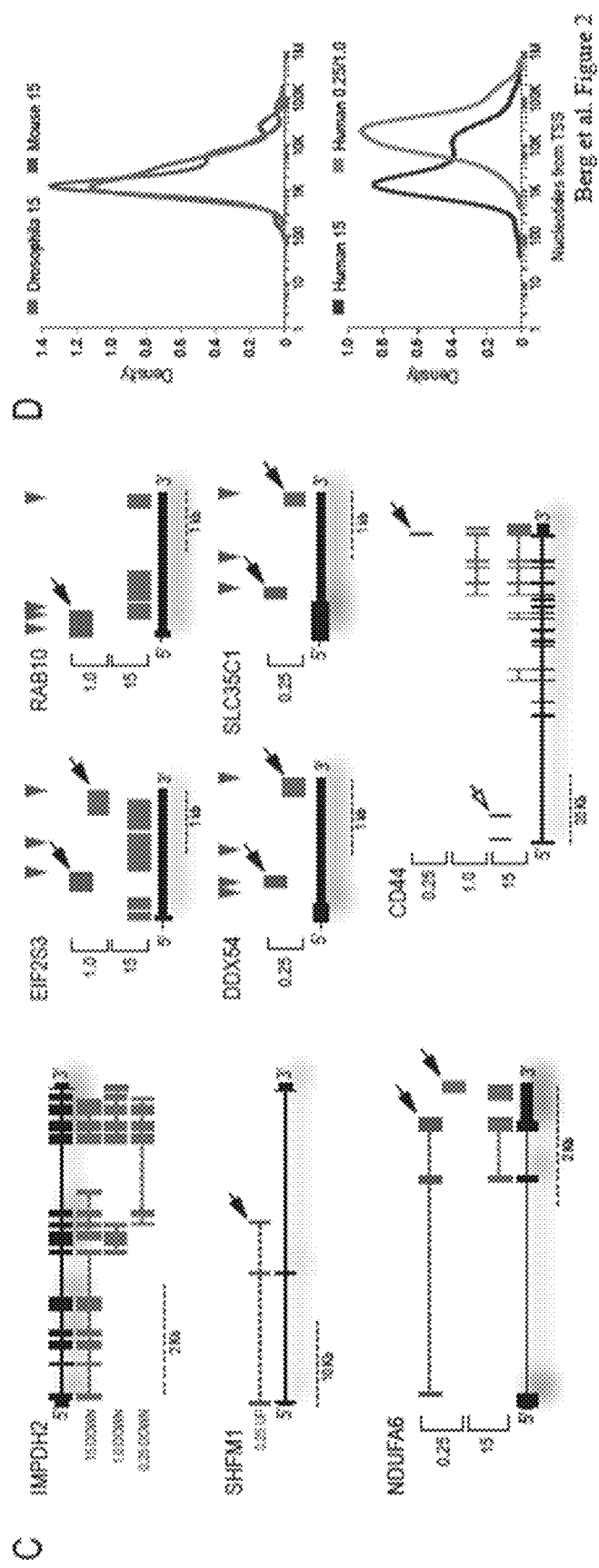
FIG. 2, comprising

HIDE-seq was used to determine if PCPA occurs in divergent organisms following U1 depletion in mouse (3T3) and *Drosophila* (S2) cells (FIG. 1B) with AMOs specific to each organism's U1 5'-end sequence. As in humans, premature termination in introns was U1 snRNP-specific and was not a consequence of splicing inhibition (FIG. 8E). HIDE-seq in HeLa, 3T3, and S2 detected sequence differences in 6548, 5724, and 3283 genes, respectively, which could be classified into several patterns (FIG. 2B). Accumulation of polyadenylated intron reads, followed by a decrease in downstream exon signals, provided the most direct evidence for PCPA (FIG. 2A, FIG. 9, FIG. 10, and FIG. 11). This pattern, designated as Z (FIG. 2B), demonstrated that PCPA typically occurred in intron 1, with little or no transcription beyond that point. An algorithm was developed to detect Z and related patterns, designated as L and 7, which represent PCPA events but either the upstream accumulation or the downstream decrease was not detected, respectively (FIG. 2B). It is likely that differential stability of the various transcripts produced determines whether a Z, 7 or L pattern is observed. Collectively, these accounted for ~40% of the changes. In addition, other patterns consistent with PCPA were detected, such as all exons down (e.g. FIG. 1C; SKIV2L2), likely resulting from very early PCPA, although the possibility of transcriptional down-regulation cannot be excluded. Several genes with all introns up (e.g. FIG. 1C; NSUN2) also had polyadenylated intronic reads, indicating that these, too, do not entirely escape PCPA. Another pattern, 3'L, representing a major class at moderate U1 decrease as discussed later, is similar to L but the down reads (i.e., Ctrl-U1 direction) are near the 3' end of the gene, indicative of transcript shortening. Together, these patterns account for 75-90% of the transcriptome changes in U1 depleted cells, and their remarkable similarity in the three organisms indicates that PCPA and U1's function in its suppression are essential for formation of full-length transcripts for the majority of metazoan genes.

Figure 9:
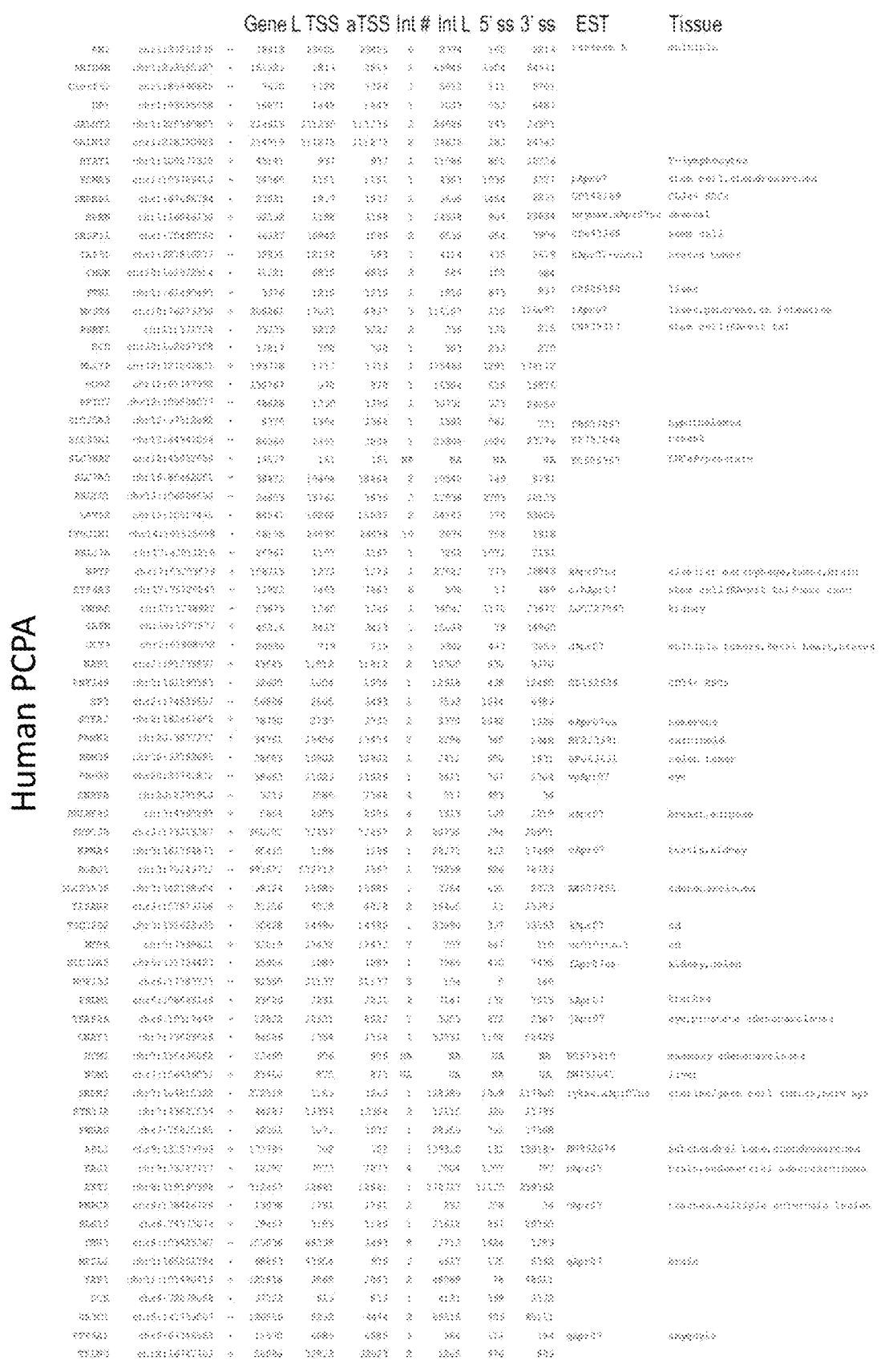
Figure 10:
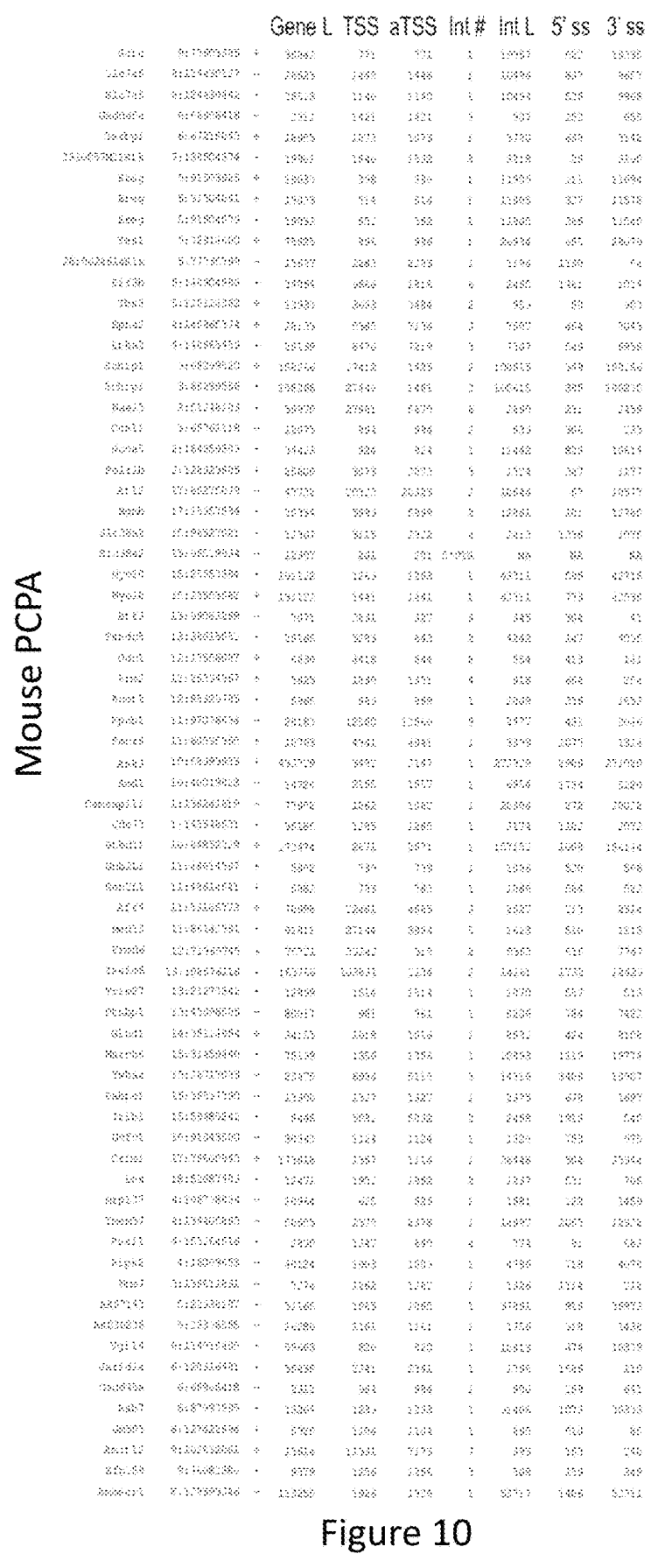
Figure 11:
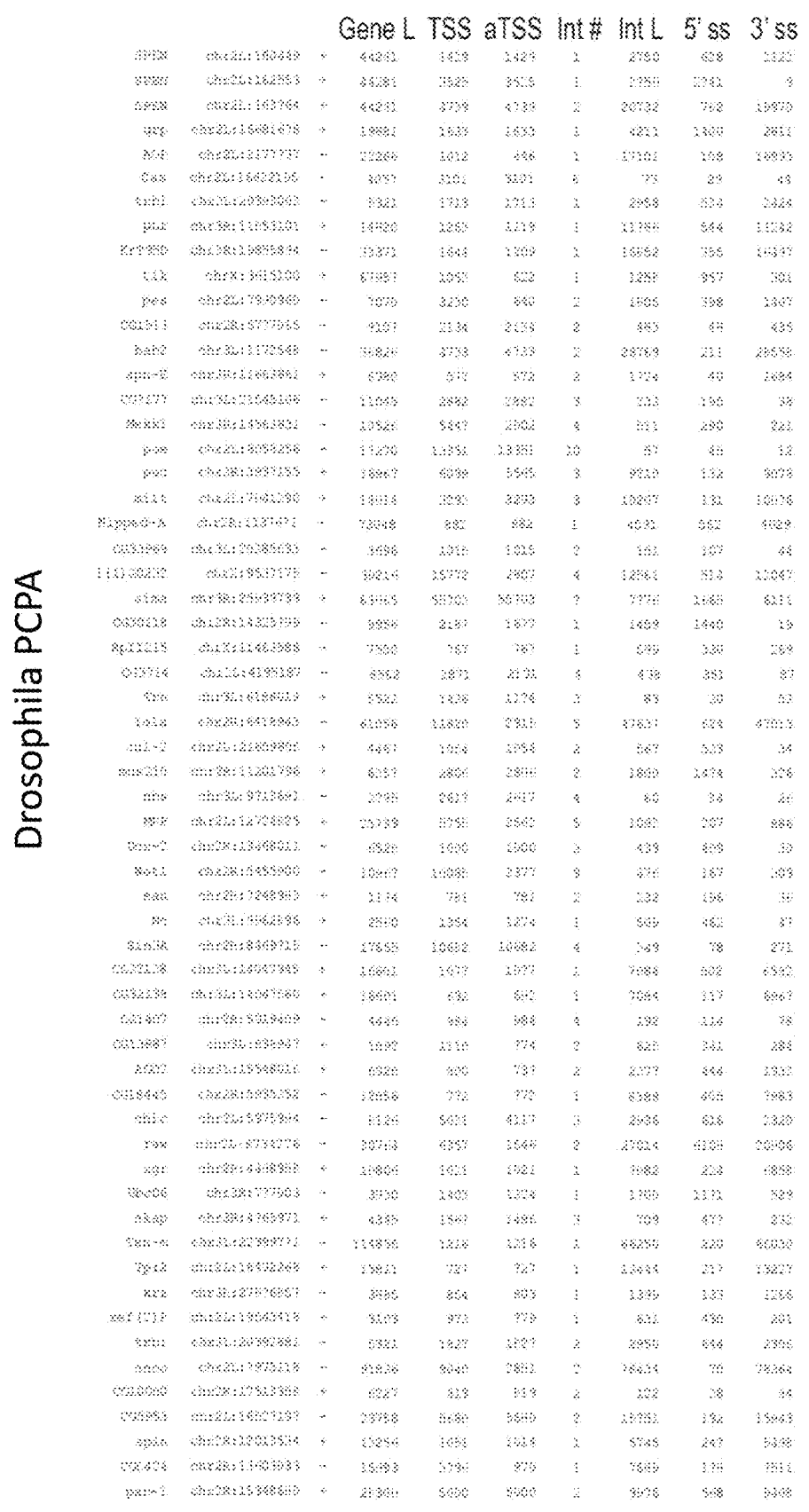

Moderate U1 Decrease Elicits 3'UTR Shortening and a Switch to Shorter mRNA Isoforms The sequencing data from complete U1 depletion indicated that PCPA occurred ~10-30 nt downstream of cryptic PASs that are similar to PASs found at the 3' end of transcripts (Hu et al., 2005, RNA 11:1485-1493) (FIG. 2A; FIG. 9, FIG. 10, and FIG. 11). These included both canonical (AAUAAA or AUUAAA) and rare or not previously described hexamers (Beaudoing et al., 2000, Genome Res 10:1001-1010; Tian et al., 2005, Nucleic Acids Res 33:201-212), as well as U-rich and GU-rich elements that typically surround PASs. To identify PASs that may be particularly vulnerable to PCPA and assess the relevance of U1's suppression under less drastic conditions, U1 levels was decreased by ~25% and 50%, with 0.25 and 1.0 nmole U1 AMO, respectively (Kaida et al., 2010, Nature 468:664-668). Moderate U1 decreases differed from those observed in U1 depletion in three major ways (FIG. 2B). First, significantly fewer genes were affected (~35-50% compared to 15 nmole; FIG. 2B). Second, there was no general intron accumulation, indicating that splicing was not inhibited (FIG. 2B; e.g. All introns up, Z, or 7). Third, and most surprisingly, moderate U1 decrease shifted the PCPA positions towards much greater distances from the TSS. Representative examples of the major patterns from various U1 level decreases are shown in FIG. 2C. The majority of changes at the moderate U1 decrease showed a 3'L pattern, reflecting decreases near the ends of genes (e.g. IMPDH2) and consisted mostly of decreases in distal 3'UTR reads (e.g. EIF2S3, FIG. 12 and FIG. 13), suggesting 3' UTR shortening in genes of a wide range of sizes. A widespread shift to usage of more proximal PASs in introns in the 3' half of genes (e.g. SHFM1) was also observed. Many of the genes at 0.25 nmole U1 AMO that had shorter 3'UTR (e.g. NDUFA6), also had several exon signals up-regulated (FIG. 2B), possibly due to elimination of miRNA targets in the 3' UTR (Bartel, 2009, Cell 136:215-233). The CD44 gene (FIG. 2C) illustrates the PCPA continuum and its U1 dose-dependence, having a shorter 3'UTR at 0.25, an L pattern at 1.0, and a Z pattern from PCPA in the first intron at 15, suggesting usage of more proximal PASs in the same gene with further decrease of U1.

Figure 12:
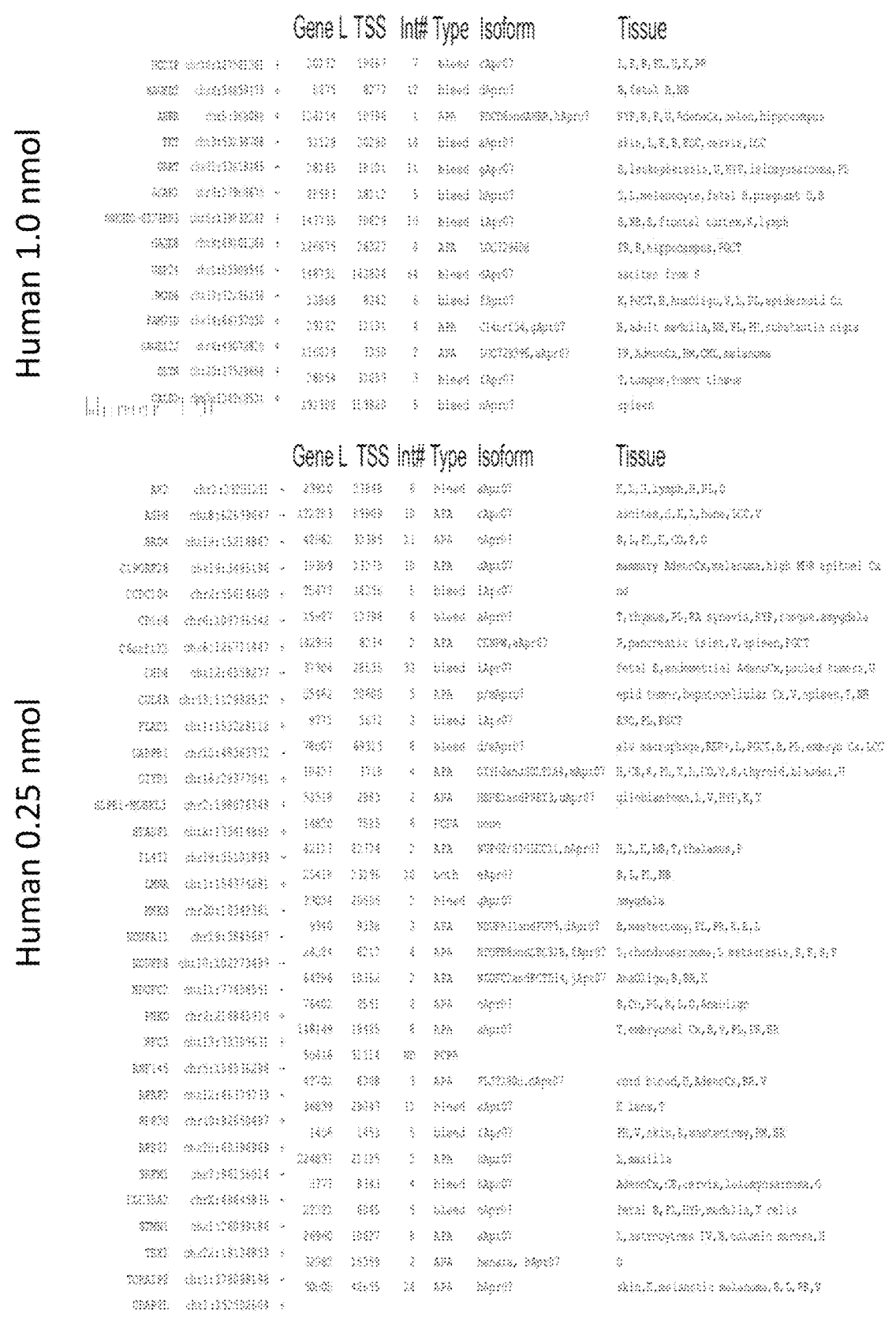

The overall change in PCPA position with the degree of U1 level decrease is illustrated in FIG. 2D. Upon U1 depletion in three organisms, most PCPA occurred ~1 kb from the TSS, typically in the first (48%) or one of the first introns (intron 2: 26%; intron 3: 11%). However, at lower U1 decreases, PCPA occurred at much greater distances from the TSS (~20 kb) (FIG. 2D—lower panel, FIG. 12, Table 2). In most, if not all cases, including transcripts that terminated within ~1 kb from the TSS, several strong predicted PASs, and many more non-canonical PASs were bypassed before the site of PCPA. Importantly, many of the PCPA sites coincided precisely with previously reported polyadenylated ESTs from a wide range of cell types and tissues (FIG. 9 and FIG. 12), suggesting that PCPA is a natural phenomenon that occurs under normal physiological conditions.

Figure 13:
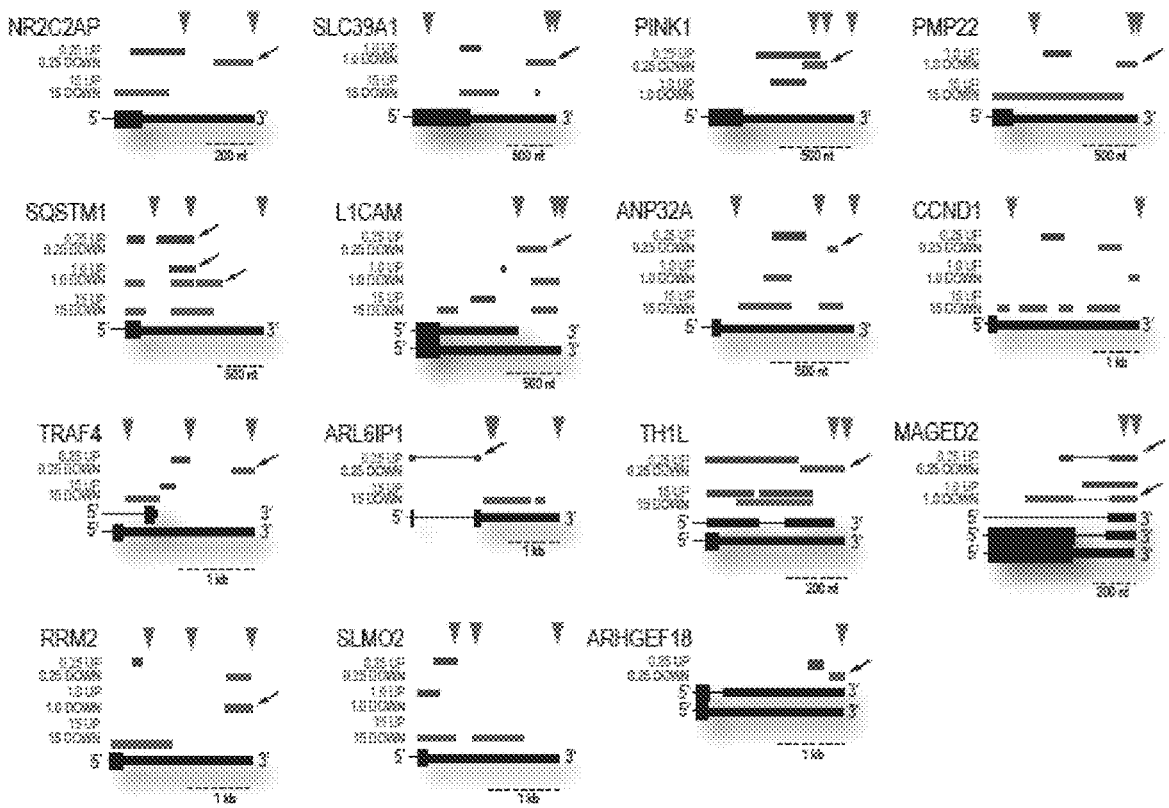
FIG. 13, comprising

Loss of U1 PAS Suppression Promotes Alternative Splicing of Proximal 3' Terminal Exons Two types of mRNA changes resulting from PCPA at low U1 AMO (Human 1.0 and 0.25) were detected, in addition to 3'UTR shortening (FIG. 13). First, PCPA in introns produced shorter mRNAs that lack the downstream exons and 3'UTR of the full-length transcript. In some of these the open reading frame (ORF) of the alternative terminal exon could potentially extend into the intron (FIG. 3A), a scenario referred to as a "composite" or "bleeding" exon (Tian et al., 2007, Genome Res 17:156-165). Quantitative RT-PCR on RNA of cells transfected with a range of U1 AMO doses confirmed the shift to proximal polyadenylation predicted by HIDE-seq (FIG. 3A). As expected, upon U1 depletion both short and long isoforms decreased, due to early PCPA or splicing inhibition, indicated by the Z patterns (e.g. GABPB1 2.5 and 15 nmole). At low U1 AMO, however, rather than an overall transcript level decrease, the amounts of the short forms remained relatively stable while the long forms decreased, causing the ratio of the short to the long isoform to increase (FIG. 3A).

Figure 3:
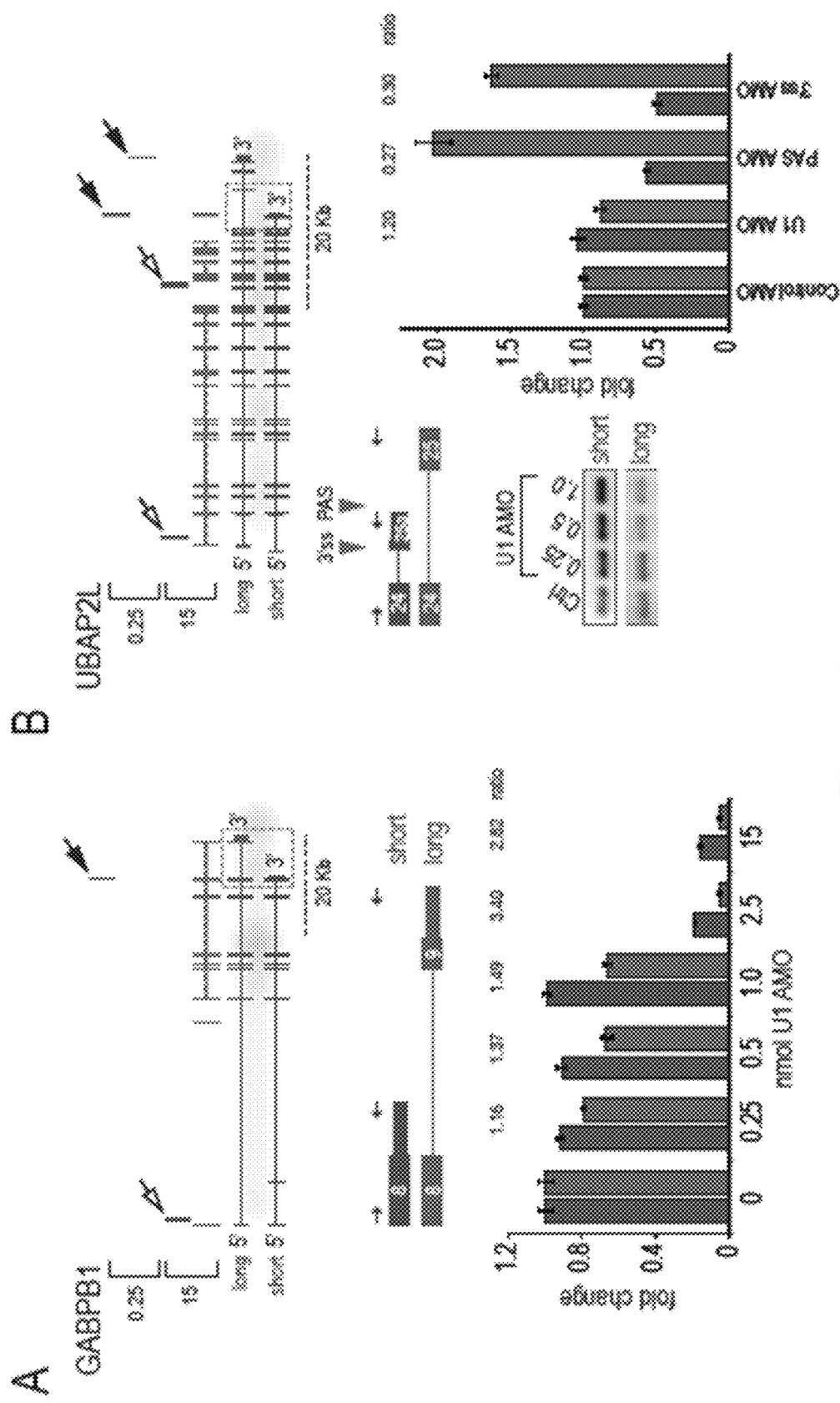
FIG. 3, comprising

A second type of polyadenylated read found in introns of the canonical transcript at low U1 AMO (solid arrows) mapped to the ends of exons that can be alternatively spliced mutually exclusively with the full-length gene's terminal exon ("short" in FIG. 3), an example of splicing-dependent APA (Edwalds-Gilbert et al., 1997, Nucleic Acids Res 25:2547-2561; Zhang et al., 2005, Genome Biol 6(12): R100). The UBAP2L gene (FIG. 3B) displayed a dose-dependent increase in the relative amount of the shorter isoform at low U1 AMO (RT-PCR gel inset). Interestingly, many 3' exon switching cases, including UBAP2L, have been reported following immune cell activation and suggested to result from alternative splicing (Sandberg et al., 2008, Science 320:1643-1647). However, an alternative mechanism was considered, in which PCPA occurs first and that it is this event that causes the upstream 5' splice site to splice to an alternative 3' splice site not utilized in the full-length transcript. To address this, AMOs were used to block either the 3' splice site or the PAS of the short isoform and measured the levels of both isoforms by RT-qPCR (FIG. 3B). As expected, the 3' splice site AMO caused a switch to the long isoform by blocking alternative splicing. Interestingly, the PAS AMO also caused the level of the short isoform to drop drastically, while the long isoform doubled (FIG. 3B; PAS AMO). Taken together, these data suggest that loss of U1 suppression of a PAS determines alternative splicing to a mutually exclusive terminal exon.

PCPA and Its Suppression is a 5'-3' Directional Process

HIDE-seq provided information on PCPA position in introns, revealing that it occurred in all three organisms at a median distance of 500-1000 nt from the nearest 5' splice site (FIG. 4A), but at variable and usually much greater distances from the nearest 3' splice site (FIG. 4A) (FIG. 9, FIG. 10, FIG. 11, and Table 2). In each organism cases of multiple PCPA sites within the same intron (e.g., Spen, RBM39) or same transcript (e.g., Spen, S1c38a2) were found, demonstrating that there are several actionable PASs along a transcript (FIG. 4B) and it is likely that U1 bound at the 5' splice site and elsewhere in introns is required to suppress them.

Figure 4:
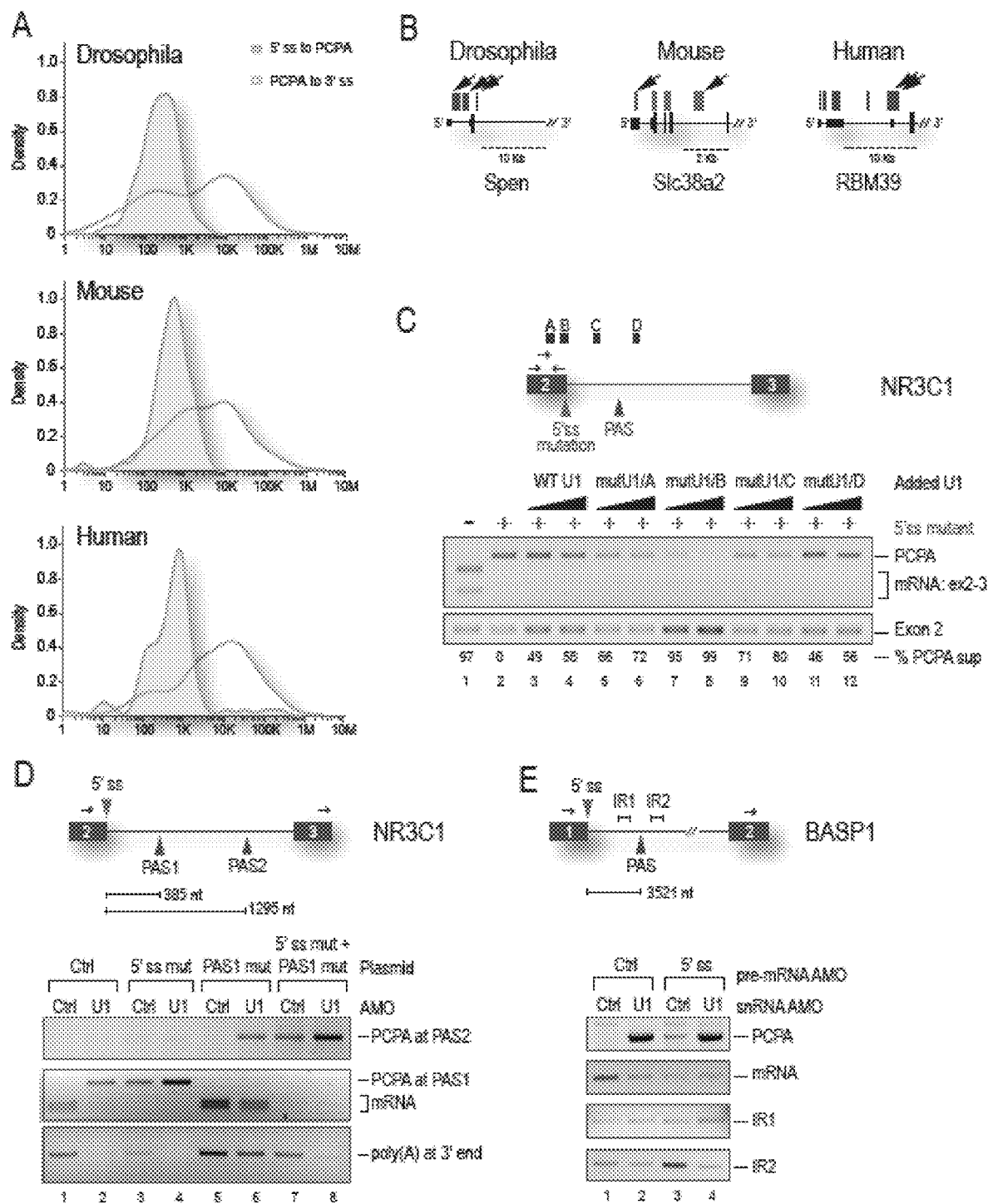
FIG. 4, comprising

B). Varying degrees of suppression were observed also for U1s tethered elsewhere, to the intron and upstream exon both in the vicinity of the cryptic PAS (~45-80%), and by increasing WT U1. This suggests that U1 can suppress PCPA even without being able to function in splicing and that U1 bound upstream does so more efficiently (e.g. mutU1/A and mutU1/C). Next, a NR3C1 mini-gene was constructed in which the actionable PAS in intron 2 was duplicated (FIG. 4D). Transfection of this construct with U1 AMO (lane 2) caused PCPA at the first PAS (PAS1; 385 nt) and as previously reported, a 5' splice site mutation caused PCPA (lane 3), but more occurred from this PAS in the presence of U1 AMO (lane 4) (Kaida et al., 2010, Nature 468:664-668). When PAS1 was mutated, PCPA now occurred from the second PAS (PAS2) located 1295 nt from the 5' splice site, indicating that a downstream PAS(s) is also vulnerable and that PCPA occurs with 5' to 3' directionality. When both the 5' splice site and PAS1 were mutated, some PCPA occurred from PAS2 (lane 7), indicating that protection from the 5' splice site extends out to PAS2, but again U1 AMO elicited more PCPA (lane 8) suggesting that additional PCPA suppression is provided by U1 bound to sequences other than the 5' splice site.

To address how far beyond a 5' splice site U1 snRNP's PCPA suppression extends, the endogenous BASP1 gene was studied, which is PCPAed relatively far from the 5' splice site, ~3.5 kb into the first intron (FIG. 4E). Interestingly, little or no PCPA occurred with a 5' splice site-blocking AMO (lane 3), while co-transfection with the 5' splice site AMO and U1 AMO (lane 4) resulted in a substantial amount, suggesting that suppression by U1 from the 5' splice site alone is insufficient. Additional controls confirmed that the 5' splice site AMO was effective in inhibiting splicing (lanes 2-4: mRNA decreases and IR1 increases) and a cryptic 5' splice site was not activated (FIG. 4E). It is concluded that at a distance of 3.5 kb, a PAS is outside the protective range of 5' splice site-bound U1. Taken together, the HIDE-seq data and direct probing demonstrate the 5' to 3' directionality of the PCPA process and strongly suggest a need for U1 in excess of what is required for splicing.

TABLE 2

Summary of PCPA distances
The median, mean and standard deviation was calculated for the values presented in FIG. 9, FIG. 10, FIG. 11, and FIG. 12.

|  | Human (15) | | | Mouse (15) | | | Drosophila (15) | | | Human (1.0/.25) | | |
| --- | --- | --- | --- | --- | --- | --- | --- | --- | --- | --- | --- | --- |
|  | Median | Mean | sd | Median | Mean | sd | Median | Mean | sd | Median | Mean | sd |
| Gene Length | 38780 | 83009 | 132728 | 24827 | 52568 | 76670 | 11006 | 20305 | 23246 | 37679 | 59771 | 57869 |
| Distance from TSS | 3413 | 20175 | 69988 | 1445 | 6491 | 14333 | 1639 | 4075 | 7570 | 15359 | 25164 | 31914 |
| Distance from nearest TSS | 1965 | 8269 | 16591 | 1306 | 2391 | 3045 | 1377 | 3104 | 7269 | nd | nd | nd |
| Intron Number | 2 | 2.1 | 1.7 | 1 | 2.1 | 1.8 | 2 | 2.4 | 1.9 | 5 | 7.9 | 10.4 |
| Intron Length | 7340 | 25844 | 46182 | 3780 | 17793 | 40755 | 2091 | 8059 | 14830 | NA | NA | NA |
| Distance from 5' splice site | 570 | 800 | 1368 | 549 | 741 | 655 | 346 | 555 | 878 | NA | NA | NA |
| Distance from 3' splice site | 6752 | 25044 | 45340 | 3190 | 17052 | 40531 | 1546 | 7510 | 14785 | NA | NA | NA |

To probe PCPA mechanism, it was investigated if a splicing-defective U1 can suppress PCPA, using NR3C1 mini-gene constructs (FIG. 4C) (Kaida et al., 2010, Nature 468:664-668). The WT mini-gene (lane 1) splices properly whereas a 5' splice site mutation causes PCPA 385 nt into intron 2 (lane 2). PCPA was completely suppressed by a 5' end mutated U1 complementary to the 5' splice site (mutU1/

U1 Decrease Recapitulates Isoform Shortening in Activated Neurons

Figure 5:
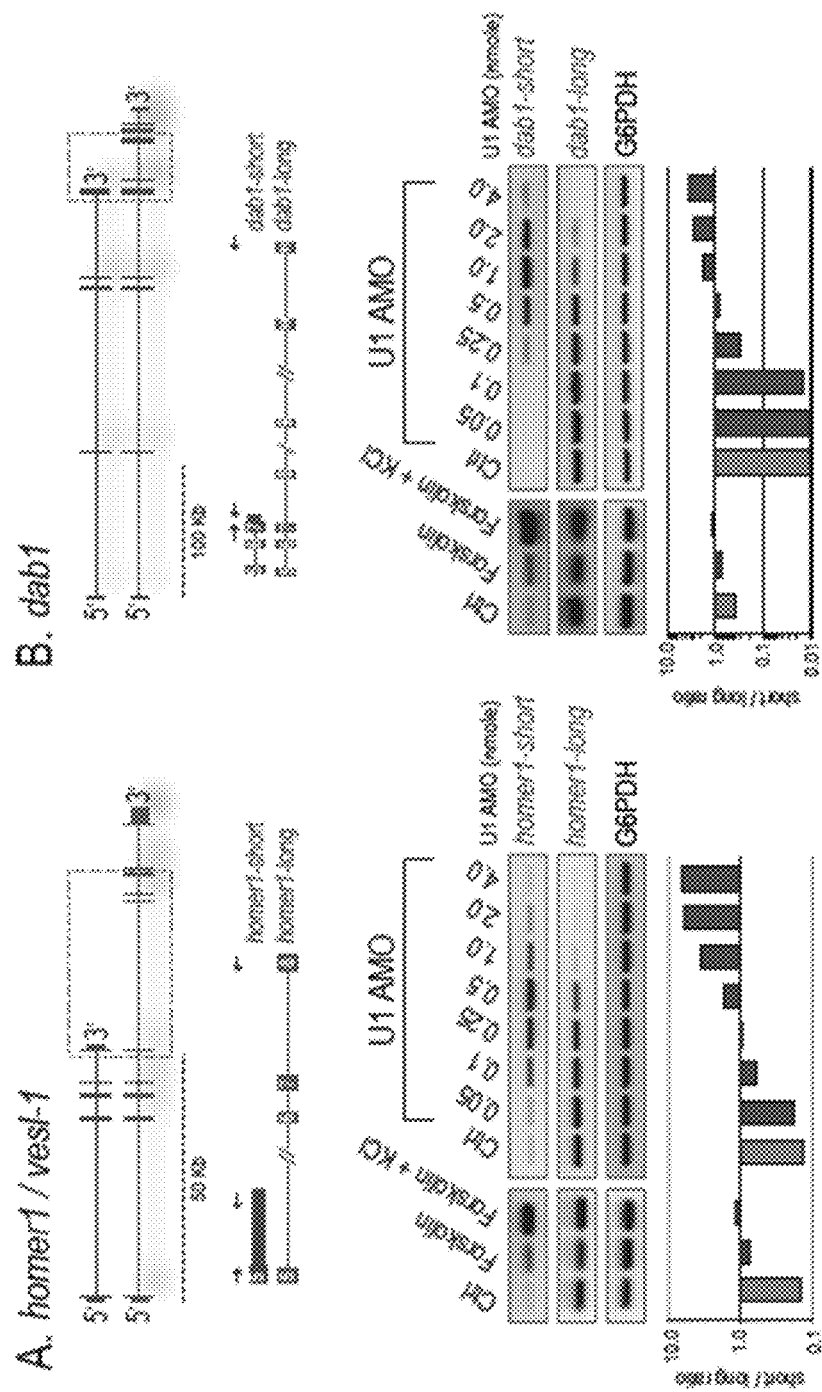
FIG. 5, comprising

Examples consistent with the transcript shortening described herein have been characterized in activated neurons, particularly the homer-1/vesl-1 gene, which plays a critical role in synaptogenesis. Neuronal activation results in a rapid shift (<6 hr) in the processing of the pre-mRNA encoding homer-1, from a full-length (L) to a shorter mRNA (S). Homer-S is produced by an extension of exon 5 and APA in the downstream intron to delete the C-terminal encoding exons (Niibori et al., 2007, Neurosci Res 57:399-410). Using rat PC12 cells, it is shown by RT-PCR that a range of low U1 AMO (0.25-0.5 nmole) dramatically increased the S form and caused a reciprocal dose-dependent decrease in homer-L, mirroring the switch seen upon neuronal activation with forskolin and KCl (FIG. 5A). This shift in ratio of S/L (histogram) was evident even at 0.1 nmol, corresponding to an estimated 10% decrease in U1. Further U1 decrease (1.0-4.0 nmol) caused both forms to disappear, likely as a result of PCPA shifting closer to the TSS. In addition to homer-1, activity-dependent shortening of many other proteins critical for synaptogenesis has been described, including Dab1 (Flavell et al., 2008, Neuron 60:1022-1038). Indeed, in mouse MN-1 cells, Dab1 also displayed a similar isoform shift with U1 decrease (FIG. 5B). Results presented herein suggest that U1 levels can regulate the size of mRNA isoforms produced from many genes.

Transcriptional Up-Regulation in Activated Neurons Creates U1 Shortage

Figure 6:
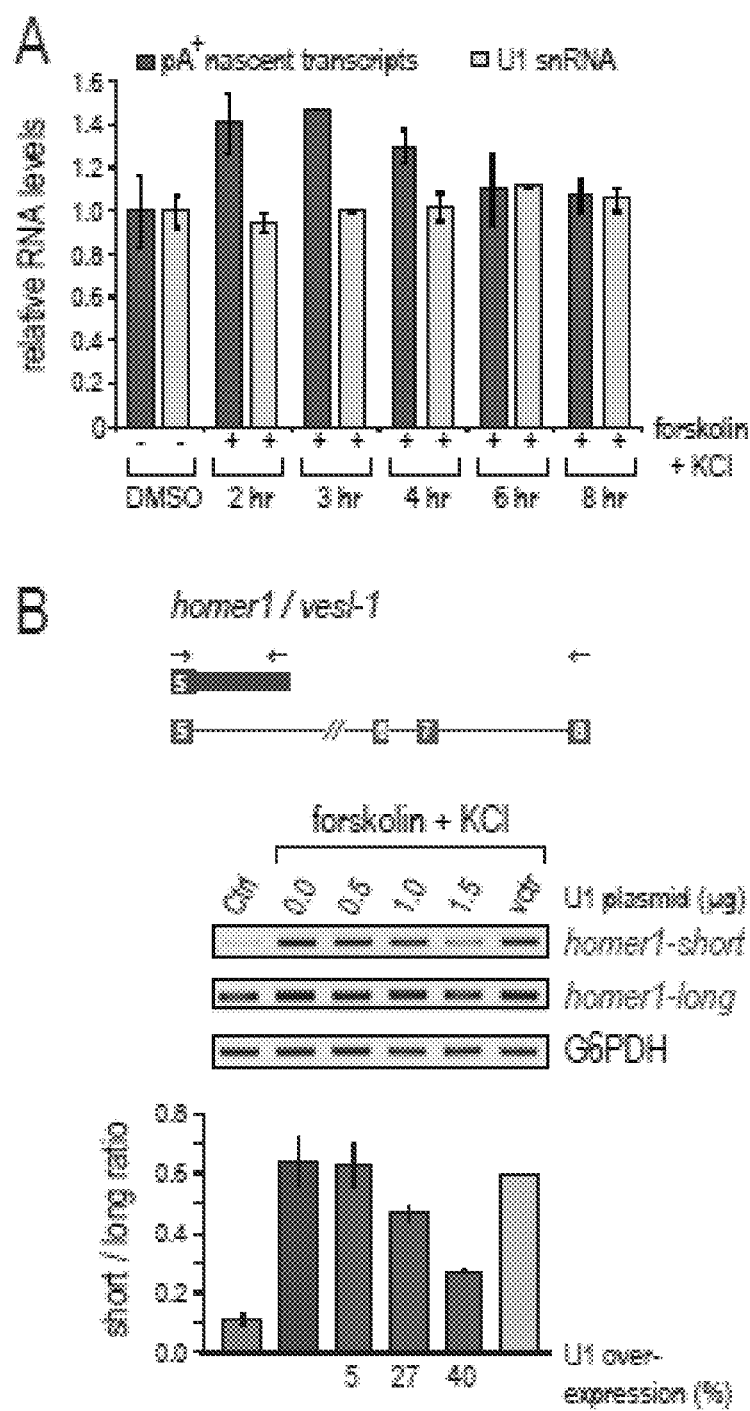
FIG. 6, comprising

Two possible scenarios could potentially explain the shift to usage of more proximal PASs in activated cells if this was indeed due to loss of U1 PCPA suppression. Either U1 levels decreased or the amount of nascent transcripts that it needs to protect increased. To explore these possibilities under physiological conditions, the amount of U1 and pre-mRNAs was determined during neuronal activation (FIG. 6A). Comparing control to activated PC12 cells, U1 was quantified by RT-qPCR, and nascent transcripts were pulse labeled with $5'6'-^{3}H$ uridine for 30 min before RNA isolation and poly(A) RNA selection, followed by scintillation counting to determine the ratio of nascent mRNA to total RNA. This revealed a robust increase in transcriptional output of about 40-50% at 2-4 hrs post activation, whereas U1 levels did not change, creating a significant U1 shortage relative to its targets. This gap returned to baseline at 8 hrs, providing a built-in window of opportunity for rapid global gene expression regulation in response to external stimuli. Notably, Homer-S amounts coincided with the U1 shortage window, rising sharply after activation, peaking at 2-4 hours (~10 fold increase) and returning to near baseline levels at 6-8 hours. In contrast, the predominant form, Homer-L, remains mostly unchanged upon activation.

U1 Over-Expression Inhibits mRNA Shortening in Activated Neurons

While the U1 shortage creates an opportunity for proximal PASs to be used, the switch to shorter isoforms may not necessarily result specifically from loss of U1's function. To address this, it was examined if U1 over-expression could counteract the switch from Homer-L to Homer-S in activated neurons. PC12 cells were transfected with increasing amounts of a U1 snRNA expression vector or an empty vector 24 hr prior to activation. Exogenously expressed U1 quantified by RT-qPCR showed that over-expression (~40% of endogenous U1) prevented the homer-1 switch to the Homer-S isoform in a dose-dependent manner (FIG. 6B). This suggests a role for U1 PCPA suppression in the neuronal activation pathway and demonstrates that altering U1 levels regulates gene expression.

U1 Telescripting

Partial genome tiling arrays previously showed that U1 protection is necessary to prevent drastic premature termination of the majority of nascent pol II transcripts by PCPA from cryptic PASs scattered throughout introns (Kaida et al., 2010, Nature 468:664-668). This activity is referred to as telescripting, as it is necessary for nascent transcripts to extend over large distances. Here, a rapid and versatile high throughput strategy for identifying transcriptome changes, HIDE-seq, and experiments based on the wealth of information it provided, yielded a much greater definition of U1 telescripting, revealing it is not only an evolutionarily conserved measure for ensuring transcriptome integrity, but also a robust mechanism for gene expression regulation. Surprisingly, PCPA position in a given gene varied depending on the amount of available U1. While U1 depletion inhibited splicing and caused PCPA, typically in the first intron, moderate U1 decreases (10-50%) did not inhibit splicing, but caused PCPA farther downstream, trending towards greater distances from the TSS with lesser U1 decrease. Significantly fewer, but still numerous genes were affected by moderate U1 decrease compared to U1 depletion and it was non-destructive, producing shorter mRNAs due to usage of alternative, more promoter proximal PASs rather than the normal PAS at the 3' end of the full-length gene. Thus, telescripting can be modulated by decreasing available U1 over a large range without splicing being compromised, consistent with the idea that there is an excess of U1 over what is required for splicing. It is described herein that telescripting provides a global gene expression regulation mechanism.

Data presented herein demonstrates that the predominant transcriptome changes resulting from incomplete telescripting are various forms of mRNA shortening, including 3'UTR shortening and PCPA in introns. Thus, telescripting plays a major role in determining mRNA length and isoform expression. Indeed, several mRNAs of different lengths can be produced from the same gene by PCPA, corresponding to the degree of U1 decrease (e.g., FIG. 3, GABPB1, UBAP2L). Importantly, PCPA can profoundly modulate protein expression levels and isoforms. While 3' UTR shortening would not change the sequence of the encoded protein, it removes elements, such as microRNA- and hnRNP protein-binding sites, that could be critical for the mRNA's regulation, including its stability, localization, and translational efficiency (Filipowicz et al., 2008, Nat Rev Genet 9:102-114; Huntzinger and Izaurralde, 2011, Nat Rev Genet 12:99-110). In contrast, PCPA in introns would produce an mRNA that encodes a protein lacking the C-terminus or containing a new C-terminal peptide, if the ORF extends into the terminal intron. An additional scenario associated with intronic PCPA is 3' exon switching, also referred to as splicing-dependent APA, reflecting the general view that mechanistically, alternative splicing determines the PAS that is utilized. However, it was shown herein that AMO masking of the alternative terminal exon's PAS prevented its splicing, indicating that splicing into the alternative terminal exon depended on PCPA from this PAS (FIG. 3B). Thus, PCPA can be the primary event in 3' exon switching, revealing an unexpected splicing-independent role for U1 in alternative splicing regulation.

Several lines of evidence strongly suggest that U1 telescripting is a physiological phenomenon. First, over the entire range of U1 AMOs used, numerous PCPA sites coincided precisely with previously detected polyadenylated transcripts, indicating that these cryptic sites are utilized naturally. These include ESTs representing short mRNA isoforms from a wide range of specimen (FIG. 9 and FIG. 12), of which some have been noted as APA from proximal PASs (Lou et al., 1996, Genes Dev 10:208-219; Pan et al., 2006, Gene 366:325-334; Tian et al., 2007, Genome Res 17:156-165). Second, many of the mRNA shortening events resulting from loss of PCPA suppression are indistinguishable from the widespread mRNA shortening observed in activated T lymphocytes and neurons, proliferating cells and cancer cells (Flavell et al., 2008, Neuron 60:1022-1038; Mayr and Bartel, 2009, Cell 138:673-684; Sandberg et al., 2008, Science 320:1643-1647; Zhang et al., 2005, Genome Biol 6(12):R100). Notably, ~33% of the genes that undergo 3' UTR shortening in activated T cells (Sandberg et al., 2008, Science 320:1643-1647) are similarly affected by low U1 AMO in HeLa cells, as are RAB10 and CCND1 (FIG. 2C and FIG. 13), seen in cancer cells (Mayr and Bartel, 2009, Cell 138:673-684). Third, moderate U1 decrease recapitulated precisely hallmark switches to shorter isoforms in a neuronal activation model. Using native inducers (KCl and forskolin), it is shown that U1 decrease alone causes the same isoform switching in both homer-1 and Dab-1 in a dose-dependent manner Representing the best-characterized example, the homer-1 gene switches to an isoform lacking the C-terminal domain-encoding exons, which antagonizes the full-length protein's critical activity in synapse strengthening and long-term potentiation (Sala et al., 2003, J Neurosci 23:6327-6337).

Having relied in these studies on deliberate U1 downregulation, it was considered whether there are physiological circumstances under which U1 levels could become deficient. Given U1's abundance and very long half-life (Sauterer et al., 1988, Exp Cell Res 176: 344-359), it seemed unlikely that its levels would significantly decrease in absolute terms in the short timeframe in which mRNA shortening is observed. An alternative scenario was considered whereby U1 shortage relative to the targets it needs to protect in nascent transcripts could arise simply by an increase in transcriptional output of pre-mRNAs. Supporting this scenario, measurements showed a rapid and transient increase in nascent transcripts of ~40-50% upon neuronal activation, while U1 levels showed little if any change (FIG. 6A). This creates a significant U1 shortage relative to nascent pre-mRNAs, the magnitude of which is in the same range of the AMO experiments. This transcription-driven gap, detectable at 2-4 hr and returning to baseline at 6-8 hr after activation, creates a window of opportunity for APA to occur from proximal PASs due to the transient decrease in telescripting capacity. Importantly, the switch to shorter isoforms during neuronal activation could be antagonized by U1 over-expression in a dose-dependent manner. These data provide further evidence that U1 PCPA suppression is a built in PAS selection mechanism, and thus plays a major role in regulating gene expression during neuronal activation and potentially in response to other physiological stimuli.

The mechanism and factor(s) involved in the mRNA shortening in diverse activation conditions have not been identified (Flavell et al., 2008, Neuron 60:1022-1038; Ji and Tian, 2009, PLoS One 4:e8419; Mayr and Bartel, 2009, Cell 138:673-684; Sandberg et al., 2008, Science 320:1643-1647). However, the remarkable similarities they have with U1 shortage suggest that they also involve loss of U1 telescripting, at least during the initial (immediate/early) phase. Other factors have been described that could also cause a shift to proximal alternative PASs, particularly up-regulation of general polyadenylation and 3' end processing factors, such as Cstf64 (Chuvpilo et al., 1999, Immunity 10:261-269; Takagaki et al., 1996, Cell 87:941-952). However, this requires new protein synthesis and takes many (>18) hours (Shell et al., 2005, J Biol Chem 280: 39950-39961), and therefore cannot explain the rapid switch to proximal PAS, in contrast to U1 shortage, which is immediate upon stimulation and occurs even in the presence of protein synthesis inhibition (Loebrich and Nedivi, 2009, Physiol Rev 89(4):1079-1103). The potential role of U1 and other factors at later times after cell activation and in other cells remains to be determined. Other means of creating U1 shortage, without transcription increase, can be envisioned, such as its sequestration in nuclear structures or by expression of other RNAs to which it could bind.

Figure 7:
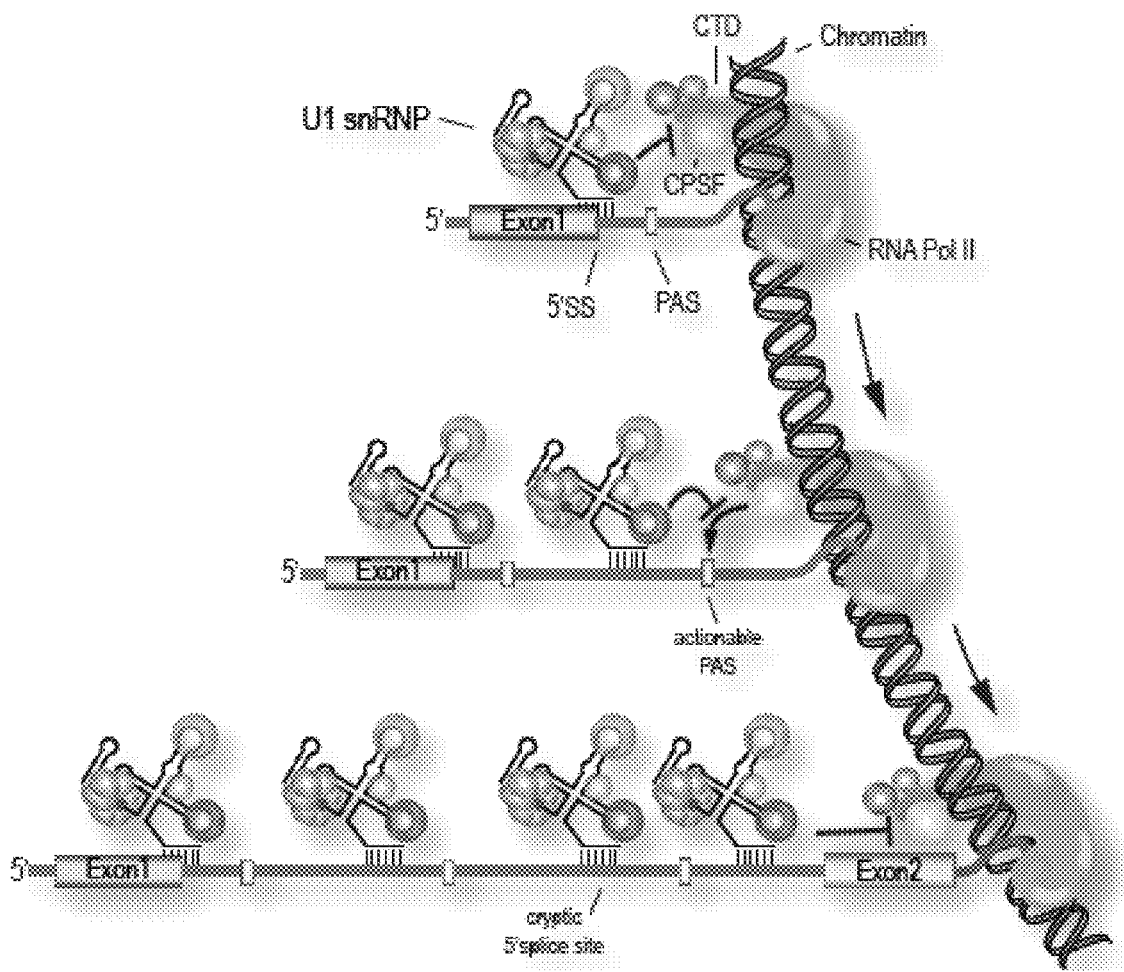
FIG. 7 depicts a model of co-transcriptional PCPA and its suppression by U1. Cleavage and polyadenylation factors (CPSF) associate with pol II TEC and is thus poised for 3'-end cleavage and polyadenylation, but can also cause premature termination (PCPA) from cryptic PASs found throughout pre-mRNAs. U1 is recruited to nascent transcripts by multiple interactions, including base pairing of its 5'-end with cognate pre-mRNA sequences (5' splice site and other) and can suppress PCPA by inhibiting the pol II associated CPSF over <1 kb range. U1 shortage increases the probability of distal PASs remaining unprotected.

A model for U1 telescripting is proposed that could explain its role in mRNA length regulation and isoform switching (FIG. 7). While not wishing to be bound by any particular theory, it is suggested that PCPA occurs co-transcriptionally by the same machinery that carries out normal 3' end cleavage and polyadenylation in the terminal exon of the full-length gene, and is a byproduct of the coupling between transcription and this downstream process (Calvo and Manley, 2003, Genes Dev 17:1321-1327; Dantonel et al., 1997, Nature 389:399-402; McCracken et al., 1997, Nature 385:357-361). CPA factors associate with the pol II TEC (Glover-Cutter et al., 2008, Nat Struct Mol Biol 15:71-78; Hirose and Manley, 1998, Nature 395:93-96) close to the TSS and are therefore poised to process newly transcribed PASs with favorable sequence and structural features (actionable PASs) that it encounters throughout most of the length of the gene. This is normally prevented by U1 snRNP that binds to the nascent transcript. Previous studies have shown that U1 can inhibit polyadenylation of the normal PAS when tethered in its proximity in the terminal exon and in vitro (Ashe et al., 2000, RNA 6(2): 170-177; Fortes et al., 2003, Proc Natl Acad Sci USA 100:8264-8269; Gunderson et al., 1998, Mol Cell 1:255-264; Vagner et al., 2000, RNA 6(2):178-188). U1 is recruited to nascent pol II transcripts, including intronless transcripts, by multiple interactions with the pre-mRNA and RNA processing factors as well as the transcriptional machinery (Brody et al., 2011, PLoS Biol 9:e1000573; Das et al., 2007, Mol Cell 26:867-881; Lewis et al., 1996, Genes Dev 10:1683-1698; Lutz et al., 1996, Genes Dev 10:325-337). In all three organisms studied, PCPA was typically not detected in the first few hundred nucleotides, rising sharply thereafter and peaking ~1 kb from the TSS (FIG. 2D). It is possible that actionable PASs upstream of this point are not utilized because CPA factors may have not yet associated with the TEC (Mayer et al., 2010, Nat Struct Mol Biol 17:1272-1278; Mueller et al., 2004, Mol Cell 14(4):447-456), which depends on pol II's carboxyl terminal domain phosphorylation state (Buratowski, 2009, Mol Cell 36:541-546). While not wishing to be bound by any particular theory, it is suggested that this lag could serve (and may have evolved) to allow U1 binding before transcripts are exposed to CPA, to prevent their early destruction. Consistent with this distance from TSS consideration, PASs in the 5'UTR that are not PCPAed are functional when placed at the 3' end of the gene (Guo et al., 2011, Mol Cell Biol 31:639-651).

Data presented herein also indicated that 5' splice site bound U1 has a limited protective range of up to ~500-1000 nt and therefore would be insufficient to ensure telescripting through larger introns. Complete PCPA suppression could not be provided by U1 from the 5' splice site alone even within this perimeter and plays almost no role in protecting more distal PASs, depending instead on additional U1 bound in introns (FIGS. 4D and 4E). Indeed, introns contain numerous U1 binding sites that do not function as 5' splice site which, without wishing to be bound by any particular theory, is suggested to serve to anchor U1 to protect introns from PCPA. Furthermore, it was found that U1 with a mutated 5' sequence that cannot function in splicing can still function in telescripting (FIG. 4C), supporting the notion of two separate U1 roles. U1's capacity to interact with nascent transcripts directly, even without base pairing (Patel et al., 2007, J Cell Biol 178:937-949; Spiluttini et al., 2010, J Cell Sci 123:2085-2093), enhances its association throughout the pre-mRNA, allowing it to scan the transcript and accelerate the rate with which it can find more stable base pairing sites, including the 5' splice site. Importantly, PAS mutations cause PCPA from downstream intronic PASs (FIG. 4D), suggesting a directional process, consistent with a co-transcriptional mechanism. It is proposed that U1 shortage causes transcript shortening because as co-transcriptional recruitment of U1 to nascent transcripts becomes limiting, it leaves distal PASs less protected, providing a built-in and U1 dose-dependent mechanism for mRNA length regulation and isoform switching.

Example 2

U1 snRNA Over-Expression Reverses Cancer Cells' 3'UTR Shortening and Moderates Aggressive Phenotype Widespread mRNA shortening, resulting from alternative polyadenylation (APA) at more proximal cryptic polyadenylation signals (PASs) in 3' untranslated regions (UTRs) and in introns has been associated with cell proliferation, cancer, activation of immune cells and neurons, and growth of stem cells (Flavell et al., 2008, Neuron 60(6):1022-38; Ji et al., 2009, PLoS One 4(12):e8419; Mayr and Bartel, 2009, Cell 138(4):673-84; Sandberg et al., 2008, Science 320 (5883):1643-7). This striking phenomenon has received particular attention because 3'UTR shortening often removes microRNA (miRNA) binding sites enriched in this part of mRNAs, resulting in loss of miRNA regulation. This typically alleviates the miRNA-mediated translation repression often resulting in strong increase (>10 fold) in the amount of protein produced from the shortened mRNA, including proto-oncogenes (Mayr and Bartel, 2009, Cell 138(4):673-84; Filipowicz et al., 2008, Nat Rev Genet 9(2):102-14). Recent studies identified 3'UTR shortening in >200 genes as a signature of aggressive lung and breast cancer with poor prognoses (Lembo et al., 2012, PLoS One 7(2):e31129). Despite the importance of this phenomenon, the factors(s) that mediate mRNA shortening in cancer, proliferating cells and under diverse activation physiologies have been unknown.

U1 snRNP (U1) is an abundant ribonucleoprotein complex (RNP) comprised of the non-coding U1 snRNA (165 nt in mammals) and specific RNA-binding proteins that function in 5' splice site (ss) recognition, the first step in splicing (Wahl et al., 2009, Cell 136(4):701-18). In recent studies it was observed that U1 snRNP depletion caused premature cleavage and polyadenylation (PCPA) in the majority of pre-mRNAs at cryptic PASs found throughout nascent transcripts (Kaida et al., 2010, Nature 468(7324):664-8). By suppressing PCPA, U1 allows pre-mRNAs to extend farther such that more distal polyadenylation signals (PASs) are used (Berg et al., 2012, Cell 150(1):53-64). This activity is termed telescripting, and it was showed that it is U1 specific to this snRNA and that it is separate from its splicing function. Effective telescripting depends on an abundance of U1, in excess of what is needed for splicing, and even a moderate U1 decrease relative to nascent RNA targets, for example as would occur due to transcriptional up-regulation, could elicit mRNA shortening, including in 3'UTRs (Berg et al., 2012, Cell 150(1):53-64). Thus, changes in telescripting activity could provide a mechanism of APA, which has been largely unknown (Di Giammartino et al., 2011, Mol Cell 43(6):853-66), as well as explain the widespread 3'UTR shortening in cancer.

In the experiments presented herein, U1 levels were modulated in a defined cancer cell system and its consequences for 3'UTR length and cancer phenotype was studied. It is shown herein that U1 over-expression lengthened numerous (>2,100) 3'UTRs already shortened in HeLa cancer cells. Conversely, U1 decrease shortened additional (>700) 3'UTRs. Remarkably, U1 increase attenuated (~50%) cell migration and invasiveness, while its decrease dose-dependently enhanced (~500%) them. Many of the 3'UTR length changes recapitulated cancer-causing miRNA target deregulation in oncogenes. The data presented herein demonstrate that mRNA shortening in cancer can be explained by telescripting deficit and that its modulation by U1 alone could profoundly and bi-directionally modify cancer aggressiveness, thereby indicating that telescripting is a target for moderating tumorigenesis.

The materials and methods employed in this experimental example are now described.

Material and Methods:

Cell Culture, Antisense Morpholino Oligonucleotide (AMO), and U1 Over-Expression Cells were maintained in DMEM (HeLa, A549, MCF-7 and MB-231) supplemented with 10% fetal bovine serum (FBS), 10 units/ml penicillin and 10 µg/ml streptomycin at 37° C. and 5% $CO_2$. U1 and U2 AMO sequences and transfections were as previously described (Kaida et al., 2010, Nature 468(7324):664-8). U1 over-expression was achieved by transfecting HeLa cells for 24 hr with a U1 expression plasmid (1 and 1.5 µg) in pSiren-RetroQ vector (Clontech) using Effectene reagent (Qiagen) according to manufacturer's instructions. The U6 promoter is replaced by the native U1 promoter to drive U1 expression. An empty vector with the same U1 promoter was constructed to be used as a control.

Proliferation Assay

Cell proliferation was measured by using the CellTiter-Glo Luminescent Cell Viability Assay kit (Promega) according to the manufacturer's instructions. The cells were transfected with AMOs or U1 over-expression and seeded in triplicate in 96-well plates at a density of $1 \times 10^4$ cells per well. Cells were incubated in media containing 1% FBS for 3 days and proliferation was measured every 24 hours.

Migration and Invasion Assays

Migration was assessed with the Cytoselect 24-well cell migration assay (Cell Biolabs) and invasion was measured using BD BioCoat Matrigel invasion chambers (BD Bioscience). Briefly, in both assays cells were transfected with AMOs or U1 expressing plasmid, and $5 \times 10^5$ cells/ml per well were seeded in an upper chamber in serum free media. The lower chamber was filled with media containing 10% FBS. After 24 hr, cells in the lower chamber were stained and counted according to the manufacturer's instructions.

Metabolic RNA Labeling, Isolation and RNA-Seq

Cells were labeled for 2 hrs with 250 µM 4-thiouridine added to cells between 6-8 hr after U1 AMO transfection or between 22-24 hrs after transfection with U1-expressing or control plasmids. Total RNA was extracted with Trizol (Invitrogen) and poly(A) RNA purified on Oligotex beads (Qiagen). Free thiols on poly(A) mRNA were reacted with 0.2 mg/ml of biotin-HPDP for 2 hr to label RNA incorporating 4-thiouridine. RNA was then purified on M-280 streptavidin Dynabeads (Invitrogen), cDNA was synthesized using Ovation RNA-Seq System V2 kit (NuGEN) and libraries for Illumina sequencing were constructed using Encore NGS Library System according to the manufacturer's instructions.

Mapping RNA-Seq Reads

RNA-seq reads were aligned to reference genome UCSC/hg19 using Tophat (version 1.3.1) (Trapnell et al., 2009, Bioinformatics 25(9):1105-11) with default settings. Reads per exon were grouped, from which RPKM (Reads Per Kilobase of exon model per Million mapped reads (Mortazavi et al., 2008, Nat Methods 5(7):621-8)) values were calculated. Only genes with RPKM>1 were included in further analyses.

Differential Gene Expression Analysis

The Cuffdiff tool from Cufflinks (Trapnell et al., 2010, Nature Biotechnology 28(5):511-5) (version 1.3.0) was used to identify significantly differentially expressed genes, comparing the log ratio of a gene's expression in two conditions against the log of one. Significantly affected genes were reported with an FDR of 0.05 using Benjamini-Hochberg correction for multiple-testing.

Alternative Splicing Analysis

MISO (version 0.4.1) (Katz et al., 2010, Nat Methods 7(12):1009-15) analysis was performed on aligned RNA-seq data to identify differentially spliced isoforms in experimental samples compared to controls and quantify their expression levels by computing the PSI (Percent Spliced Isoform; $\Psi$) and Bayes factors. Alternative splicing events were filtered by the following criteria: (a) at least 15 inclusion read, (b) at least 15 exclusion read, such that (c) the sum of inclusion and exclusion reads is at least 30, (d) the $|\Delta\Psi|$ at least 0.3 (e) the Bayes factor is at least 10, and (a)-(e) are true in one of the samples.

UTRend Algorithm

For a given gene, the 3'UTR of its longest canonical isoform was extracted from RefSeq genes and the locations of all possible APA sites or transcript 3'ends within this region were mapped using the PolyA_DB UCSC and AceView databases as references. To include potential novel 3'ends not found in any of the aforementioned annotations but present in the dataset, a peak finding algorithm was developed to represent the pattern of 3'UTR mapped sequence reads for a gene. A potential 3'end was inferred as follows: 1) read coverage distribution along the entire 3'UTR was calculated in control and treatment samples separately; 2) the two distributions were merged by MAX function; 3) data were then smoothed by LOWESS and searched for local maximum as peaks. For each annotated and predicted 3'end, the read counts in its upstream 200 nucleotide window were computed as the estimation for the expression level of the mRNA isoform terminating at that 3'end. The relative ratio of expression at proximal to distal peaks, in addition to a p-value, was calculated by Fisher's Exact test using R. Without loss of generality, the lengthening prediction can be equivalent to shortening prediction in the other direction and thus relative ratio >3 and p-value <0.01 were used to predict the trend of 3'UTR length change.

miRNA Targeting Sites Analysis

TargetScan miRNA regulatory sites were downloaded from UCSC Genome browser. The coordinate of each predicted miRNA site was compared to those genes for which the 3'UTR showed changes in length. For FIGS. 14 and 15, only miRNAs that are expressed in HeLa and have been demonstrated to be involved in cancer are shown.

Metabolic Labeling of Proteins

HeLa cells were transfected with U1 or U2 AMO for 8 hours, or with 1.5 µg U1-expression plasmid for 24 hours. Cycloheximide was used as control for complete translation inhibition. Three hours before harvesting, cells were serum starved for 2 hrs, then labeled with [$^{35}$S]methionine Promix (40 µCi/ml) for the last hour. Newly synthesized proteins were lysed by alkaline hydrolysis, precipitated with trichloroacetic acid, captured on filter papers and washed extensively to eliminate unincorporated [$^{35}$S]methionine. Radioactivity was measured by scintillation counting on a TriCarb 2900TR.

The results of the experiments are now described.

Telescripting as a Potential Target for Moderating Tumorigenesis

Figure 22:
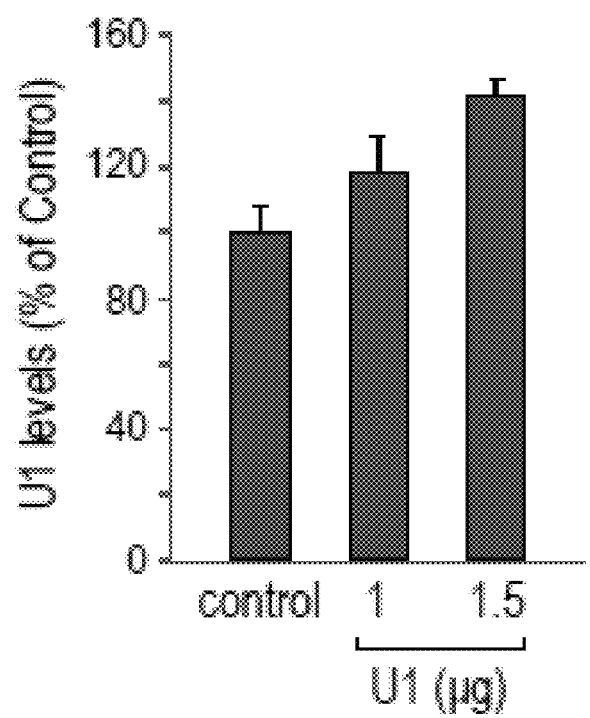
FIG. 22 is a graph depicting the results of experiments demonstrating that transfection of increasing concentrations of U1-expressing construct increases the total level of U1 snRNA. Total U1 levels in transfected HeLa cells were determined by RT-qPCR 24 hours after transfection. RNA input was normalized by 5S rRNA.

To determine if 3'UTR shortening in cancer cells is caused by telescripting deficit, U1 was over-expressed in human cervical carcinoma cells (HeLa) and deep RNA sequencing (RNA-seq) used was used to characterize the resulting sequence changes in polyadenylated RNAs (mRNAs and pre-mRNAs). U1 over-expression of 20% and 40% was achieved by transfecting 1.0 µg and 1.5 µg, respectively, of a plasmid containing the U1 snRNA gene under the control of its native promoter (FIG. 22). The same vector without a U1 gene was used as control (empty vector). For comparison, the effect of decreasing U1 was also examined Based on previous studies, U1 was decreased only moderately, by transfection of low doses of antisense morpholino oligonucleotide complementary to U1 snRNA's 5' end (U1 AMO) (Kaida et al., 2010, Nature 468(7324):664-8; Berg et al., 2012, Cell 150(1):53-64), which occludes U1's 5' 9 nucleotide sequence that is necessary for its activities in splicing and telescripting. U1 AMO transfections (0.1-1.0 nmole) into HeLa cells inactivated ~15-40% of U1 in <8 hr (Kaida et al., 2010, Nature 468(7324):664-8). A dose of 0.25 nmoles was used for the RNA-seq as it produced the maximal phenotype changes described below. As telescripting occurs co-transcriptionally, mRNA length changes would be most readily detected in nascent transcripts. Thus, RNAs were metabolically labeled with 4-thiouridine (Dolken et al., 2008, RNA 14(9):1959-72; Rabani et al., 2011, Nat Biotechnol 29(5):436-42) for 2 hrs, selected and sequenced only nascent polyadenylated transcripts produced in the time window during which U1 levels are altered, as described elsewhere herein.

A summary of the RNA-seq data for U1 over-expression and U1 AMO, compared to their respective controls, is shown in Table 3. Between 95 and 226 million paired-end reads were obtained, of which ~50-60% could be uniquely mapped to the human reference genome (UCSC, hg19) using TopHat (Trapnell et al., 2009, Bioinformatics 25(9): 1105-11). Reads were grouped by RefSeq annotated genes and only those for which a sufficient sequencing depth, calculated from the number of reads per kilobase per million mapped reads (Mortazavi et al., 2008, Nat Methods 5(7): 621-8) (RPKM)>1, were included in further analysis. This consisted of 12,639 genes in U1 over-expression experiments and 9,166 genes in U1 AMO. Using Cufflinks, setting cutoffs of 1.5-fold expression change and p-value <0.01 (Trapnell et al., 2010, Nature Biotechnology 28(5):511-5), 13 genes were up-regulated in U1 AMO as well as 382 and 206 genes in U1 over-expression (1.0 and 1.5 µg, respectively), while 241, 301 and 556 genes, respectively, were down-regulated (Table 4). These values indicate that U1 levels affect transcript stability or transcription efficiency of many genes. Alternative splicing changes were analyzed by MISO, setting filters of $|\Delta\Psi| \geq 0.3$, Bayes factor 10 (Katz et al., 2010, Nat Methods 7(12):1009-15). This detected ~5-250 each of several types of alternative splicing events, including skipped exons, mutually exclusive exons, retained introns, alternative 5' or 3' splice sites, and alternative first or last exons (Table 5).

TABLE 3

Statistics of RNA-seq

| MAPPING STATISTICS | CTRL AMO | U1 AMO | CRTL (empty vector) | U1 over-expression (1 µg) | U1 over-expression (1.5 µg) |
|---|---|---|---|---|---|
| Total reads | 97,702,429 | 94,980,514 | 226,028,904 | 185,947,498 | 207,313,315 |
| Mapped reads | 51,137,948 | 49,896,982 | 136,133,739 | 92,804,677 | 123,786,737 |
| % of mapping | 52.34% | 52.53% | 60.23% | 49.91% | 59.71% |

A summary of the total number of reads, mapped reads and percentage of mapped reads compared to the total for each RNA-seq sample.

TABLE 4

Differential expression analysis

| DIFFERENTIAL EXPRESSION (±1.5 fold change, P < 0.01) | U1 AMO | U1 over-expression (1 µg) | U1 over-expression (1.5 µg) |
|---|---|---|---|
| Up-regulated transcripts | 13 | 382 | 206 |
| Down-regulated transcripts | 241 | 301 | 556 |

The table reports the number of up-regulated and down-regulated transcripts following U1 AMO and U1 over-expression treatment. The analysis was performed using Cufflink differential expression software (fold change >1.5 or <−1.5 and p-value <0.01).

TABLE 5

MISO analysis of alternative splicing changes

| SPLICING EVENTS ($|\Delta\Psi| \geq 0.3$) | U1 AMO | U1 over-expression (1 µg) | U1 over-expression (1.5 µg) |
|---|---|---|---|
| Exon skipping/inclusion | 38 | 130 | 208 |
| Alternative 5' splice site | 5 | 28 | 98 |
| Alternative 3' splice site | 5 | 41 | 40 |
| Mutually exclusive exon | 1 | 7 | 14 |
| Intron retention | 12 | 100 | 131 |
| Alternative first exon | 45 | 144 | 230 |
| Alternative last exon | 62 | 143 | 263 |

The various classifications of splicing events identified using the MISO software and applying a $|\Delta\Psi| \geq 0.3$, Bayes factor $\geq 10$, and exclusion and inclusion reads $\geq 15$ as filters are reported.

Figure 23:
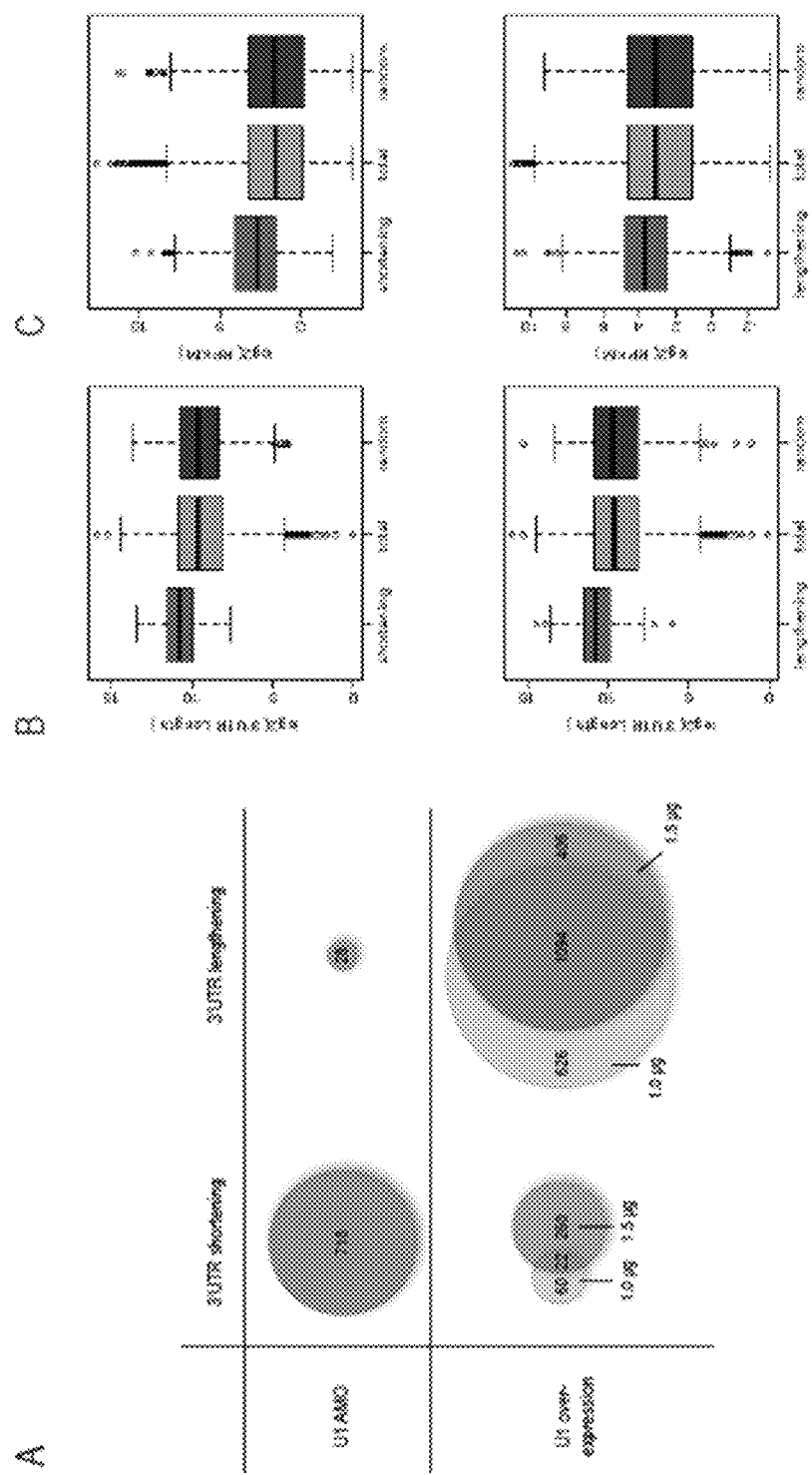
FIG. 23, comprising

Although RNA for sequencing was oligo(dT) selected, and thus samples are expected to vastly over-represent mRNAs with poly(A) tails, the low abundance of 3' non-genomically encoded poly(A)-containing reads from RNA-seq limits the ability to identify 3'ends. As a more general approach to identify length changes, UTRend was developed, a bioinformatic pipeline which uses a local regression model to detect RNA-seq reads peaks. The relative ratio of proximal to distal peak intensity was used to analyze the pattern of 3'end length change for mRNA isoforms produced from any given gene. A stringent cutoff of distal to proximal ratio >3 and p-value <0.01 indicates shortening of 3'UTR in the experimental sample compared to control, while those where the proximal to distal ratio >3 correspond to 3'UTR lengthening. UTRend revealed that U1 over-expression increased 3'UTR length in 1720 and 1500 genes for 1.0 and 1.5 µg, respectively. A large proportion of these, 1094, overlapped at both U1 over-expression levels, a strong validation of the RNA-seq data from separate biological experiments. Only a relatively small number of genes (82 and 282, at 1.0 and 1.5 µg, respectively) had 3'UTR shortening with U1 over-expression. In contrast, U1 AMO caused 3'UTR shortening in 718 genes while only 28 genes had longer 3'UTRs (FIG. 23A). The vast majority of shortened genes in U1 AMO were different from those that became longer in U1 over-expression (overlap of 78 genes). While UTRend underestimates the number of affected genes because it does not include UTRs with single peaks, it is nevertheless clear that the scope of the 3'UTR length changes is major. Generally, shortened genes were highly transcribed and had longer than average 3'UTRs (FIG. 23B-23C). Furthermore, there was no correlation between the position where shortening occurred and the distance from the transcription start site, indicating that as yet unknown factors differentiate 3'UTRs from the rest of the pre-mRNA, making it more susceptible to cleavage and polyadenylation during telescripting shortage.

From the lengthening elicited by U1 over-expression it is inferred that relative to their potential length, i.e., if HeLa were quiescent, a combined 2126 genes from the two U1 over-expression doses in these cancer cells already have mRNAs with shortened 3'UTRs. Conversely, a greater telescripting deficit elicited by U1 AMO shortens 3'UTRs of an additional 718 genes. Notably, there was insignificant overlap between genes in which splicing changes occurred and those in which 3'UTR length was affected, providing additional evidence that splicing and telescripting are separate U1-dependent events. While the number of each type of alternative splicing changes, transcript level effects, and 3'UTR length changes were assessed by different methods and parameters and cannot be directly compared, 3'UTR length changes constituted the single most prevalent type of mRNA change resulting from U1 abundance variation.

Figure 14:
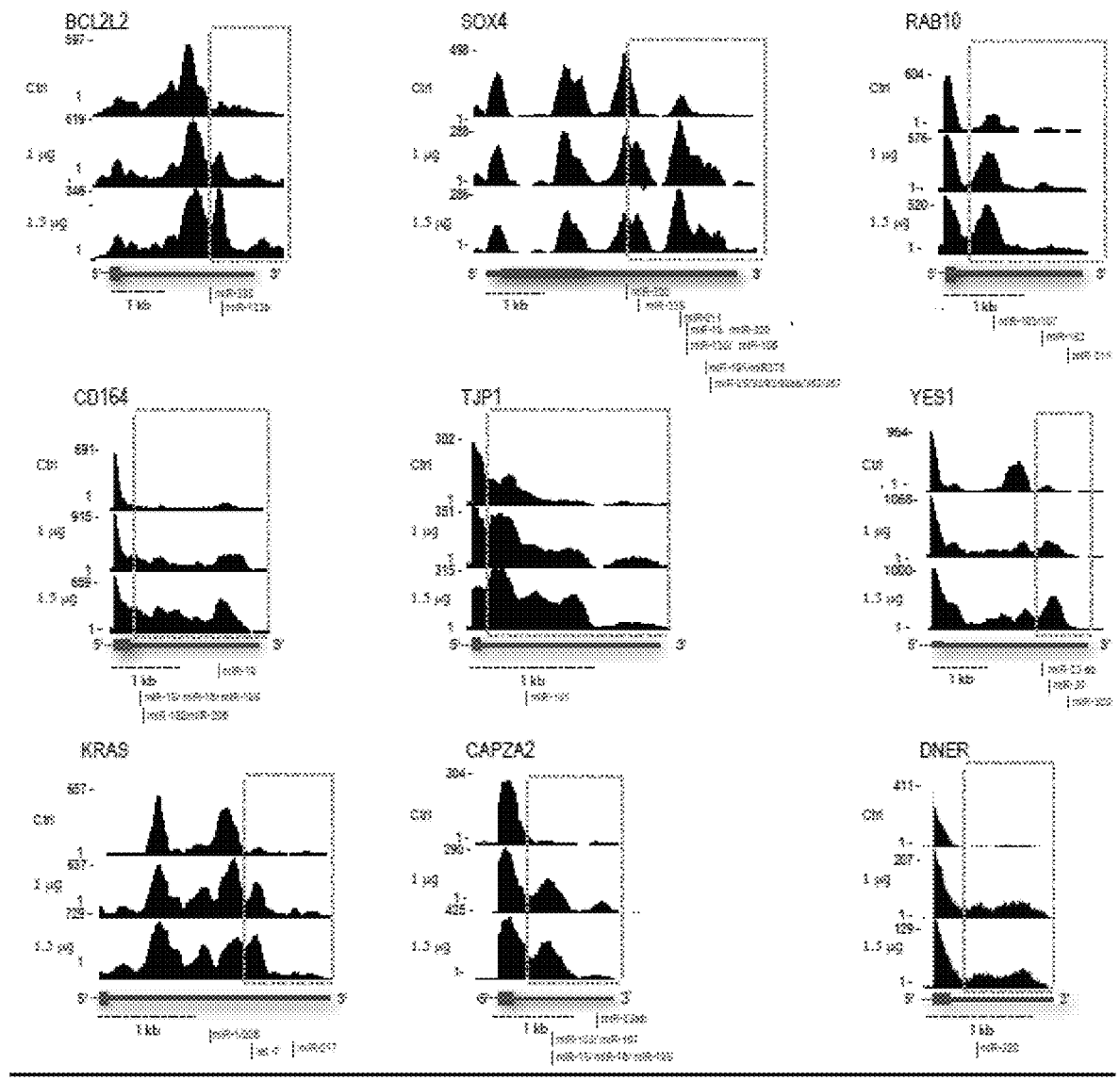
FIG. 14 depicts the results of experiments demonstrating that U1 over-expression increases the 3'UTR length globally. Cells transfected with control empty vector or U1 expression plasmids (1 µg and 1.5 µg, 24 hr) were labeled with 4-thiouridine to select nascent transcripts. RNA-seq maps of representative genes show the last exon with dotted boxes indicating switch towards longer 3'UTRs. miRNA target sites that are involved in cancer and expressed in HeLa are shown.
Figure 15:
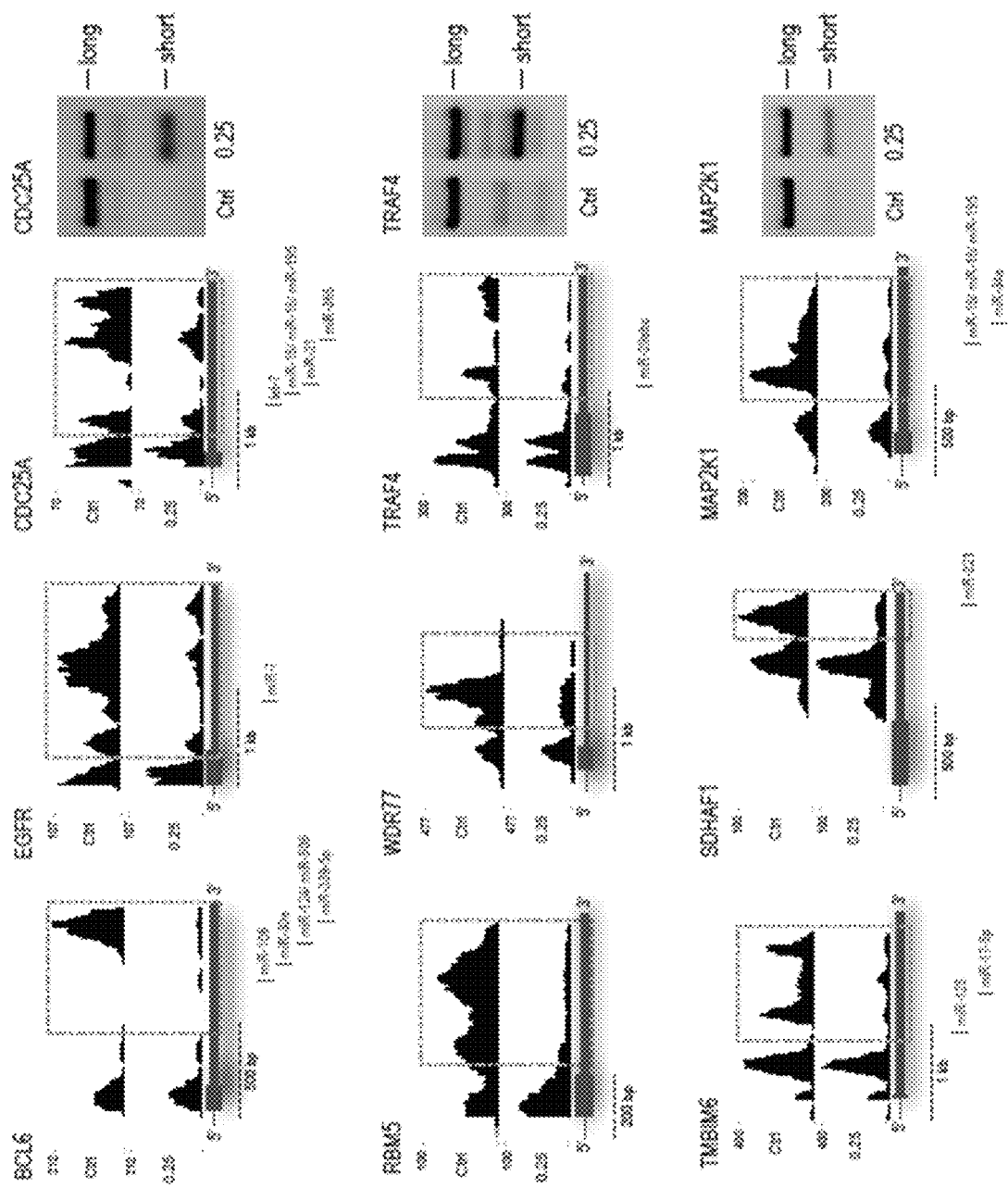
FIG. 15 depicts the results of experiment demonstrating that moderate decrease of U1 causes global mRNA shortening of 3'UTRs. Cells transfected with control or U1 AMO (0.25 nmole, 8 hr) were labeled with 4-thiouridine to select and sequence nascent transcripts. RNA-seq maps of representative genes show the last exon with dotted boxes indicating regions of shortening in the 3'UTR. 3'RACE using nested PCR was performed to detect the polyadenylated mRNAs. miRNA target sites are listed as in FIG. 14.

Examples of 3'UTR lengthening and shortening in the RNA-seq, as well as representative validations by 3'RACE, are presented in FIGS. 14 and 15. Zooming in on the last exon, the patterns of read coverage for U1 over-expression (FIG. 14) or U1 AMO (FIG. 15) compared to their respective controls, highlight the dramatic increase or dose-dependent decrease of reads in the downstream region (dotted boxes), respectively. Length changes are reflected both by the appearance (FIG. 14) or disappearance (FIG. 15) of the distal peak(s) and by a shift in the ratio of distal to proximal peaks (e.g. SOX4). Note that the shift to longer 3'UTRs often was more pronounced with increasing amounts of U1 over-expression. Remarkably, in several transcripts for U1 over-expression, reads extended beyond the previously described canonical 3'end of genes (e.g. BCL2L2), suggesting that telescripting plays a major role in determining transcription termination. Also indicated in FIGS. 14 and 15 are TargetScan predicted sites for miRNAs expressed in HeLa, as loss or restoration of miRNA regulation is one of the important consequences of the UTR length changes.

Figure 16:
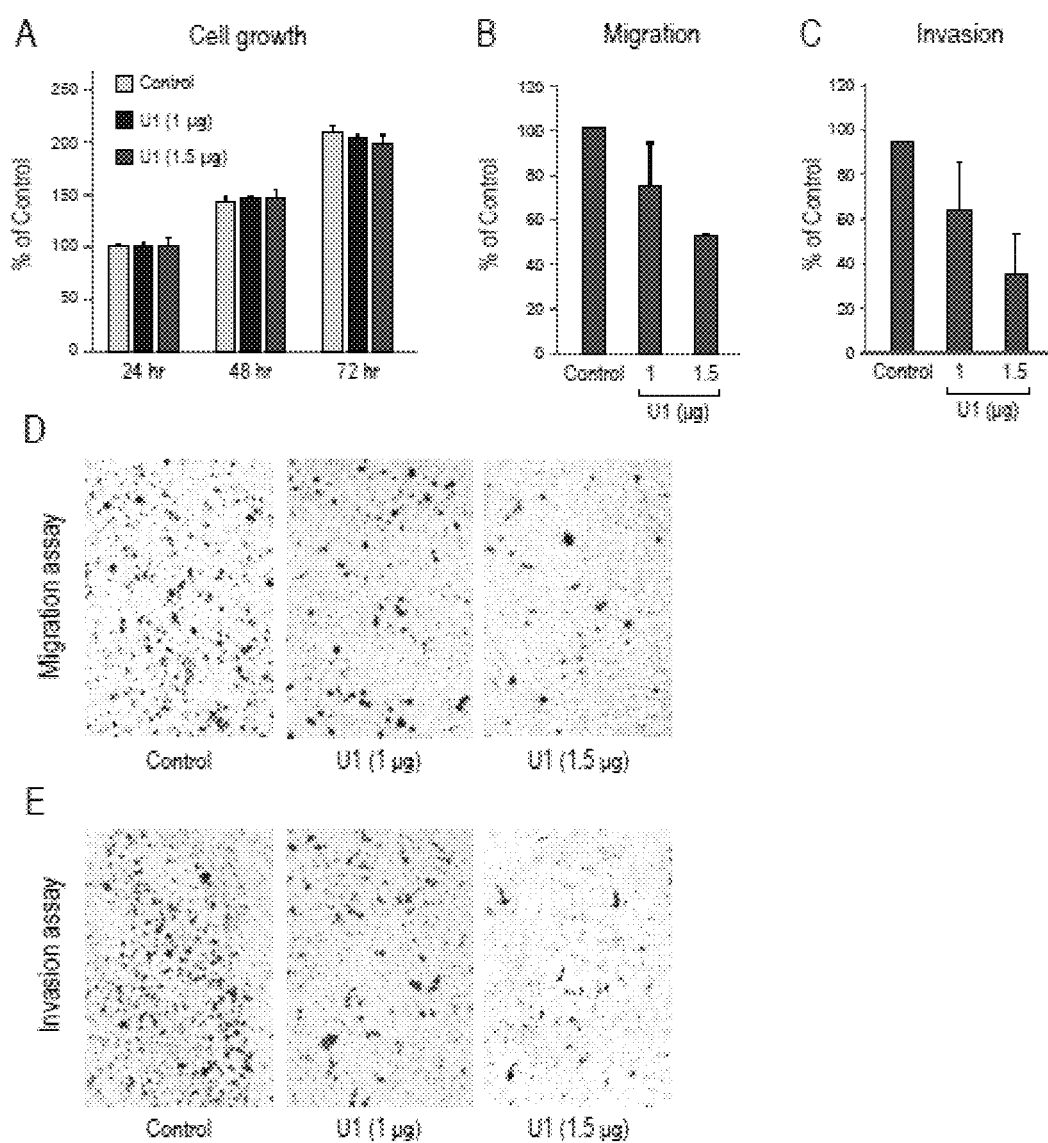
FIG. 16, comprising

It was next examined what effect increasing telescripting has on key features of cancer cell behavior, including cell growth rate, motility and invasiveness, using established quantitative in vitro assays. Over-expression of U1 in Hela cells had no effect on cell proliferation or on viability for up to 72 hrs compared to an empty vector control (FIG. 16A). Surprisingly, however, U1 increase significantly and dose-dependently diminished cell migration (25-50%), measured after 24 hrs by a standard assay used to determine the number of cells that traversed a porous polycarbonate membrane in response to a chemo-attractant (higher serum concentration) (Kramer et al., 2012, Mutat Res, 752(1):10-24; Tsujii et al., 1998, Cell 93(5):705-16). Another key measure of oncogenicity is the ability of the tumor cells to metastasize, which in addition to migration, requires an ability to 58-72% and increased invasion of A549 and MB-231 by 53-64%. While not wishing to be bound by any particular theory, the lower magnitude of the effects compared to HeLa could reflect cell-specific differences, including transfection efficiency, but it is also noted that these cancer cell lines showed greater aggressiveness at baseline. In order to reliably discern changes post-transfection, 6-fold fewer cells were plated compared to HeLa, thereby decreasing the likelihood of observing further increases in aggressiveness. Similar to HeLa, U1 over-expression attenuated the migration and invasion of these cells lines by ~50% compared to the control levels (Table 6). Therefore, the effect of U1 level changes on cancer cell oncogenicity is a general phenomenon.

TABLE 6

Migration and invasion measurements in additional cancer cell lines

| | U1 AMO (0.25 nmole) | | | | | U1 over-expression | | | | | | |
|---|---|---|---|---|---|---|---|---|---|---|---|---|
| | Migration index | Invasion index | Proliferation (% increase) | | | Migration index (% of ctl) | | Invasion index (% of ctl) | | Proliferation (% increase) | | |
| Cell lines | (% of ctl) | (% of ctl) | 24 hr | 48 hr | 72 hr | 1 µg | 1.5 µg | 1 µg | 1.5 µg | 24 hr | 48 hr | 72 hr |
| HeLa (cervical cancer) | 500 | 463 | 0 | 38 | 38 | 74 | 52 | 67 | 37 | No effect | | |
| A-549 (lung adenocarcinoma) | 172 | 164 | 0 | 0 | 15 | 66 | 47 | 92 | 91 | No effect | | |
| MCF-7 (breast adenocarcinoma) | 158 | n/a | 0 | 10 | 12 | | n/a | | | | | |
| MB-231 (breast adenocarcinoma) | 170 | 153 | 0 | 5 | 7 | 57 | 54 | 63 | 72 | No effect | | |

The effect of U1 level changes on cancer behavior was tested on several additional cell lines. The table summarizes the proliferation, migration and invasion index for treated cells compared to control after U1 AMO or U1 over-expression (both 1 and 1.5 µg).

traverse a layer of basement membrane extracellular matrix (e.g. Matrigel) (Albini et al., 1987, Cancer Res 47(12):3239-45; Albini and Noonan, 2010, Curr Opin Cell Biol 22(5): 677-89). U1 over-expression also strongly decreased invasiveness by 25-65% in a dose-dependent manner (FIGS. 16B-16E).

Figure 17:
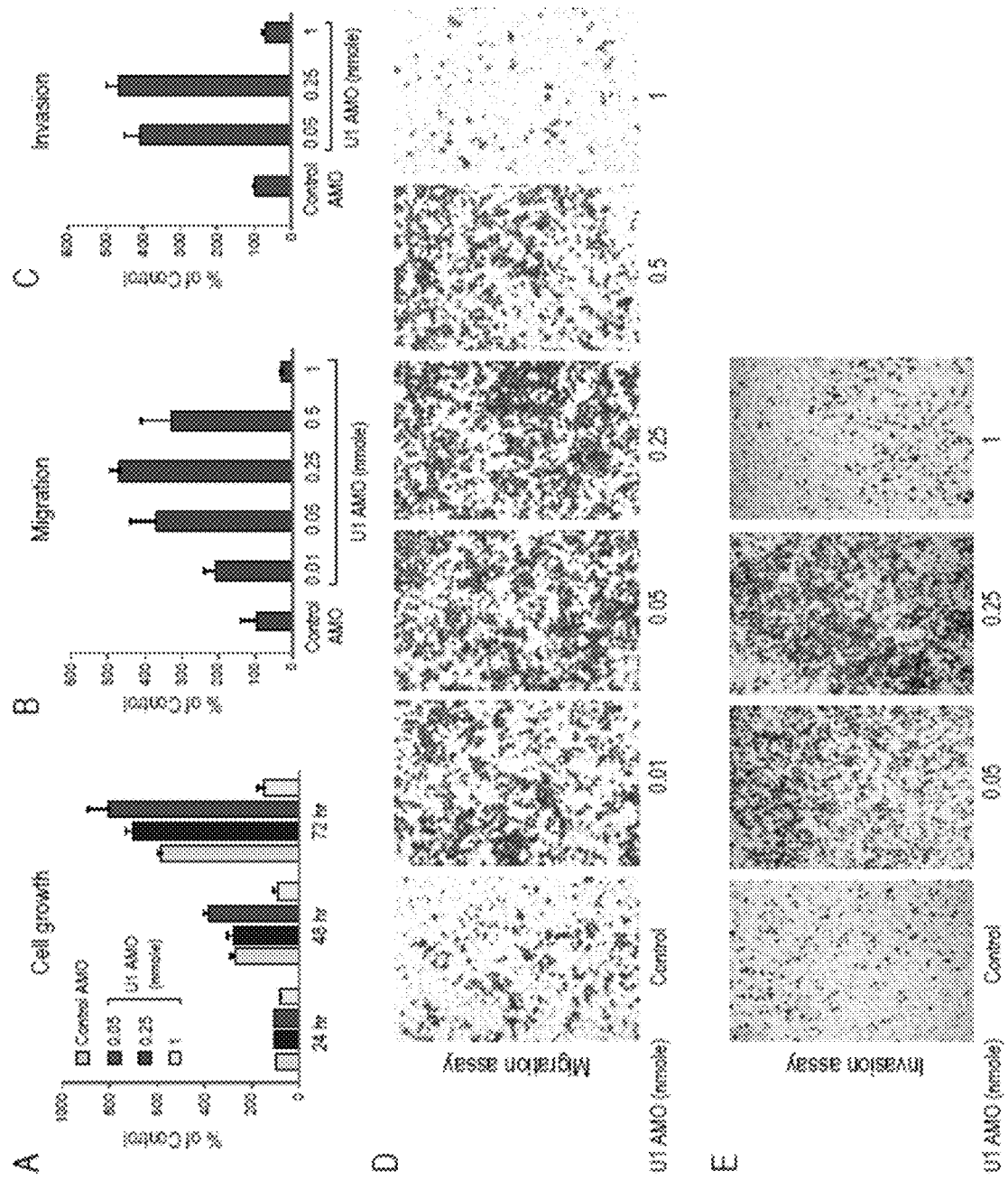
FIG. 17, comprising
Figure 24:
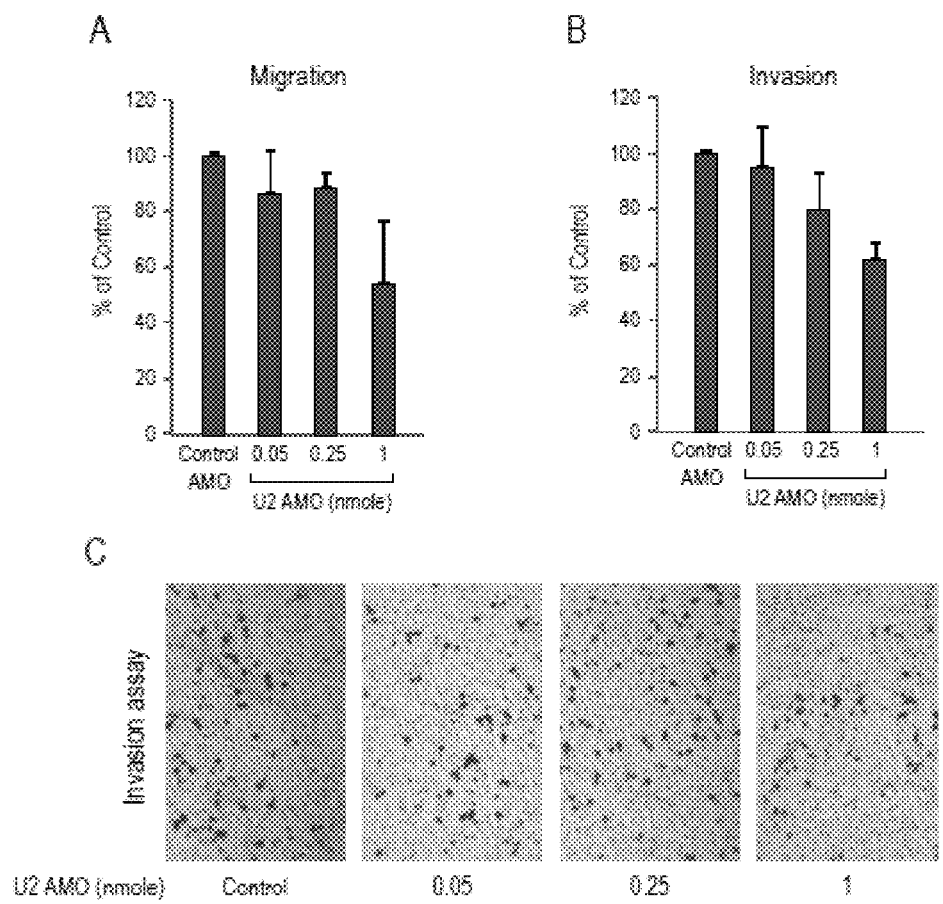
FIG. 24, comprising

The effect of moderate U1 level decrease was also examined in the same assays. Within the low U1 AMO dose range (0.05-0.25 nmole) there was no effect on HeLa cell proliferation after 24 hrs (FIG. 17). A moderate (~35%) increase in cell number compared to control AMO was observed after 2-3 days at 0.25 nmole U1 AMO. Cell growth was inhibited at the higher U1 AMO dose (1.0 nmole), where more drastic mRNA shortening (e.g., in early introns) and some splicing inhibition was evident (Berg et al., 2012, Cell 150(1):53-64). Remarkably, low U1 AMO levels (0.05-0.25 nmole) caused a 400-500% enhancement of cell migration in 24 hrs (FIGS. 17B and 17D). Since the identical U1 AMO dose had no effect on cell number at the same time-point (FIG. 17A), this reflects a true increase in migration activity. A dramatic increase in invasiveness (400-500%) was also observed, similar in dose-dependency to that observed for migration, with peak activity at 0.25 nmole U1 AMO (FIGS. 17C and 17E). As a control, the same experiments were performed with U2 AMO, which interferes with this snRNP's function in splicing. No enhancement was seen in any of the activities measured, indicating that the effects on oncogenicity are specific to U1's telescripting function (FIG. 24).

Figure 21:
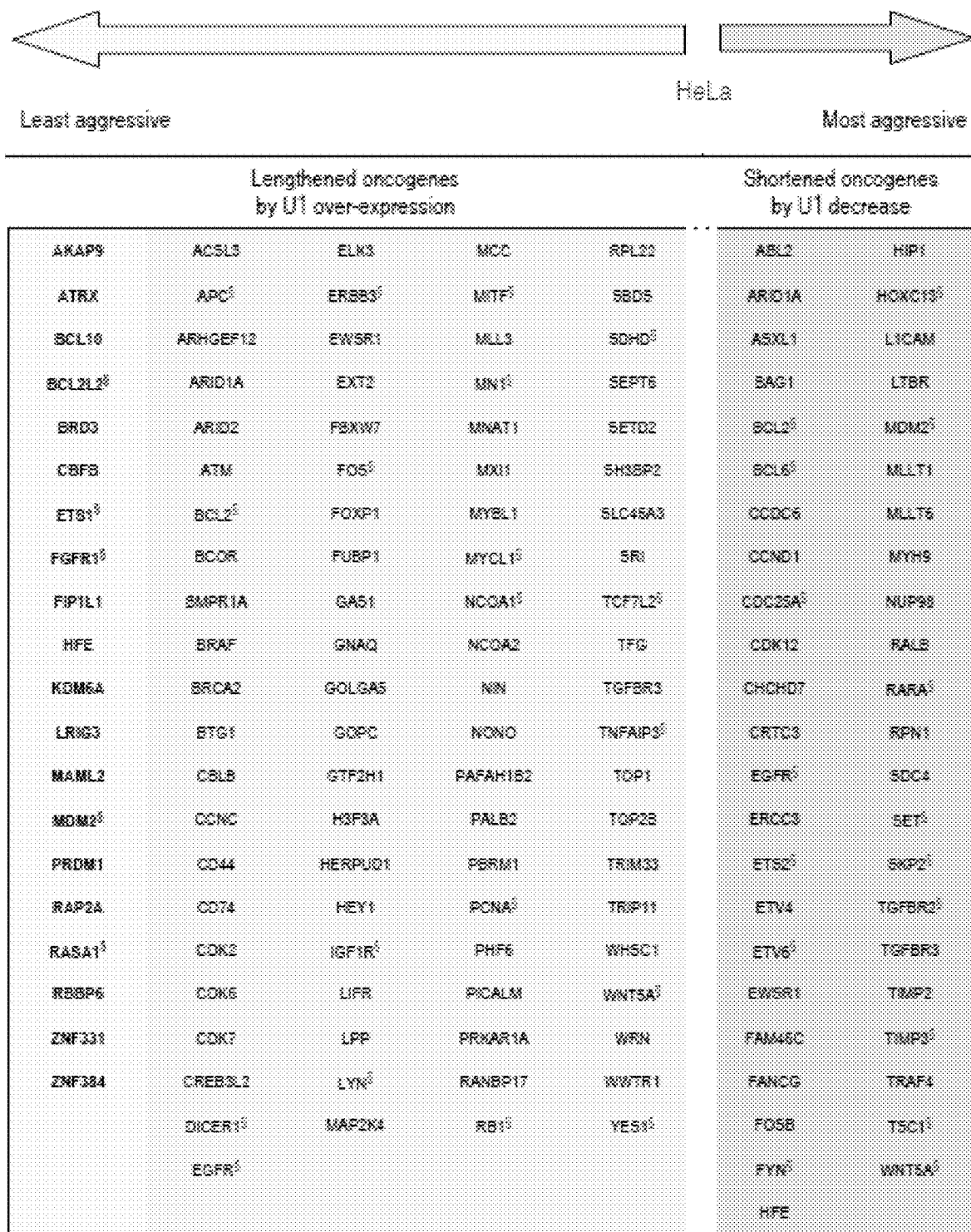
FIG. 21 depicts a list of cancer genes affected by changes in U1 telescripting activity in HeLa cells. U1 AMO (0.25 nmole) treatment results in 45 oncogenes with shortened 3'UTRs compared to control HeLa, while the already shortened UTRs of 85 and then additional 20 oncogenes is restored with increasing level of U1 snRNA expression.

Similar effects were also observed in other cancer cells tested, including human lung adenocarcinoma (A549) and breast adenocarcinomas (MCF-7 and MB-231). U1 AMO enhanced migration of A549, MCF-7 and MB-231 by Seeking potential explanation for the cancer aggressiveness changes, the genes where 3'UTR length changes were detected was analyzed. As expected for such a large number of genes, gene ontology and pathway analysis (DAVID) (Huang 2009, Nat Protoc 4(1):44-57) showed that 3'UTR shortening affected genes of widely diverse functions. Nevertheless, genes involved in cancer pathways were significantly enriched (Table 7). Thus, two cancer gene databases were interrogated: Sanger (Futreal et al., 2004, Nat Rev Cancer 4(3):177-83) and UCSF, which include proto-oncogenes whose up-regulation by various mechanisms, including mutation, chromosomal translocation, or loss of miRNA repression, is linked to cancer. This revealed that 142 of 456 cancer genes in these databases that are expressed in HeLa had their 3'UTRs affected by U1 level changes. FIG. 21 lists these genes according to the U1 level that caused their 3'UTR shortening (U1 AMO; 45 genes) or reverted their already shortened 3'UTR to longer forms (85 and 78 for 1 and 1.5 µg, respectively). These data show that each incremental decrease in U1 level causes 3'UTR shortening in an increasing number of oncogenes and a correspondingly more aggressive cancer phenotype. The affected genes listed in FIG. 21 and Table 7 have known functions in cancer initiation and progression, including cell cycle regulation (CDC25A, SKP1), apoptosis (BAG1, BCL2), cell adhesion (CD164, TJP1), motility (ACTN1, FAP), extracellular matrix remodeling (TIMP2, TIMP3), signaling (WNTSA, EGFR), transcription (RARA, NFKB1), metastasis (EWSR1, APC, MDM2), and tumor progression (SLCA16A1, CAPZA2).

TABLE 7

DAVID pathway analysis

| TERM | AFFECTED GENES | FOLD ENRICHMENT | BENJAMINI |
|---|---|---|---|
| PATHWAYS IN CANCER | WNT5A, FGFR1, PTGS2, ARNT2, TFG, NFKB1, TCF7L2, CDC42, FOS, CUL2, BCL2, SLC2A1, CASP8, RALB, RHOA, RARA, FGF2, TRAF4, APC, COL4A4, EGFR, DVL3, IL6, CTBP2, MAP2K1, BRAF, TGFBR2, FZD1, SKP2, BRCA2, FZD5, BIRC3, COL4A6, CDK2, CCDC6, GSK3B, VEGFA, MDM2, LAMC1, 1KBKB | 13.9 | $3.57 \times 10^{-30}$ |
| MAPK SIGNALING PATHWAY | FGFR1, GNA12, PPP3R1, NFKB1, SRF, ATF2, HSPA1L, CDC42, FOS, DUSP14, MAP3K2, PPP3CA, CHP, RAPGEF2, FGF2, EGFR, MAP2K1, BRAF, TAOK1, TAOK3, TGFBR2, TAB2, DUSP4, MAP4K4, DUSP3, RPS6KA3, ARRB2, DUSP1, IKBKB, GADD45A, DUSP6 | 14.6 | $7.27 \times 10^{-24}$ |
| WNT SIGNALING PATHWAY | WNT5A, DVL3, CTBP2, VANGL1, PPP2R5C, FZD1, PPP3R1, FZD5, TCF7L2, SENP2, CSNK2A1, GSK3B, PPP2CA, NFAT5, RHOA, LRP6, CAMK2D, PPP2R5E, S1AH1, PPP3CA, CHP, TBL1X, APC | 19.1 | $3.39 \times 10^{-20}$ |
| REGULATION OF ACTIN CYTOSKELETON | EGFR, GNA13, FGFR1, MAP2K1, BRAF, MYLK3, WASF1, GNA12, SSH2, ABI2, ACTN1, MYH9, ARHGEF12, PPP1CB, NCKAP1, CDC42, DOCK1, ITGB8, RHOA, CYFIP1, FGF2, F2R, APC | 14.1 | $2.94 \times 10^{-17}$ |
| ADHERENS JUNCTION | EGFR, PTPRJ, FGFR1, WASF1, TGFBR2, ACTN1, CTNND1, FER, ACP1, TCF7L2, CDC42, TJP1, CSNK2A1, FYN, RHOA, PTPN1, YES1, INSR | 23.2 | $3.66 \times 10^{-17}$ |
| FOCAL ADHESION | EGFR, COL4A4, CAV1, BRAF, MAP2K1, MYLK3, ACTN1, BIRC3, PPP1CB, COL4A6, CDC42, PDPK1, DOCK1, FYN, ITGB8, GSK3B, BCL2, VEGFA, RHOA, LAMC1 | 13 | $2.22 \times 10^{-14}$ |
| CELL CYCLE | ANAPC13, YWHAB, SKP2, PRKDC, CDK7, MCM4, SMC3, CDK2, CDC25A, RAD21, YWHAH, GSK3B, YWHAQ, MDM2, SMC1A, GADD45A, STAG2 | 12.2 | $6.55 \times 10^{-12}$ |
| TIGHT JUNCTIONS | F11R, PARD6B, MAGI3, VAPA, CNKSR3, PRKCI, ACTN1, MYH9, CDC42, TJP1, CSNK2A1, PPP2CA, RHOA, YES1, PPP2R2A | 14.1 | $2.49 \times 10^{-11}$ |
| APOPTOSIS | IRAK1, PPP3R1, NFKB1, BIRC3, CAPN1, CASP7, BCL2, RIPK1, PRKAR1A, CASP8, CHP, PPP3CA, IKBKB | 15.9 | $4.43 \times 10^{-10}$ |
| P53 SIGNALING PATHWAY | EI24, SERPINB5, SHISA5, CASP8, MDM2, SIAH1, RCHY1, PMAIP1, PERP, SESN2, GADD45A, CDK2 | 16.5 | $1.01 \times 10^{-9}$ |

The cancer related terms identified by DAVID analysis of enriched KEGG pathways are shown in the table. The affected genes for each category are shown as well as the fold enrichment. p-values were corrected for multiple testing using the Benjamini-Hochberg method.

Numerous examples of cancers due to oncogene up-regulation resulting from loss of miRNA repression, either because the relevant miRNA is down-regulated or its target in the 3'UTR has been removed, have been described (Ebert and Sharp, 2012, Cell 149(3):515-24; Mendell and Olson, 2012, Cell 148(6):1172-87; Nana-Sinkam and Croce, 2011, Mol Oncol 5(6):483-91). Importantly, U1 level changes recapitulated the same miRNA 3'UTR target elimination or restoration in many genes (FIGS. 14, 15 and 21). For example, shortening in 3'UTRs of CCND1 (cyclin D1) and RAB10 (member of RAS oncogene family) is found in numerous cancer cell lines, which among many others, removes target sites for miRs-15/16 and miRs-103/107, respectively, resulting in a dramatic protein level increase of these oncogenes (Lin et al., 2012, Nucleic Acids Res 40(17): 8460-71; Mayr and Bartel, 2009, Cell 138(4):673-84). As shown in FIG. 14, 3'UTR of RAB10 is already shortened in HeLa cells, and U1 over-expression reverses the 3'UTR shortening and restores the corresponding miRNA binding sites. For CDC25A, an essential phosphatase for the G1-S transition, 3'UTR shortening eliminates miRNA binding sites, including let-7, miR-15 and miR-21 (FIG. 15). An increase in CDC25A protein due to alleviation of miRNA-mediated repression exacerbates hepatic cyst formation and colon cancer (Johnson et al., 2007, Cancer Res 67(16):7713-22; Wang et al., 2009, Cancer Res 69(20):8157-65; Lee et al., 2008, J Clin Invest 118(11):3714-24). Epidermal growth factor receptor (EGFR) is over-expressed in a variety of tumors (Arteaga, 2001, J Clin Oncol 19(18 Suppl):325-405) and U1 AMO removes the miR-7 target sequence in the 3'UTR (FIG. 15), which causes increased invasiveness and metastasis (Webster et al., 2009, J Biol Chem 284(9):5731-41). It was found that telescripting also regulates 3'UTRs of Src non-receptor tyrosine kinases (YES 1, FYN, and LYN), which are downstream targets of EGFR involved in signaling for cell growth and tight junction formation, and highly oncogenic when their regulation by miRNA is disrupted (FIG. 21) (Majid et al., 2011, Cancer Res 71(7):2611-21; Sommer et al., 2005, J Steroid Biochem Mol Biol 97(3): 219-29). Similarly, a KRAS 3'UTR polymorphism included in the same region that is removed by U1 decrease, impairs let-7 binding and is prognostic for breast cancer aggressiveness (Paranjape et al., 2011, Lancet Oncol 12(4):377-86) (FIG. 14). miRNAs down-regulation has also been shown to cause cancer due to loss of repression of specific mRNA that encodes oncogenes (Nicoloso et al., 2009, Nat Rev Cancer 9(4):293-302). For example, breast cancer cell migration and invasion are enhanced by miR-339-5p down-regulation (Wu et al., 2010, BMC Cancer 10:542), for which target sites in BCL6 are lost when U1 is reduced (FIG. 15). Likewise, miR-335 down-regulation up-regulates SOX4, which promotes epithelial-to-mesenchymal transition and enhances breast cancer metastases (Tavazoie et al., 2008, Nature 451(7175):147-52). The SOX4 3'UTR in HeLa is already shortened but the miR-335 binding site is restored by U1 over-expression (FIG. 14).

Figure 18:
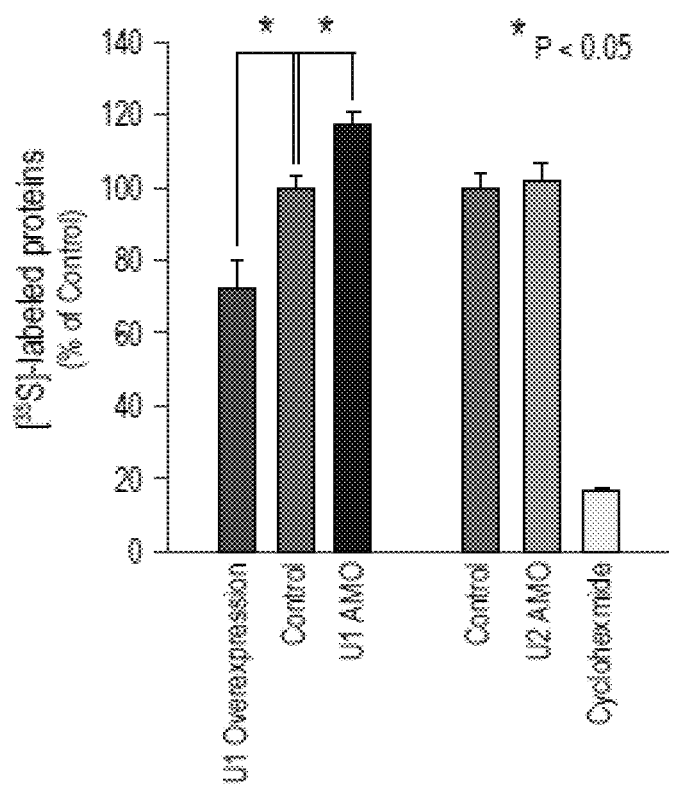
FIG. 18 depicts the results of experiments demonstrating that U1 levels changes affect global translation. Cells transfected with control or 1.5 µg U1 plasmid (24 hours) as well as 0.25 nmole U1 (left) or U2 (right) AMO (8 hours) were metabolically labeled with [$^{35}$S]methionine for 1 hour. The radioactivity incorporated into newly synthesized proteins, which were precipitated by TCA, was counted by scintillation.
Figure 19:
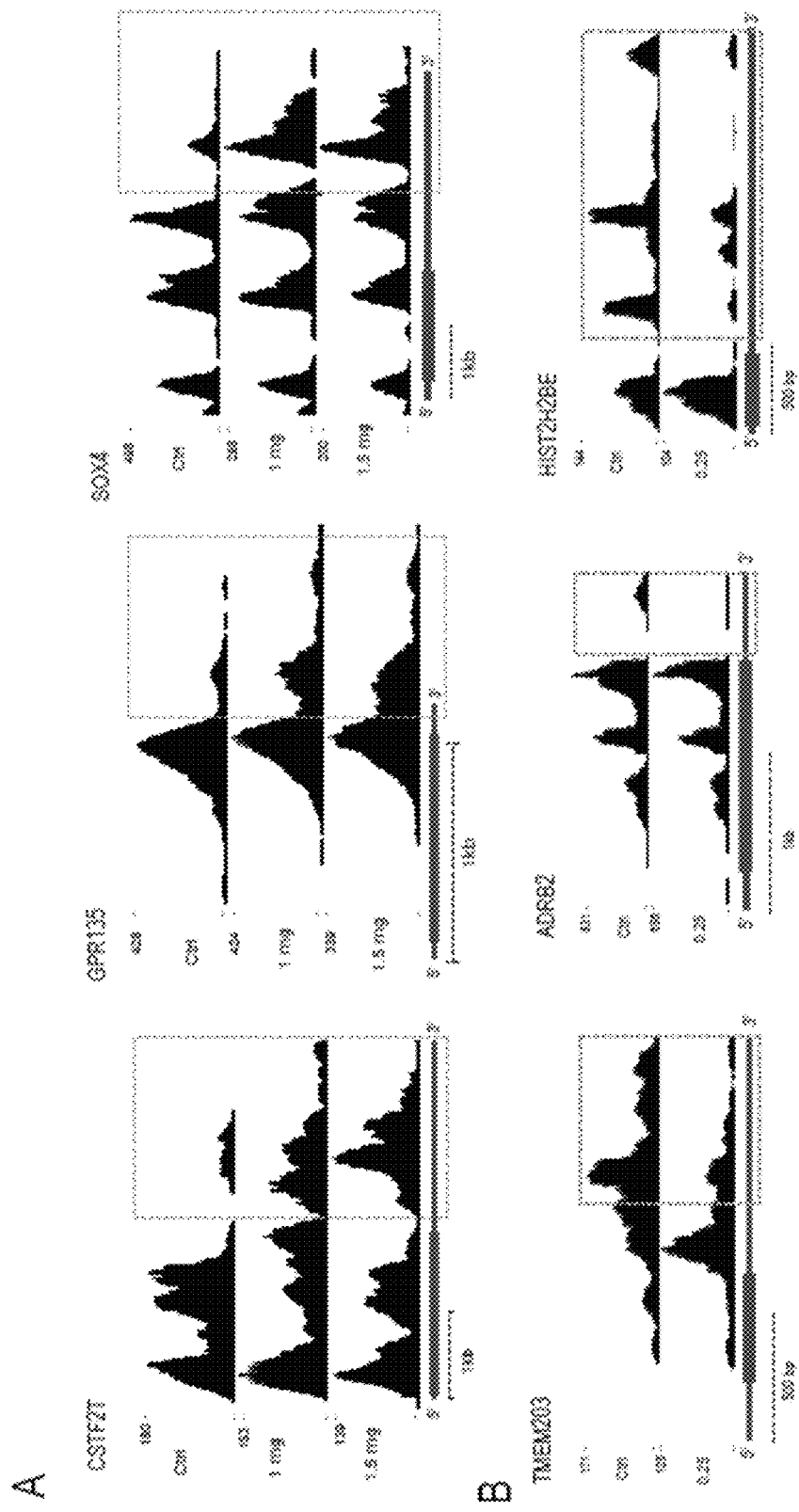
FIG. 19, comprising
Figure 20:
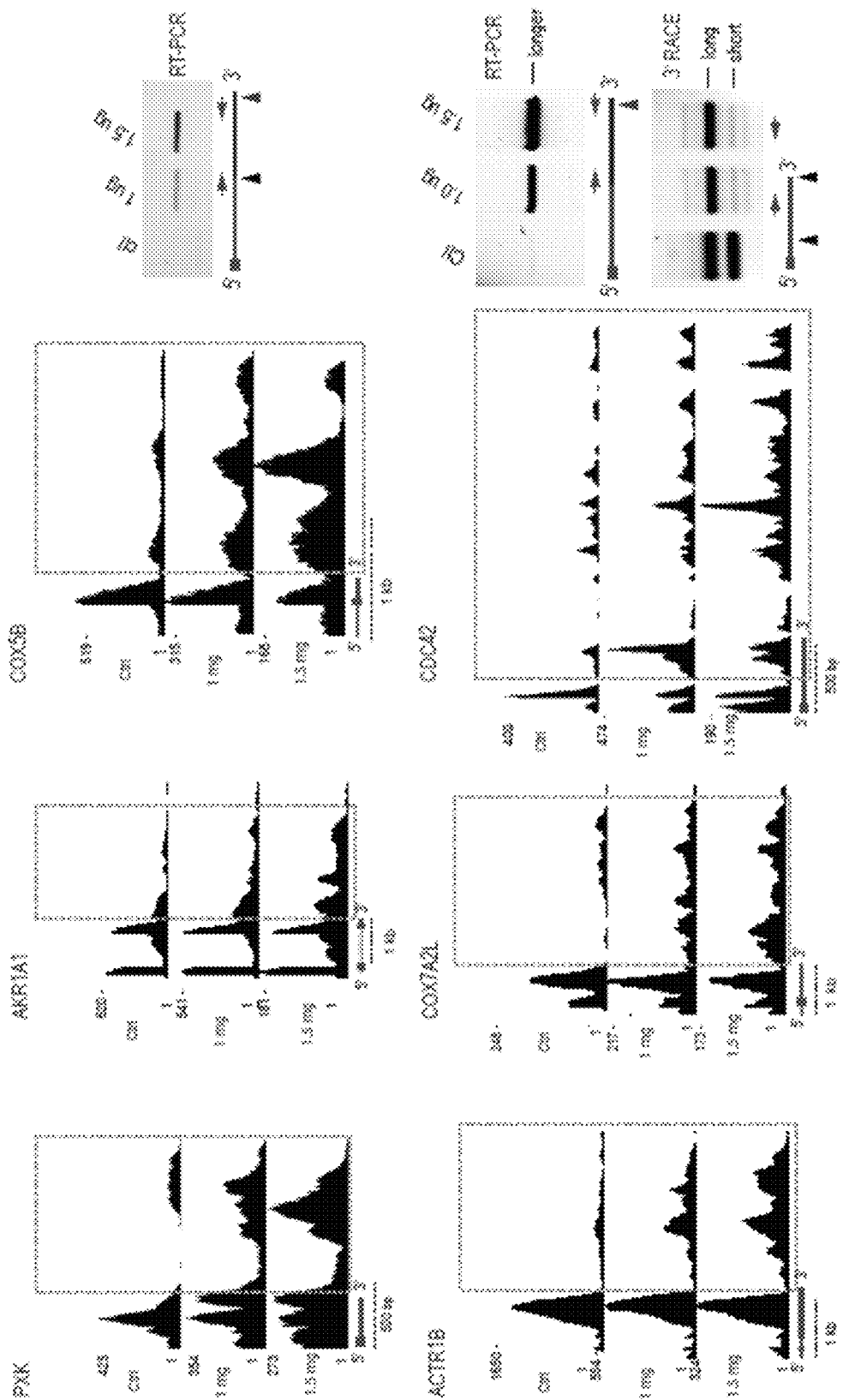
FIG. 20 depicts the results of experiments demonstrating that U1 overexpression results in transcription beyond canonical 3'end. HeLa cells transfected with control empty vector or U1 expression plasmids (1 µg and 1.5 µg, 24 hr) and labeled with 4-thiouridine to select nascent transcripts. RNA-seq maps of representative genes showing the last exon with dotted boxes indicating switch towards a UTR longer than the annotated canonical 3' end. Validation by RT-PCR and 3'RACE for a few genes is also shown. Black arrowheads indicate annotated PAS, arrowheads indicate newly identified PAS. A schematic representation of the UTR is provided below each gene, include the canonical annotated 3'end, and the extended UTR. The arrows indicate the primers' position.

Consistent with the expectation that 3'UTR shortening would generally up-regulate protein production from the corresponding mRNAs, which are numerous, low U1 AMO increased translation output by ~20% as measured by [$^{35}$S] methionine incorporation for 1 hr. In contrast, U1 over-expression decreased protein synthesis by 30% (FIG. 18). Thus, there is a large, ~50%, differential in protein synthesis activity between the most aggressive (U1 AMO) and the most attenuated (U1 over-expression, 1.5 µg) cancer cells. As controls, cycloheximide clearly inhibited protein synthesis, and U2 AMO, which had no effect on cancer phenotype, did not affect translation (FIG. 18). Notably, translation initiation factor over-expression is oncogenic (Furic et al., 2010, Proc Natl Acad Sci USA 7(32):14134-9), and a moderate protein synthesis inhibition of ~50% is sufficient to inhibit cancer cell growth (Medrano and Pardee, 1980, Proc Natl Acad Sci USA 77(7):4123-6).

In addition to many oncogenes, U1 levels caused 3'UTR length changes in numerous other genes that could contribute to the cancer phenotype. A much smaller number of alternative splicing events as well as mRNA level changes in many genes were observed and some of these likely also play a role in the cancer-related phenotype. The alternative splicing events could be a direct consequence of U1 level change, due to its role in splicing, but, without wishing to be bound by any particular theory, they could also be secondary to 3'UTR length changes in many other splicing regulators. Without wishing to be bound by any particular theory, the mRNA level changes could result from transcription changes, as many of the affected genes are transcription regulators. However, they could also be a direct result of telescripting change, as it could strongly affect mRNA stability (e.g. by removal of a stabilizing element).

The described experiments in a defined cancer cell system and quantitative assays revealed that relatively small telescripting changes could profoundly modulate cancer phenotype associated with tumor aggressiveness. Several lines of evidence support the physiological relevance of the insights gained from U1 modulation experiments and strongly suggest that the phenotypic changes are mediated primarily by telescripting regulation. First, telescripting deficit recapitulated the widespread 3'UTR shortening in cancer cell lines (Mayr and Bartel, 2009, Cell 138(4):673-84; Lin et al., 2012, Nucleic Acids Res 40(17):8460-71; Elkon et al., 2012, Genome Biol 13(7):R59; Fu et al., 2011, Genome Res 21(5):741-7) and in tumors (Lembo et al., 2012, PLoS One 7(2):e31129), and produced the same loss of miRNA repression of oncogenes that underlies many cancers. Second, the phenotype changes corresponded with both the directionality and the magnitude of the 3'UTR length changes, including the number of oncogenes and extent of the 3'UTRs change (e.g. dose-dependent shift to longer 3'UTRs; (FIGS. 14, 15 and 21). Third, unlike U1 AMO, U2 AMO, which also affects splicing and mRNA level, did not affect cancer phenotype (FIG. 24), strongly suggesting that the cancer phenotype is caused by U1's unique activity in telescripting. Further supporting the relevance of the present observations to clinical oncology, >45 genes for which 3'UTR shortening was observed have also been found to be shortened in lung and breast cancers that correlated with poor prognosis (Lembo et al., 2012, PLoS One 7(2):e31129).

What causes the telescripting deficit in cancer is unknown, but it does not necessarily depend on U1 decrease in absolute terms and could also be caused by transcription upregulation as well as by an increase in cleavage/polyadenylation factors. Indeed, without wishing to be bound by any particular theory, small transcription changes, which creates a U1 shortage relative to the normally safeguarded nascent transcripts that it needs to protect without necessarily decreasing U1 levels (Berg et al., 2012, Cell 150(1):53-64), could be sufficient to modulate telescripting and cause mRNA length changes and isoform regulation (Berg et al., 2012, Cell 150(1):53-64). Several factors, in addition to U1, that can influence 3'UTR length have been described, including components of the cleavage and polyadenylation machinery [Cstf64, CFI(m)68, PABPN1] (Di Giammartino et al., 2011, Mol Cell 43(6):853-66; de Klerk et al., 2012, Nucleic Acids Res 40(18):9089-101; Yao et al., 2012, Proc Natl Acad Sci USA 109(46):18773-8; Takagaki et al., 1996, Cell 87(5):941-52; Martin et al., 2012, Cell Rep 1(6):753-63). Given its central role in gene expression, it is likely that telescripting is a highly regulated process, and that mRNA length will be determined by the balance between the pro-shortening cleavage and polyadenylation machinery and telescripting capacity, which is highly dependent on transcriptional output relative to available U1 and likely varies in different cell types and physiologic states. It is proposed herein that telescripting deficit also explains 3'UTR shortening that is observed in proliferating cells as well as activated immune cells and neurons. Common to all of these is an increase in transcription and in proximal APA usage (Ji et al., 2011, Mol Syst Biol 7:534).

By determining mRNA length of thousands of genes, telescripting is a major APA and gene expression regulator, controlling target availability of miRNAs and other regulatory elements in 3'UTRs and protein-coding isoform switching resulting from PCPA in introns. A loss of miRNA targets on such a scale would likely also modulate robustness of miRNA regulation on remaining targets in other mRNAs (Ebert and Sharp, 2012, Cell 149(3):515-24) and reverberate throughout the network of the myriad factors that regulate mRNA function. Additionally, 3'UTRs are also highly enriched in regulatory elements, such as AU-rich motifs and sites for RNA binding proteins that impact every aspect of mRNA physiology (Chen and Shyu, 1995, Trends Biochem Sci 20(11):465-70), and these would also be affected by 3'UTR length changes.

A new perspective on oncogene involvement in cancer emerges from the studies presented herein. While cell transformation can be initiated by a somatic mutation in a single oncogene, the findings presented herein indicate that an established cancer cell also has a large number of oncogenes that are dysregulated co-transcriptionally by telescripting deficit and would be undetectable by genomic sequencing. Importantly, the data presented herein shows that U1 level changes alone can strongly modify mRNA length and its associated cancer phenotype. Therefore, it is demonstrated herein that telescripting modulation has potential as a broad-spectrum treatment for cancer and other phenotypes associated with mRNA shortening.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of increasing the length of more than one shortened transcript in a cell, the method comprising contacting a cell comprising more than one shortened transcript with an activator of endogenous U1 snRNP (U1), wherein one or more of endogenous U1 activity or U1 level associated with protecting a nascent transcript is increased in the cell, permitting an increase in the length of more than one transcript in a cell, wherein an increase in one or more of U1 activity and U1 level results in mRNAs with longer 3' untranslated regions, wherein the elongated region is the region of the 3' UTR prior to the polyA tail.

2. The method of claim 1, wherein the U1 activity is selected from the group consisting of U1 activity associated with protecting a transcript from premature termination by cleavage and polyadenylation (PCPA) at cryptic polyadenylation signals (PASs), U1 activity associated with protecting intronless genes from premature cleavage and polyadenylation, U1 activity associated with increasing gene length, U1 activity associated with transcription beyond the canonical 3' end to generate new mRNA sequences, and any combination thereof.

3. The method of claim 1, wherein an increase in one or more of U1 activity and U1 level results in transcript lengthening, permitting prevention of the removal of a regulatory element from the transcript.

4. The method of claim 3, wherein the regulatory element is selected from the group consisting of an RNA binding domain, a protein binding domain, a microRNA-binding site, an hnRNP protein-binding site, and any combination thereof.

5. The method of claim 3, wherein the lengthened transcript results in decreased expression of an encoded gene.

6. The method of claim 1, wherein the cell is selected from the group consisting of a stem cell, an immune cell and a neuron.

* * * * *